(12) United States Patent
Chang et al.

(10) Patent No.: US 9,907,858 B2
(45) Date of Patent: *Mar. 6, 2018

(54) PEPTIDE CORE-BASED MULTI-ARM LINKERS

(71) Applicant: Immunwork Inc., Taipei (TW)

(72) Inventors: Tse-Wen Chang, Taipei (TW); Hsing-Mao Chu, Taipei (TW)

(*) Notice: Subject to any disclaimer, the term of this patent is extended or adjusted under 35 U.S.C. 154(b) by 58 days.

This patent is subject to a terminal disclaimer.

(21) Appl. No.: 14/997,764

(22) Filed: Jan. 18, 2016

(65) Prior Publication Data

US 2016/0208020 A1     Jul. 21, 2016

Related U.S. Application Data

(60) Provisional application No. 62/104,405, filed on Jan. 16, 2015, provisional application No. 62/114,427, filed on Feb. 10, 2015, provisional application No. 62/137,737, filed on Mar. 24, 2015.

(51) Int. Cl.

| | | |
|---|---|---|
| *C07K 16/46* | (2006.01) |
| *C07K 16/30* | (2006.01) |
| *C07K 16/24* | (2006.01) |
| *C07K 16/18* | (2006.01) |
| *C07K 16/28* | (2006.01) |
| *C07K 16/22* | (2006.01) |
| *A61K 47/48* | (2006.01) |
| *A61K 31/4745* | (2006.01) |
| *A61K 31/537* | (2006.01) |
| *A61K 31/739* | (2006.01) |
| *C07K 16/32* | (2006.01) |
| *C07K 14/655* | (2006.01) |
| *C07K 14/715* | (2006.01) |
| *C07K 14/485* | (2006.01) |
| *A61K 31/397* | (2006.01) |
| *A61K 31/4709* | (2006.01) |
| *A61K 31/4545* | (2006.01) |

(52) U.S. Cl.
CPC ...... *A61K 47/48538* (2013.01); *A61K 31/397* (2013.01); *A61K 31/4545* (2013.01); *A61K 31/4709* (2013.01); *A61K 31/4745* (2013.01); *A61K 31/537* (2013.01); *A61K 31/739* (2013.01); *A61K 47/48215* (2013.01); *A61K 47/48246* (2013.01); *A61K 47/48384* (2013.01); *A61K 47/48546* (2013.01); *A61K 47/48561* (2013.01); *A61K 47/48692* (2013.01); *C07K 14/485* (2013.01); *C07K 14/655* (2013.01); *C07K 14/7151* (2013.01); *C07K 16/18* (2013.01); *C07K 16/22* (2013.01); *C07K 16/241* (2013.01); *C07K 16/244* (2013.01); *C07K 16/2803* (2013.01); *C07K 16/2809* (2013.01); *C07K 16/2818* (2013.01); *C07K 16/2863* (2013.01); *C07K 16/2875* (2013.01); *C07K 16/2887* (2013.01); *C07K 16/32* (2013.01); *C07K 16/468* (2013.01); *C07K 2317/21* (2013.01); *C07K 2317/24* (2013.01); *C07K 2317/31* (2013.01); *C07K 2317/55* (2013.01); *C07K 2317/622* (2013.01); *C07K 2317/64* (2013.01); *C07K 2317/71* (2013.01); *C07K 2317/73* (2013.01); *C07K 2317/732* (2013.01); *C07K 2317/76* (2013.01); *C07K 2319/30* (2013.01); *C07K 2319/33* (2013.01)

(58) Field of Classification Search
None
See application file for complete search history.

(56) References Cited

PUBLICATIONS

Gaudreault et al, Investigative Ophthalmology & Visual Sciences, 2005, vol. 46, pp. 726-733.*
Henricks et al, Cancer Treatment Reviews, 2015, vol. 41, pp. 859-867.*
Sun and Coy, Current Drug Delivery, 2011, vol. 8, pp. 2-10.*
Onori et al, International Journal of Cancer, 2009, vol. 127, pp. 43-54.*
Luster, European Journal of Nuclear medicine and Molecular Imaging, 2003, vol. 30, pp. 1371-1377.*
Brooks et al, Clinical Cancer Research, 2012, vol. 18, pp. 1855-1862.*
Lewiecki et al, Expert Opinion in Biological Therapy, 2006, vol. 6, pp. 1041-1050.*

* cited by examiner

*Primary Examiner* — Karen A. Canella

(57) ABSTRACT

The present disclosure provides various molecular constructs having a targeting element and/or an effector element. Methods for treating various diseases using such molecular constructs are also disclosed.

33 Claims, 26 Drawing Sheets

SEQUENCE LISTING

<160> NUMBER OF SEQ ID NOS: 44

<210> SEQ ID NO 1
<211> LENGTH: 4
<212> TYPE: PRT
<213> ORGANISM: Artificial Sequence
<220> FEATURE:
<223> OTHER INFORMATION: filler sequence-1

<400> SEQUENCE: 1

Gly Gly Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: filler sequence-2

<400> SEQUENCE: 2

Gly Ser Gly Ser
1

```
<210> SEQ ID NO 3
<211> LENGTH: 4
<212> TYPE: PRT
<213> ORGANISM: Artificial Sequence
<220> FEATURE:
<223> OTHER INFORMATION: filler sequence-3

<400> SEQUENCE: 3

Gly Gly Ser Gly
1

<210> SEQ ID NO 4
<211> LENGTH: 5
<212> TYPE: PRT
<213> ORGANISM: Artificial Sequence
<220> FEATURE:
<223> OTHER INFORMATION: filler sequence-4

<400> SEQUENCE: 4

Gly Ser Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: filler sequence-5

<400> SEQUENCE: 5

Ser Gly Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: filler sequence-6

<400> SEQUENCE: 6

Gly Gly Gly Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: filler sequence-7

<400> SEQUENCE: 7

Gly Gly Ser Gly Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: filler sequence-8

<400> SEQUENCE: 8

Gly Gly Ser Gly Gly Ser Gly
1               5
```

```
<210> SEQ ID NO 9
<211> LENGTH: 8
<212> TYPE: PRT
<213> ORGANISM: Artificial Sequence
<220> FEATURE:
<223> OTHER INFORMATION: filler sequence-9

<400> SEQUENCE: 9

Ser Gly Ser Gly Gly Ser Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: filler sequence-10

<400> SEQUENCE: 10

Gly Ser Gly Gly Ser Gly Ser Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: filler sequence-11

<400> SEQUENCE: 11

Ser Gly Gly Ser Gly Gly Ser Gly Ser Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: filler sequence-12

<400> SEQUENCE: 12

Gly Gly Ser Gly Gly Ser Gly Gly Ser Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: filler sequence-13

<400> SEQUENCE: 13

Ser Gly Gly Ser Gly Gly Ser Gly Ser Gly Gly Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: filler sequence-14

<400> SEQUENCE: 14

Gly Gly Gly Gly Ser Gly Gly Ser Gly Gly Gly Gly Ser
1               5                   10
```

```
<210> SEQ ID NO 15
<211> LENGTH: 14
<212> TYPE: PRT
<213> ORGANISM: Artificial Sequence
<220> FEATURE:
<223> OTHER INFORMATION: filler sequence-15

<400> SEQUENCE: 15

Gly Gly Gly Ser Gly Ser Gly Ser Gly Ser Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: filler sequence-16

<400> SEQUENCE: 16

Ser Gly Ser Gly Gly Gly Gly Gly Ser Gly Gly Ser Gly Ser Gly
1               5                   10                  15

<210> SEQ ID NO 17
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-1

<400> SEQUENCE: 17

Cys Gly Gly Ser Gly Gly Ser Gly Gly Ser Lys Gly Ser Gly Ser Lys
1               5                   10                  15

<210> SEQ ID NO 18
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptitde core-2

<400> SEQUENCE: 18

Cys Gly Gly Ser Gly Gly Ser Gly Gly Ser Lys Gly Ser Gly Ser Lys
1               5                   10                  15

Gly Ser Lys

<210> SEQ ID NO 19
<211> LENGTH: 31
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide-3

<400> SEQUENCE: 19

Cys Gly Ser Lys Gly Ser Lys Gly Ser Lys Gly Ser Lys Gly Ser Lys
1               5                   10                  15

Gly Ser Lys Gly Ser Lys Gly Ser Lys Gly Ser Lys Gly Ser Lys
```

```
                       20                  25                  30

<210> SEQ ID NO 20
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-4

<400> SEQUENCE: 20

Xaa Gly Gly Ser Gly Gly Ser Gly Gly Ser Lys Gly Ser Gly Ser Lys
1               5                   10                  15

<210> SEQ ID NO 21
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-5

<400> SEQUENCE: 21

Xaa Gly Gly Ser Gly Gly Ser Gly Gly Ser Lys Gly Ser Gly Ser Lys
1               5                   10                  15

Gly Ser Lys

<210> SEQ ID NO 22
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is L-azidohomoalanine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-6

<400> SEQUENCE: 22

Xaa Gly Gly Ser Gly Gly Ser Gly Gly Ser Lys Gly Ser Gly Ser Lys
1               5                   10                  15

Gly Ser Lys

<210> SEQ ID NO 23
<211> LENGTH: 21
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
```

-continued

```
<221> NAME/KEY: MOD_RES
<222> LOCATION: 1
<223> OTHER INFORMATION: ACETYLATION
<220> FEATURE:
<223> OTHER INFORMATION: polypeptide core-7

<400> SEQUENCE: 23

Xaa Gly Gly Ser Gly Gly Ser Gly Gly Ser Lys Gly Ser Gly Ser Lys
1               5                   10                  15

Gly Ser Gly Ser Cys
            20

<210> SEQ ID NO 24
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-8
<220> FEATURE:
<221> NAME/KEY: MOD_RES
<222> LOCATION: 2,4,6
<223> OTHER INFORMATION: Xaa is PEGylated amino acid with two EG units

<400> SEQUENCE: 24

Cys Xaa Lys Xaa Lys Xaa Lys
1               5

<210> SEQ ID NO 25
<211> LENGTH: 11
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-9
<220> FEATURE:
<221> NAME/KEY: MOD_RES
<222> LOCATION: 2,4,6,8,10
<223> OTHER INFORMATION: Xaa is PEGylated amino acid with six EG units

<400> SEQUENCE: 25

Cys Xaa Lys Xaa Lys Xaa Lys Xaa Lys Xaa Lys
1               5                   10

<210> SEQ ID NO 26
<211> LENGTH: 121
<212> TYPE: PRT
<213> ORGANISM: Artificial Sequence
<220> FEATURE:
<223> OTHER INFORMATION: 24C10-VH

<400> SEQUENCE: 26

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Ser Phe Ser
            20                  25                  30

Trp Met Asn Trp Val Lys Trp Gly Pro Gly Gln Gly Leu Glu Trp Ile
        35                  40                  45

Gly Arg Ile Tyr Pro Gly Asn Gly Asp Thr Asn Tyr Asn Gly Lys Phe
    50                  55                  60

Lys Gly Lys Ala Thr Leu Thr Ala Asp Lys Ser Ser Asn Thr Ala Tyr
```

```
                    65                  70                  75                  80
Met Gln Leu Ser Ser Leu Thr Ser Val Asp Ser Ala Val Tyr Phe Cys
                        85                  90                  95

Ala Arg Trp Val Tyr Ser Gly Asn Asn Tyr Ala Val Asp Tyr Trp Gly
                100                 105                 110

Gln Gly Thr Ser Val Thr Val Ser Ser
            115                 120

<210> SEQ ID NO 27
<211> LENGTH: 113
<212> TYPE: PRT
<213> ORGANISM: Artificial Sequence
<220> FEATURE:
<223> OTHER INFORMATION: 24C10-VL

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
            100                 105                 110

Lys

<210> SEQ ID NO 28
<211> LENGTH: 112
<212> TYPE: PRT
<213> ORGANISM: Artificial Sequence
<220> FEATURE:
<223> OTHER INFORMATION: 1F10-VH

<400> SEQUENCE: 28

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Glu Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Tyr Tyr Gly Ser Tyr Trp Gly Gln Gly Thr Leu Val Thr Val Ser Ala
            100                 105                 110

<210> SEQ ID NO 29
<211> LENGTH: 111
<212> TYPE: PRT
```

-continued

<213> ORGANISM: Artificial Sequence
<220> FEATURE:
<223> OTHER INFORMATION: 1F10-VL

<400> SEQUENCE: 29

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Gly Tyr Met Asp Trp Tyr Gln Gln Lys Pro Gly Gln Pro Pro
        35                  40                  45

Lys Leu Leu Ile Phe Ala Ala Ser Asn Leu Lys Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Asn
                85                  90                  95

Glu Tyr Pro Trp Thr Phe Gly Gly Gly Thr Lys Leu Glu Ile Lys
            100                 105                 110

<210> SEQ ID NO 30
<211> LENGTH: 123
<212> TYPE: PRT
<213> ORGANISM: Artificial Sequence
<220> FEATURE:
<223> OTHER INFORMATION: LH7.2-VH

<400> SEQUENCE: 30

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Asp Tyr Thr Phe Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Arg Arg Ser Glu Asp Thr Ala Met Tyr Tyr Cys
                85                  90                  95

Ala Arg His Gly Glu Ile Gly Tyr Ser Ser Ala Trp Phe Ala Tyr
            100                 105                 110

Trp Gly Gln Gly Thr Leu Val Thr Val Ser Ala
        115                 120

<210> SEQ ID NO 31
<211> LENGTH: 108
<212> TYPE: PRT
<213> ORGANISM: Artificial Sequence
<220> FEATURE:
<223> OTHER INFORMATION: LH7.2-VL

<400> SEQUENCE: 31

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

```
Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Tyr
                 85                  90                  95

Thr Phe Gly Gly Gly Thr Lys Leu Glu Ile Lys Arg
                100                 105

<210> SEQ ID NO 32
<211> LENGTH: 252
<212> TYPE: PRT
<213> ORGANISM: Artificial Sequence
<220> FEATURE:
<223> OTHER INFORMATION: 1F10 scFv

<400> SEQUENCE: 32

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                 20                  25                  30

Gly Asp Gly Tyr Met Asp Trp Tyr Gln Gln Lys Pro Gly Gln Pro Pro
             35                  40                  45

Lys Leu Leu Ile Phe Ala Ala Ser Asn Leu Lys Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Thr Asn
                 85                  90                  95

Glu Tyr Pro Trp Thr Phe Gly Gly Gly Thr Lys Leu Glu Ile Lys Gly
                100                 105                 110

Ser Thr Ser Gly Ser Gly Lys Pro Gly Ser Gly Glu Gly Ser Thr Lys
             115                 120                 125

Gly Gln Ile Gln Leu Val Gln Ser Gly Pro Glu Leu Lys Lys Pro Gly
         130                 135                 140

Glu Thr Val Lys Ile Ser Cys Lys Ala Ser Gly Tyr Thr Phe Thr Asp
145                 150                 155                 160

Tyr Ser Met His Trp Val Lys Gln Ala Pro Gly Glu Gly Leu Lys Trp
                165                 170                 175

Met Gly Trp Ile Asn Thr Glu Thr Gly Glu Pro Thr Tyr Ala Asp Asp
             180                 185                 190

Phe Lys Gly Arg Phe Ala Phe Ser Leu Glu Thr Ser Ala Ser Thr Ala
         195                 200                 205

Tyr Leu Gln Ile Asn Asn Leu Lys Asn Glu Asp Thr Ala Thr Tyr Phe
     210                 215                 220

Cys Tyr Tyr Gly Ser Tyr Trp Gly Gln Gly Thr Leu Val Thr Val Ser
225                 230                 235                 240

Ala Gly Gly Gly Gly Ser Gly Gly Gly Ser Cys
                245                 250

<210> SEQ ID NO 33
<211> LENGTH: 260
<212> TYPE: PRT
<213> ORGANISM: Artificial Sequence
<220> FEATURE:
<223> OTHER INFORMATION: CVII scFv
```

-continued

```
<400> SEQUENCE: 33

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Met Leu Val Glu Ser Gly Gly Gly Leu Val Lys Pro Gly Gly Ser Leu
130                 135                 140

Lys Leu Ser Cys Ala Ala Ser Gly Phe Thr Phe Ser Ser Tyr Ala Met
145                 150                 155                 160

Ser Trp Val Arg Gln Thr Pro Glu Lys Arg Leu Glu Trp Val Ala Thr
                165                 170                 175

Ile Thr Ser Gly Gly Asp Tyr Thr Phe Tyr Pro Asp Ser Val Lys Gly
            180                 185                 190

Arg Phe Thr Ile Ser Arg Asp Asn Ala Lys Asn Thr Leu Tyr Leu Gln
        195                 200                 205

Met Ser Ser Arg Arg Ser Glu Asp Thr Ala Met Tyr Tyr Cys Ala Arg
210                 215                 220

His Gly Glu Ile Gly Tyr Gly Ser Ser Ala Trp Phe Ala Tyr Trp Gly
225                 230                 235                 240

Gln Gly Thr Leu Val Thr Val Ser Ala Gly Gly Gly Ser Gly Gly
                245                 250                 255

Gly Gly Ser Cys
            260

<210> SEQ ID NO 34
<211> LENGTH: 257
<212> TYPE: PRT
<213> ORGANISM: Artificial Sequence
<220> FEATURE:
<223> OTHER INFORMATION: Trastuzumab scFv

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                    85                  90                  95
Thr Phe Gly Gln Gly Thr Lys Val Glu Ile Lys Arg Gly Ser Thr Ser
                100                 105                 110

Gly Ser Gly Lys Pro Gly Ser Gly Glu Gly Ser Thr Lys Gly Glu Val
            115                 120                 125

Gln Leu Val Glu Ser Gly Gly Gly Leu Val Gln Pro Gly Gly Ser Leu
        130                 135                 140

Arg Leu Ser Cys Ala Ala Ser Gly Phe Asn Ile Lys Asp Thr Tyr Ile
145                 150                 155                 160

His Trp Val Arg Gln Ala Pro Gly Lys Gly Leu Glu Trp Val Ala Arg
                165                 170                 175

Ile Tyr Pro Thr Asn Gly Tyr Thr Arg Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ser Arg
210                 215                 220

Trp Gly Gly Asp Gly Phe Tyr Ala Met Asp Tyr Trp Gly Gln Gly Thr
225                 230                 235                 240

Leu Val Thr Val Ser Ser Gly Gly Gly Gly Ser Gly Gly Gly Gly Ser
                245                 250                 255

Cys

<210> SEQ ID NO 35
<211> LENGTH: 257
<212> TYPE: PRT
<213> ORGANISM: Artificial Sequence
<220> FEATURE:
<223> OTHER INFORMATION: Rituximab scFv

<400> SEQUENCE: 35

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Gly Ser Thr Ser Gly
                100                 105                 110

Ser Gly Lys Pro Gly Ser Gly Glu Gly Ser Thr Lys Gly Gln Val Gln
            115                 120                 125

Leu Gln Gln Pro Gly Ala Glu Leu Val Lys Pro Gly Ala Ser Val Lys
        130                 135                 140

Met Ser Cys Lys Ala Ser Gly Tyr Thr Phe Thr Ser Tyr Asn Met His
145                 150                 155                 160

Trp Val Lys Gln Thr Pro Gly Arg Gly Leu Glu Trp Ile Gly Ala Ile
                165                 170                 175

Tyr Pro Gly Asn Gly Asp Thr Ser Tyr Asn Gln Lys Phe Lys Gly Lys
            180                 185                 190
```

```
Ala Thr Leu Thr Ala Asp Lys Ser Ser Thr Ala Tyr Met Gln Leu
        195                 200                 205

Ser Ser Leu Thr Ser Glu Asp Ser Ala Val Tyr Tyr Cys Ala Arg Ser
    210                 215                 220

Thr Tyr Tyr Gly Gly Asp Trp Tyr Phe Asn Val Trp Gly Ala Gly Thr
225                 230                 235                 240

Thr Val Thr Val Ser Ala Gly Gly Gly Ser Gly Gly Gly Ser
                245                 250                 255

Cys

<210> SEQ ID NO 36
<211> LENGTH: 256
<212> TYPE: PRT
<213> ORGANISM: Artificial Sequence
<220> FEATURE:
<223> OTHER INFORMATION: Centuxiamb scFv

<400> SEQUENCE: 36

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Lys Gln Ser Gly Pro Gly Leu Val Gln Pro Ser Gln Ser Leu
    130                 135                 140

Ser Ile Thr Cys Thr Val Ser Gly Phe Ser Leu Thr Asn Tyr Gly Val
145                 150                 155                 160

His Trp Val Arg Gln Ser Pro Gly Lys Gly Leu Glu Trp Leu Gly Val
                165                 170                 175

Ile Trp Ser Gly Gly Asn Thr Asp Tyr Asn Thr Pro Phe Thr Ser Arg
            180                 185                 190

Leu Ser Ile Asn Lys Asp Asn Ser Lys Ser Gln Val Phe Phe Lys Met
        195                 200                 205

Asn Ser Leu Gln Ser Asn Asp Thr Ala Ile Tyr Tyr Cys Ala Arg Ala
    210                 215                 220

Leu Thr Tyr Tyr Asp Tyr Glu Phe Ala Tyr Trp Gly Gln Gly Thr Leu
225                 230                 235                 240

Val Thr Val Ser Ala Gly Gly Gly Gly Ser Gly Gly Gly Gly Ser Cys
                245                 250                 255

<210> SEQ ID NO 37
<211> LENGTH: 252
<212> TYPE: PRT
<213> ORGANISM: Artificial Sequence
<220> FEATURE:
```

<223> OTHER INFORMATION: Nivolumab scFv

<400> SEQUENCE: 37

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Glu Ser Gly Gly Val Val Gln Pro Gly Arg Ser Leu
    130                 135                 140

Arg Leu Asp Cys Lys Ala Ser Gly Ile Thr Phe Ser Asn Ser Gly Met
145                 150                 155                 160

His Trp Val Arg Gln Ala Pro Gly Lys Gly Leu Glu Trp Val Ala Val
                165                 170                 175

Ile Trp Tyr Asp Gly Ser Lys Arg Tyr Tyr Ala Asp Ser Val Lys Gly
            180                 185                 190

Arg Phe Thr Ile Ser Arg Asp Asn Ser Lys Asn Thr Leu Phe Leu Gln
        195                 200                 205

Met Asn Ser Leu Arg Ala Glu Asp Thr Ala Val Tyr Tyr Cys Ala Thr
    210                 215                 220

Asn Asp Asp Tyr Trp Gly Gln Gly Thr Leu Val Thr Val Ser Ser Ser
225                 230                 235                 240

Ser Gly Gly Gly Gly Ser Gly Gly Gly Ser Cys
                245                 250
```

<210> SEQ ID NO 38
<211> LENGTH: 255
<212> TYPE: PRT
<213> ORGANISM: Artificial Sequence
<220> FEATURE:
<223> OTHER INFORMATION: Ipilimumab scFv

<400> SEQUENCE: 38

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

```
Trp Thr Phe Gly Gln Gly Thr Lys Val Glu Ile Lys Gly Ser Thr Ser
            100                 105                 110

Gly Ser Gly Lys Pro Gly Ser Gly Glu Gly Ser Thr Lys Gly Gln Val
            115                 120                 125

Gln Leu Val Glu Ser Gly Gly Val Val Gln Pro Gly Arg Ser Leu
130                 135                 140

Arg Leu Ser Cys Ala Ala Ser Gly Phe Thr Phe Ser Ser Tyr Thr Met
145                 150                 155                 160

His Trp Val Arg Gln Ala Pro Gly Lys Gly Leu Glu Trp Val Thr Phe
                    165                 170                 175

Ile Ser Tyr Asp Gly Asn Asn Lys Tyr Tyr Ala Asp Ser Val Lys Gly
                180                 185                 190

Arg Phe Thr Ile Ser Arg Asp Asn Ser Lys Asn Thr Leu Tyr Leu Gln
                    195                 200                 205

Met Asn Ser Leu Arg Ala Glu Asp Thr Ala Ile Tyr Tyr Cys Ala Arg
            210                 215                 220

Thr Gly Trp Leu Gly Pro Phe Asp Tyr Trp Gly Gln Gly Thr Leu Val
225                 230                 235                 240

Thr Val Ser Ser Gly Gly Gly Gly Ser Gly Gly Gly Gly Ser Cys
                245                 250                 255

<210> SEQ ID NO 39
<211> LENGTH: 260
<212> TYPE: PRT
<213> ORGANISM: Artificial Sequence
<220> FEATURE:
<223> OTHER INFORMATION: Ranibizuman scFv

<400> SEQUENCE: 39

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
            115                 120                 125

Gln Leu Val Glu Ser Gly Gly Gly Leu Val Gln Pro Gly Gly Ser Leu
130                 135                 140

Arg Leu Ser Cys Ala Ala Ser Gly Tyr Asp Phe Thr His Tyr Gly Met
145                 150                 155                 160

Asn Trp Val Arg Gln Ala Pro Gly Lys Gly Leu Glu Trp Val Gly Trp
                    165                 170                 175

Ile Asn Thr Tyr Thr Gly Glu Pro Thr Tyr Ala Ala Asp Phe Lys Arg
                180                 185                 190

Arg Phe Thr Phe Ser Leu Asp Thr Ser Lys Ser Thr Ala Tyr Leu Gln
                    195                 200                 205
```

```
Met Asn Ser Leu Arg Ala Glu Asp Thr Ala Val Tyr Tyr Cys Ala Lys
        210                 215                 220

Tyr Pro Tyr Tyr Tyr Gly Thr Ser His Trp Tyr Phe Asp Val Trp Gly
225                 230                 235                 240

Gln Gly Thr Leu Val Thr Val Ser Ser Gly Gly Gly Ser Gly Gly
                245                 250                 255

Gly Gly Ser Cys
            260

<210> SEQ ID NO 40
<211> LENGTH: 258
<212> TYPE: PRT
<213> ORGANISM: Artificial Sequence
<220> FEATURE:
<223> OTHER INFORMATION: Adalimumab scFv

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Arg Ser Leu
130                 135                 140

Arg Leu Ser Cys Ala Ala Ser Gly Phe Thr Phe Asp Asp Tyr Ala Met
145                 150                 155                 160

His Trp Val Arg Gln Ala Pro Gly Lys Gly Leu Glu Trp Val Ser Ala
                165                 170                 175

Ile Thr Trp Asn Ser Gly His Ile Asp Tyr Ala Asp Ser Val Glu Gly
            180                 185                 190

Arg Phe Thr Ile Ser Arg Asp Asn Ala Lys Asn Ser Leu Tyr Leu Gln
        195                 200                 205

Met Asn Ser Leu Arg Ala Glu Asp Thr Ala Val Tyr Tyr Cys Ala Lys
        210                 215                 220

Val Ser Tyr Leu Ser Thr Ala Ser Ser Leu Asp Tyr Trp Gly Gln Gly
225                 230                 235                 240

Thr Leu Val Thr Val Ser Ser Gly Gly Gly Ser Gly Gly Gly Gly
                245                 250                 255

Ser Cys

<210> SEQ ID NO 41
<211> LENGTH: 255
<212> TYPE: PRT
<213> ORGANISM: Artificial Sequence
<220> FEATURE:
```

<223> OTHER INFORMATION: mutated teplizumab scFv

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
            85                  90                  95

Phe Gly Gln Gly Thr Lys Leu Gln Ile Thr Arg Gly Ser Thr Ser Gly
            100                 105                 110

Ser Gly Lys Pro Gly Ser Gly Glu Gly Ser Thr Lys Gly Gln Val Gln
            115                 120                 125

Leu Val Gln Ser Gly Gly Gly Val Val Gln Pro Gly Arg Ser Leu Arg
    130                 135                 140

Leu Ser Cys Lys Ala Ser Gly Tyr Thr Phe Thr Arg Tyr Thr Met His
145                 150                 155                 160

Trp Val Arg Gln Ala Pro Gly Lys Gly Leu Glu Trp Ile Gly Tyr Ile
            165                 170                 175

Asn Pro Ser Arg Gly Tyr Thr Asn Tyr Asn Gln Lys Val Lys Asp Arg
            180                 185                 190

Phe Thr Ile Ser Arg Asp Asn Ser Lys Asn Thr Ala Phe Leu Gln Met
            195                 200                 205

Asp Ser Leu Arg Pro Glu Asp Thr Gly Val Tyr Phe Cys Ala Arg Tyr
    210                 215                 220

Tyr Asp Asp His Tyr Ser Leu Asp Tyr Trp Gly Gln Gly Thr Pro Val
225                 230                 235                 240

Thr Val Ser Ser Gly Gly Gly Ser Gly Gly Gly Ser Cys
            245                 250                 255

<210> SEQ ID NO 42
<211> LENGTH: 41
<212> TYPE: DNA
<213> ORGANISM: Artificial Sequence
<220> FEATURE:
<223> OTHER INFORMATION: scFv of adalimumab- forward primer

<400> SEQUENCE: 42
gtatctctcg agaaaagaga tattcagatg acgcaatccc c                41

<210> SEQ ID NO 43
<211> LENGTH: 34
<212> TYPE: DNA
<213> ORGANISM: Artificial Sequence
<220> FEATURE:
<223> OTHER INFORMATION: scFv of adalimumab- reverse primer

<400> SEQUENCE: 43
gtatctgcgg ccgcttaaca ggagccaccg ccac                        34

<210> SEQ ID NO 44
<211> LENGTH: 14

```
<212> TYPE: PRT
<213> ORGANISM: Artificial Sequence
<220> FEATURE:
<223> OTHER INFORMATION: CCK analogue
<220> FEATURE:
<221> NAME/KEY: MOD_RES
<222> LOCATION: 8
<223> OTHER INFORMATION: SO4H modification
      SULFATATION
<220> FEATURE:
<221> NAME/KEY: MOD_RES
<222> LOCATION: 9,12
<223> OTHER INFORMATION: Xaa is NOR-leucine

<400> SEQUENCE: 44

Cys Gly Gly Gly Gly Ser Asp Tyr Xaa Gly Trp Xaa Asp Phe
1               5                   10
```

PEPTIDE CORE-BASED MULTI-ARM LINKERS

CROSS-REFERENCE TO RELATED APPLICATIONS

This application relates to and claims the benefit of U.S. Provisional Application No. 62/104,405, filed Jan. 16, 2015, U.S. Provisional Application No. 62/114,427, filed Feb. 10, 2015, and U.S. Provisional Application No. 62/137,737, filed Mar. 24, 2015; the contents of the applications are incorporated herein by reference in their entirety.

BACKGROUND OF THE INVENTION

1. Field of the Invention

The present disclosure relates to the field of pharmaceuticals; more particularly, to multi-functional molecular constructs, e.g., those having targeting and effector elements for delivering the effector (e.g., therapeutic drug) to targeted sites.

2. Description of the Related Art

The continual advancement of a broad array of methodologies for screening and selecting monoclonal antibodies (mAbs) for targeted antigens has helped the development of a good number of therapeutic antibodies for many diseases that were regarded as untreatable just a few years ago. According to Therapeutic Antibody Database, approximately 2,800 antibodies have been studied or are being planned for studies in human clinical trials, and approximately 80 antibodies have been approved by governmental drug regulatory agencies for clinical uses. The large amount of data on the therapeutic effects of antibodies has provided information concerning the pharmacological mechanisms how antibodies act as therapeutics.

One major pharmacologic mechanism for antibodies acting as therapeutics is that, antibodies can neutralize or trap disease-causing mediators, which may be cytokines or immune components present in the blood circulation, interstitial space, or in the lymph nodes. The neutralizing activity inhibits the interaction of the disease-causing mediators with their receptors. It should be noted that fusion proteins of the soluble receptors or the extracellular portions of receptors of cytokines and the Fc portion of IgG, which act by neutralizing the cytokines or immune factors in a similar fashion as neutralizing antibodies, have also been developed as therapeutic agents.

Several therapeutic antibodies that have been approved for clinical applications or subjected to clinical developments mediate their pharmacologic effects by binding to receptors, thereby blocking the interaction of the receptors with their ligands. For those antibody drugs, Fc-mediated mechanisms, such as antibody-dependent cellular cytotoxicity (ADCC) and complement-mediated cytolysis (CMC), are not the intended mechanisms for the antibodies.

Some therapeutic antibodies bind to certain surface antigens on target cells and render Fc-mediated functions and other mechanisms on the target cells. The most important Fc-mediated mechanisms are antibody-dependent cellular cytotoxicity (ADCC) and complement-mediated cytolysis (CMC), which both will cause the lysis of the antibody-bound target cells. Some antibodies binding to certain cell surface antigens can induce apoptosis of the bound target cells.

Antibodies can also serve as carriers of cytotoxic molecules or other therapeutic agents without the antibodies' serving obvious therapeutic effector functions. In general, those antibodies bind to "tumor-associated" antigens on target cells, but cannot cause cell lysis by themselves. Antibodies specific for CD19 and CD22 on B lymphomas are well known. For many years, those antibodies have been explored as carriers for cytotoxic agents, including radioactive nuclides with very short half-lives, such as $^{90}$Y, $^{131}$I, and $^{177}$Lu. Some antibodies have also been studied as targeting agents for liposomes loaded with cytotoxic drugs, such as doxorubicin, paclitaxel, and amphotericin B. The field of antibody drug conjugates (ADC) has experienced an explosive phase of research and development in recent years, mainly attributing to the development of extremely cytotoxic drugs, such as auristatin, maytansine, calicheamicin, and camptothecin, and of methodologies for conjugating the cytotoxic molecules onto antibody molecules. Those ADCs have been designed to target diffusive (or liquid) tumors of the blood, lymphoid system, and bone marrow, including various types of lymphomas and leukemia, expressing one or more unique CD markers. Some ADCs are also being developed for solid tumors. A few of this new generation of antibody drug conjugates have been approved for clinical uses and many are in clinical trials.

However, in the first generation of ADCs, the cytotoxic drug molecules are linked non-selectively to cysteine or lysine residues in the antibody, thereby resulting in a heterogeneous mixture of ADCs with different numbers of drug molecules per ADC. This approach leads to some safety and efficacy issues. For example, the first FDA-approved ADC, gemtuzumab ozogamicin, for treating acute myelogenous leukemia, is now withdrawn from the market due to unacceptable toxicity.

The concept and methodology for preparing antibodies with dual specificities germinated more than three decades ago. In recent year, the advancement in recombinant antibody engineering methodologies and the drive to develop improved medicine has stimulated the development bi-specific antibodies adopting a large variety of structural configurations.

For example, the bi-valent or multivalent antibodies may contain two or more antigen-binding sites. A number of methods have been reported for preparing multivalent antibodies by covalently linking three or four Fab fragments via a connecting structure. For example, antibodies have been engineered to express tandem three or four Fab repeats.

Several methods for producing multivalent antibodies by employing synthetic crosslinkers to associate, chemically, different antibodies or binding fragments have been disclosed. One approach involves chemically cross-linking three, four, and more separately Fab fragments using different linkers. Another method to produce a construct with multiple Fabs that are assembled to one-dimensional DNA scaffold was provided. Those various multivalent Ab constructs designed for binding to target molecules differ among one another in size, half-lives, flexibility in conformation, and ability to modulate the immune system. In view of the foregoing, several reports have been made for preparing molecular constructs with a fixed number of effector elements or with two or more different kinds of functional elements (e.g., at least one targeting element and at least one effector element). However, it is often difficult to build a molecular construct with a particular combination of the targeting and effector elements either using chemical synthesis or recombinant technology. Accordingly, there exists a need in the related art to provide novel molecular platforms to build a more versatile molecule suitable for covering applications in a wide range of diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

<I> Peptide Core-Based Multi-Arm Linkers

In the first aspect, the present disclosure is directed to a linker unit that has at least two different functional elements linked thereto. For example, the linker unit may have linked thereto two different effector elements, one targeting element and one effector element, or one effector element and a polyethylene glycol (PEG) chain for prolonging the circulation time of the linker unit. The present linker unit is designed to have at least two different functional groups such that the functional elements can be linked thereto by reacting with the respective functional groups. Accordingly, the present linker unit can serve as a platform for preparing a molecular construct with two or more functional elements.

According to various embodiments of the present disclosure, the linker unit comprises a center core and a plurality of linking arms. The center core is a polypeptide core comprising (1) a plurality of lysine (K) resides, in which each K residue and a next K residue are separated by a filler sequence comprising glycine (G) and serine (S) residues, and the number of K residues ranges from 2 to 15; or (2) the sequence of $(X_{aa}-K)_n$, where $X_{aa}$ is a PEGylated amino acid having 2 to 12 repeats of ethylene glycol (EG) unit, and n is an integral from 2 to 15. Optionally, the filler sequence consists of 2 to 20 amino acid residues. In various embodiments, the filler sequence may have the sequence of GS, GGS, GSG, or SEQ ID NOs: 1-16. According to some embodiments of the present disclosure, the center core comprises 2-15 units of the sequence of $G_{1-5}SK$; preferably, the center core comprises the sequence of $(GSK)_{2-15}$. Each of the linking arms is linked to the K residues of the center core via forming an amide linkage between the K residue and the linking arm. The linking arm linked to the center core has a maleimide group at its free-terminus. Also, the amino acid residue at the N- or C-terminus of the center core has an azide group or an alkyne group; alternatively or additionally, the amino acid residue at the N- or C-terminus of the center core is a cysteine (C) residue, in which the thiol group of the amino acid residue is linked with a coupling arm having an azide group, an alkyne group, a tetrazine group or a strained alkyne group at the free terminus of the coupling arm.

In some embodiments, the linking arm is a PEG chain, preferably having 2 to 20 repeats of EG units. Also, the coupling arm is a PEG chain, preferably having 2 to 12 repeats of EG units.

Regarding amino acid residues having the azide group, non-limiting examples of said amino acid residues include L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, and 6-azido-D-lysine. As to the amino acid residues having the alkyne group, illustrative examples thereof include L-ho- mopropargylglycine (L-HPG), D-homopropargylglycine (D-HPG), and beta-homopropargylglycine (β-HPG).

When the amino acid residues at the N- or C-terminus of the center core is the cysteine residue, the strained alkyne group at the free terminus of the coupling arm may be, a cyclooctene group, such as trans-cyclooctene (TCO) group; or a cyclooctyne group, e.g. dibenzocyclooctyne (DBCO), difluorinated cyclooctyne (DIFO), bicyclononyne (BCN), or dibenzocyclooctyne (DICO) group. Alternatively, the tetrazine group at the free terminus of the coupling arm includes, but is not limited to, 1,2,3,4-tetrazine, 1,2,3,5-tetrazine, and 1,2,4,5-tetrazine, and derivatives thereof, such as, 6-methyl tetrazine.

According to various embodiments of the present disclosure, the linker unit further comprises a plurality of first elements. Each of the first elements is linked to one of the linking arms via thiol-maleimide reaction. According to various optional embodiments of the present disclosure, the first element is an effector element suitable for eliciting an intended effect (e.g., a therapeutic effect) in a subject. Alternatively, the first element may be a targeting element for directing the linker unit to the site of interest.

Still optionally, the linker unit further comprises a second element that is different from the first elements. In some embodiments, the second element has an azide or alkyne group, so that it is linked to the center core or the coupling arm by coupling with the corresponding alkyne or azide group of the center core or the coupling arm in the presence of Cu(I) as a catalyst in a reaction referred to as "Cu(I) azide-alkyne click chemistry (CuAAC) reaction." Alternatively, in some embodiments, the second element having an azide or cyclooctyne group is linked to the center core or the coupling arm by coupling with the corresponding cyclooctyne or azide group of the center core or the coupling arm via "strain-promoted azide-alkyne click chemistry (SPAAC) reaction". Still alternatively, in certain embodiments, the second element having a tetrazine or cyclooctene group is linked to the center core or the coupling arm by coupling with the corresponding cyclooctene or tetrazine group of the center core or the coupling arm via "inverse electron demand Diels-Alder (iEDDA) reaction". In optional embodiments of the present disclosure, when the first element is an effector element, then the second element may be another effector element, which works additively or synergistically with or independently of the first element; alternatively, the second element may be a targeting element or an element for improving the pharmacokinetic property of the linker unit, such as solubility, clearance, half-life, and bioavailability. In some other optional embodiments, when the first element is the targeting element, then the second element is preferably an effector element or an element for improving the pharmacokinetic property of the linker unit.

In certain embodiments, the linker unit further comprises an optional third element that is different from the first and second elements. In the case where the second element is directly linked to the center core, the other terminus (i.e., the free terminus that is not linked with the second element) of the center core is optionally a cysteine residue, which can be used to introduce an optional third element. Specifically, the thiol group of the cysteine residue is reacted with a maleimide group of a PEG chain; and the thus-linked PEG chain is designated as the coupling arm, which has a tetrazine group or a strained alkyne group at its free terminus. Accordingly, the third element is then linked to the coupling arm via iEDDA reaction. In the case where the linker unit comprises both the second and third elements, it is preferable that at least one of the first and second elements is an effector as described above, while the third element may be the element for improving the pharmacokinetic property of the linker unit. One example of the element for improving the pharmacokinetic property is a long PEG chain having a molecular weight of about 20,000 to 50,000 daltons.

<II> Uses of Peptide Core-Based Multi-Arm Linkers

The linker unit according to the first aspect of the present disclosure may find its utility in clinical medicine for the treatment of various diseases. Hence, the second aspect of the present disclosure is directed to a method for treating these diseases. According to various embodiments of the present disclosure, the method for treating a particular disease includes the step of administering to the subject in need thereof a therapeutically effective amount of the linker unit according to the above-mentioned aspect and embodiments of the present disclosure. As could be appreciated, said linker unit may be administered in a pharmaceutical formulation, which comprises a pharmaceutically-acceptable excipient suitable for the intended or desired administration route, in addition to the present linker unit.

Various illustrative combinations of the first and second elements of the present linker unit for treating some particular diseases are disclosed below for facilitating the understanding of some embodiments of the present disclosure.

According to some embodiments of the present disclosure, the present molecular construct is useful in treating an immune disorder, in which the first element is a single-chain variable fragment (scFv) specific for a cytokine or a receptor of the cytokine; or a soluble receptor of the cytokine, while the second element is an scFv specific for a tissue-associated extracellular matrix protein. In these cases, the first element is an effector element for treating one or more immune disorders, while the second element is a targeting element that facilitates the delivery of the linker unit to the disease site.

Non-limiting examples of the cytokine include tumor necrosis factor-α (TNF-α), interleukin-17 (IL-17), IL-1, IL-6, shared protein of IL-12 and IL-23, and B cell activating factor (BAFF), while non-limiting examples of the cytokine receptor is the receptor specific for IL-6 (i.e., IL-6R) or IL-17 (i.e., IL-17R). As for the soluble receptor of a cytokine, examples of which include, but are not limited to, the soluble receptor of the cytokine specific for TNF-α or IL-1. Illustrative examples of the tissue-associated extracellular matrix protein include, but are not limited to, α-aggrecan, collagen I, collagen II, collagen III, collagen V, collagen VII, collagen IX, and collagen XI.

According to some specific but illustrative examples of linker units suitable for treating psoriasis, the first element is an scFv specific for TNF-α, shared protein of IL-12 and IL-23, IL-17, or IL-17R; and the second element is an scFv specific for collagen I or collagen VII.

In some optional examples, the linker units suitable for treating immune disorders such as systemic lupus erythematosus (SLE), cutaneous lupus or Sjogren's syndrome comprises an scFv specific for BAFF as the first element and an scFv specific for collagen I or collagen VII as the second element.

For treating rheumatoid arthritis, psoriatic arthritis, or ankylosing spondylitis, the illustrative linker units comprises the first element, which is an scFv specific for TNF-α, IL-1, IL-6, shared protein of IL-12 and IL-23, IL-17, IL-6R, or IL-17R; and the second element, which is an scFv specific for collagen II, collagen IX, collagen XI, or α-aggrecan.

The linker units are also suitable for treating inflammatory bowel diseases, e.g., Crohn's disease and ulcerative colitis, among others. In these cases, the present linker unit uses an scFv specific for TNF-α as the first element, and an scFv specific for collagen III or collagen V as the second element.

Another set of diseases treatable by the present linker unit is diffused tumor, including, but not limited to, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma. In these embodiments, the first element may be a targeting element such as an scFv specific for a first cell surface antigen, whereas the second element may be an effector element such as an scFv specific for a second cell surface antigen.

The first cell surface antigen suitable for use as the targeting element for treating diffused tumors includes, but is not limited to, CD5, CD19, CD20, CD22, CD23, CD27, CD30, CD33, CD34, CD37, CD38, CD43, CD72a, CD78, CD79a, CD79b, CD86, CD134, CD137, CD138, and CD319. On the other hand, non-limiting examples of the second cell surface antigen suitable for use as the effector element include CD3 and CD16a.

For the treatment of B-lymphocyte-derived lymphoma or leukemia, the illustrative first element is an scFv specific for CD5, CD19, CD20, CD22, CD23, CD30, CD37, CD79a, or CD79b, while the illustrative second element is an scFv specific for CD3 or CD16a.

To treat plasmacytoma or multiple myeloma, the illustrative first element is an scFv specific for CD38, CD78, CD138, or CD319, while the illustrative second element is an scFv specific for CD3 or CD16a.

Regarding T-cell derived lymphoma or leukemia, the illustrative first element for the treatment thereof is an scFv specific for CD5, CD30, or CD43, while the second element is an scFv specific for CD3 or CD16a.

For treating myelogenous leukemia, the illustrative first element is an scFv specific for CD33 or CD34, while the illustrative second element is an scFv specific for CD3 or CD16a.

Still another set of diseases that may be treated by the present linker unit is solid tumor, including, but not limited to, melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, and head and neck squamous cell carcinoma. Additionally, the present linker unit is also suitable for treating advanced, malignant, or metastatic solid tumors.

To construct a linker unit for treating solid tumors, the first element (i.e., the targeting element) is chosen from a peptide hormone, a growth factor, and a first scFv specific for a tumor-associated antigen; whereas the second element (i.e., the effector element) is a second scFv specific for a cell surface antigen.

For example, the peptide hormone is secretin, cholecystokinin (CCK), somatostatin, or thyroid-stimulating hormone (TSH). Regarding the growth factor, it may be the epidermal growth factor (EGF), mutant EGF, epiregulin, heparin-binding epidermal growth factor (HB-EGF), vascular endothelial growth factor A (VEGF-A), basic fibroblast growth factor (bFGF), or hepatocyte growth factor (HGF). Illustrative examples of the tumor-associated antigen include human epidermal growth factor receptor 1 (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM). As to the cell surface antigen, it can be CD3 or CD16a.

In some instances, the tumor-associated antigen may be shed from the solid tumor of a subject and wanders into his/her circulation system. In these cases, the present method for treating solid tumor comprises the step of, (a) subjecting the subject to a blood dialysis procedure using an antibody specific for one or more tumor-associated antigens to remove the tumor-associated antigens that are shed from the tumor and wanders into the circulation of the subject; and (b) administering the present linker unit for treating the solid tumor.

Yet another representative disease treatable by the present linker unit is osteoporosis. Illustrative linker units suitable for treating osteoporosis include a first element (in this case, an effector element) that is a first scFv specific for ligand of receptor activator of nuclear factor κB (RANKL); and a second element (or a targeting element) that is a second scFv specific for collagen I or osteonectin.

Age-related macular degeneration (AMD) is another example of the diseases treatable by the present linker unit. Illustrative linker units suitable for treating AMD include a first element of an scFv specific for VEGF-A, and a second element of a long PEG chain having a molecular weight of about 20,000 to 50,000 daltons. In this case, the first element is the effector element for treating AMD, while the second element is used to enhance the pharmacokinetic property of the linker unit.

BRIEF DESCRIPTION OF THE DRAWINGS

The present description will be better understood from the following detailed description read in light of the accompanying drawings briefly discussed below.

Figure 1A:
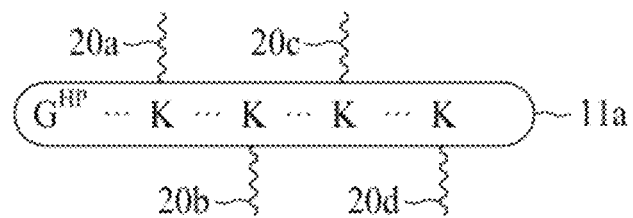
FIG. 1A to FIG. 1K are schematic diagrams illustrating linker units according to certain embodiments of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts, where possible.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to molecular constructs, in which each molecular construct comprises a targeting element (T) and an effector element (E), and these molecular constructs are sometimes referred to as "T-E molecules", "T-E pharmaceuticals" or "T-E drugs" in this document.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing immune responses, exerting cytotoxic effects and the like) or other functional activity (e.g., recruiting other hapten tagged therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphoramide, carbomate, hydroxylate, and the like).

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2-(CH_2CH_2O)_n-COOH$. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" as used herein is defined as a molecule that elicits an immune response. This immune response may involve a secretory, humoral and/or cellular antigen-specific response. In the present disclosure, the term "antigen" can be any of a protein, a polypeptide (including mutants or biologically active fragments thereof), a polysaccharide, a glycoprotein, a glycolipid, a nucleic acid, or a combination thereof.

In the present specification and claims, the term "antibody" is used in the broadest sense and covers fully assembled antibodies, antibody fragments that bind with antigens, such as antigen-binding fragment (Fab/Fab'), F(ab')$_2$ fragment (having two antigen-binding Fab portions linked together by disulfide bonds), variable fragment (Fv), single chain variable fragment (scFv), bi-specific single-chain variable fragment (bi-scFv), nanobodies, unibodies and diabodies. "Antibody fragments" comprise a portion of an intact antibody, preferably the antigen-binding region or variable region of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes.

The term "specifically binds" as used herein, refers to the ability of an antibody or an antigen-binding fragment thereof, to bind to an antigen with a dissociation constant (Kd) of no more than about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, and/or to bind to an antigen with an affinity that is at least two-folds greater than its affinity to a nonspecific antigen.

The term "immune disorder" as used herein refers to a disorder involving deficiency of humoral immunity, deficiency of cell-mediated immunity, combined immunity deficiency, unspecified immunity deficiency, and autoimmune disease.

The term "tumor" as used herein, refers to all neoplastic cell growth and proliferation, whether malignant or benign, and all pre-cancerous and cancerous cells and tissues. In the present specification and claims, the term "tumor" comprises solid tumors and diffused tumors.

The term "solid tumor" as used herein, denotes an abnormal mass of tissue that usually does not contain cysts or liquid areas. Different types of solid tumors are named for the type of cells that form them. Examples of solid tumors include, but are not limited to, sarcomas and carcinomas. Generally, "sarcomas" are cancers arising from connective or supporting tissues such as bone or muscle. "Carcinomas" are cancers arising from glandular cells and epithelial cells, which line body tissues.

The term "diffused tumor" as used herein refers to leukemia and/or hematological malignancy that is formed from hematopoietic (blood-forming) cells and affect blood, bone marrow, or lymph nodes. The example of the diffused tumor includes, but is not limited to, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma.

The term "tumor-associated antigen" (TAA) as used herein refers to any cancer antigen that is known in the art and includes antigens found on the cancer cell surface, as well as those that are shed from cancerous cell and become soluble (i.e., soluble cancer antigens). Several cell surface antigens disposed on tumors or normal cells have soluble counterparts. Such antigens include, but are not limited to those found on cancer-associated fibroblasts (CAFs), tumor endothelial cells (TEC) and tumor-associated macrophages (TAM).

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present molecular construct that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

The present disclosure is based, at least on the construction of the T-E pharmaceuticals that can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

Diseases that can Benefit from Better Drug Targeting

Drugs used for many diseases can be improved for better efficacy and safety, if they can be targeted to the disease sites, i.e., if they can be localized or partitioned to the disease sites more favorably than the normal tissues or organs. Following are primary examples of diseases, in which drugs can be improved if they can be preferentially distributed to the disease sites or cells.

I Immune Disorder

According to the design of molecular constructs of the present disclosure, the diseases, conditions, and/or disorders treatable with the present method is an immune disorder; for example, an autoimmune disorder that includes, but is not limited to, psoriasis, systemic lupus erythematosus (SLE), cutaneous lupus, Sjogren's syndrome, rheumatoid arthritis, psoriatic arthritis, ankylosing spondylitis, and inflammatory bowel disease.

Most of the autoimmune diseases, such as rheumatoid arthritis, systemic lupus erythematosus, Sjögren's syndrome, psoriasis, Crohn's disease, inflammatory bowel diseases, and others affect connective tissues. Regardless of the etiological nature, whether it is environmental, genetic, epigenetic, or their combinations, the affected tissues are damaged by prolong inflammatory processes. It is rationalized in this invention that in bringing anti-inflammatory therapeutic agents, such as anti-TNF-α, anti-IL-17, anti-BAFF, anti-IL-6, anti-IL-12/IL-23, to the diseased connective tissues, the components of the extracellular matrix may be employed as target antigens. The target antigens that may be considered include the various types of collagens, laminins, elastins, fibrillins, fibronectins, and tenascins. Connective tissues fill in nearly all parts of the human body.

However, due to the structural and functional requirements of the connective tissues in different locations, the types of those extracellular matrix components are different, providing excellent choices for target tissue specificity.

The advantages of choosing extracellular components over cell surface antigens for targeting the anti-inflammatory therapeutic agents are that the choices of selectivity among the various types of matrix proteins and the abundant amounts of the extracellular matrix proteins. Furthermore, because cells are not used as antigenic targets, the potential harmful effects of direct binding to cells by anti-inflammatory agents can be avoided.

I-(i) Rheumatoid Arthritis, Psoriatic Arthritis, or Ankylosing Spondylitis

Several antibodies against TNF-α, e.g., infliximab and adalimumab, and fusion proteins of TNF-α receptor and IgG.Fc (e.g. etanercept) are approved or in human clinical trials for use to treat rheumatoid arthritis, ankylosing spondylitis, and other autoimmune diseases. The extracellular portion of the receptor for interleukin-1 (IL-1), anakinra, is approved for treating rheumatoid arthritis. Antibodies against the shared p40 protein of IL-12 and IL-23, e.g., ustekinumab and briakinumab, are approved for psoriatic arthritis or in trials for rheumatoid arthritis. An antibody against IL-6 receptor (tocilizumab) is approved for rheumatoid arthritis and systemic juvenile idiopathic arthritis, and several antibodies against IL-6, e.g., sarilumab and olokizumab, are in clinical trials for treating rheumatoid arthritis. An antibody specific for IL-17 (secukinumab) is approved for psoriasis and in clinical trials for rheumatoid arthritis and ankylosing spondylitis.

While those therapeutic agents can alleviate severe symptoms better than previously available medications, they cause a range of serious side effects in some treated patients. For example, infliximab can cause serious blood disorders, like leukopenia and thrombocytopenia, serious infections, lymphoma and other solid tumors, reactivation of hepatitis B and tuberculosis, and other serious problems. Anakinra causes frequent infections, and severe side effects on the gastrointestinal and the respiratory tracts and the blood forming organs. It is important that the serious side effects of these widely used therapeutic agents be minimized, while retaining or even enhancing their therapeutic effects.

In rheumatoid arthritis, joints of the knees, fingers, toes, and other joints are affected, and in ankylosing spondylitis, joints of the spine and the sacroiliac joint of the pelvis are affected. In the diseased joints, the surface of the bones and the articular cartilage lining the bone surfaces are attacked by the inflammatory immune components in the joints. The articular cartilage in the joints is a smooth cartilage that contains an extracellular matrix. The cartilage is avascular and approximately 60% of the weight is water and the remaining content is composed of collagens and α-aggrecan, a proteoglycan, and other matrix molecules. Collagen II forms the major fibril in the cartilage. Aggrecan is the second most abundant component in the cartilage. Collagen XI is bound to the surface of the collagen II fibril helping to form fibril networks and collagen IX is associated with collagen II and collagen XI. The cartilage has a large surface and the α-aggrecan has a structure and shape like a feather. In addition to the cartilage formation, the joints have also ligaments, which connect adjacent bones, such as the cruciate ligaments, and tendons, which connect muscles to the bones. The ligaments and tendons are formed by fibrous network of collagen types I, II, and III, and elastin and fibrillins 1 and 2.

The present invention rationalizes that the antagonist for TNF-α, IL-1, and shared protein of IL-12 and IL-23 can be carried to the diseased joints by using antibody fragments, such as scFv, specific for collagen II, α-aggrecan, collagen XI or collagen IX, or alternatively, collagen I, elastin or fibrillin 1 as the targeting agent. A preferred anti-collagen II antibody is one that binds to native collagen II in the joints and does not bind to N-terminal and C-terminal propeptides, which are cleaved off during fibril assembly. A preferred anti-aggrecan antibody is one that binds to whole native α-aggrecan molecules and does not bind to fragments that are cleaved off and released into the blood circulation. By adopting the present molecular construct with scFv of anti-collagen II as targeting agent, in comparison with regular IgG against TNF-α, IL-1, and shared protein of IL-12 and IL-23, larger proportions of the present therapeutic agents can be carried to the diseased sites and less amounts of the therapeutic agents will be present in other irrelevant, normal tissues, especially, lymphoid organs, and hence fewer side effects will occur.

I-(ii) Psoriasis

Most patients with psoriasis or plaque psoriasis present inflammatory symptoms primarily in the skin and not in other tissues and organs. Psoriasis involves mainly keratinocytes in part of skin in the affected patients. A systematic administration of monoclonal antibodies anti-TNF-α, anti-IL-12/IL-23, and anti-IL-17 or anti-IL-17 receptor (anti-IL-17R) or other anti-inflammatory agents, such as anti-IL-6, causes unwanted side effects, as discussed in the preceding section. The serious adverse side effects of all these immune modulating antibodies have been well documented.

A number of membrane or extracellular proteins, such as filaggrin, collagen I, which are expressed at much higher levels in the skin tissues than most of other tissues, probably can be considered as the target proteins to shuffle therapeutic agents to the skin. Filaggrin is present in the tight junction between cells and is probably accessible by antibodies in the diseased tissue sites. While collagen I is also present in the bone matrix and many parts of the body, it is present in the dermis layer of the skin in abundant proportions.

For damping the inflammatory activity caused by the diseased keratinocytes, which manifests psoriatic symptoms, it is not necessary to deliver the anti-inflammatory antibody drugs to be in contact with the keratinocytes. The keratinocytes are in the outmost, epidermis layer of the skin; blood vessels, sweat glands, and collagen fibers are in the middle dermis layer of the skin. The inner layer is hypodermis, where adipose tissues are. The three layers of human skin together are 2-3 mm thick. If the anti-inflammatory antibodies are delivered to the dermis layer by scFv specific for collagen I, they can diffuse into the other layers. Or, the antibodies can trap inflammatory cytokines in the three layers of the skin.

Several proteins present at the dermo-epidermal junction may also be employed as targets for carrying therapeutic agents to the skin. These include type VII collagen, type XVII collagen, and laminins type 5, 6, or 10. The dermo-epidermal junction is the area of tissue that joins the epidermal and dermal layers of the skin. The basal cells in the stratum basale of epidermis connect to the basement membrane by the anchoring filament of hemidesmosomes. The cells of the papillary layer of the dermis are attached to the basement membrane by anchoring fibrils, which consist of type VII collagen. Type XVII collagen, a transmembrane protein (also referred to as BP180) expressed on keratinocytes, is a structural component of hemidesmosomes, multiprotein complexes at the dermal-epidermal basement membrane zone that mediate adhesion of keratinocytes to the underlying membrane. Laminins are structural non-collagenous glycoproteins present in basement membranes. Among the many types of laminins, types 5, 6, and 10 are specific of the basal lamina present under stratified epithelia.

I-(iii) Systemic Lupus Erythematosus (SLE), Cutaneous Lupus, or Sjogren's Syndrome Systemic lupus erythematosus (SLE) is an autoimmune disease involving multiple autoantigens, such as nucleic acids, histones, and other nuclear proteins. Sjögren's syndrome is an autoimmune disease, in which the immune system attacks the exocrine glands, specifically the salivary and lacrimal glands, which produce saliva and tears, respectively, resulting the symptoms of dry eyes and dry mouth, leading to infections and various other problems. Both of these diseases occur 9 times more frequently in women than in men, especially in women of child-bearing ages 15 to 35. SLE is a systemic autoimmune connective tissue disease and affects many organs and tissues. In general, those tissues and organs, such as the heart, lungs, bladder, and kidneys, which exhibit elasticity and can expand and contract, contain collagen network. In several types of SLE, cutaneous manifestation of inflammatory symptoms is prominent.

For more than 50 years, not a single new therapeutic agent had been developed for SLE, until belimumab, a human monoclonal antibody specific for BAFF was developed and approved. However, the therapeutic effect of belimumab for SLE has been considered to be marginal. Belimumab causes a host of side effects, including more incidences of serious infections and deaths in the treatment group than the placebo group. Interestingly, in a phase II trial on Sjögren's syndrome, belimumab showed more successful results than in SLE.

In addition to BAFF, researchers have been searching other therapeutic targets for SLE. While not a single inflammatory cytokine has been identified as mainly responsible for the pathological process in SLE, the expression of a group of genes known as downstream events of type 1 interferon stimulation, which is termed "type 1 interferon signature", has been documented in many studies. The pathogenesis of SLE has been found to be associated with the activation of toll-like receptors 7 and 9 (TLR 7 and TLR9), which induce the expression of a group of genes similar to that resulting from the activation by IFN-α.

Several monoclonal antibodies specific for IFN-α, including rontalizumab, sifalimumab, and anifrolumab have been studied in clinical trials for the treatment of SLE. Since IFN-α is involved in many functions, a systemic administration of an antibody against IFN-α without localized targeting to disease sites may render serious side effects.

I-(iv) Inflammatory Bowel Disease

Anti-TNF-α (such as adalimumab) has also been approved for treating Crohn's disease and ulcerative colitis (a form of inflammatory bowel disease). However, as described in an earlier section, the administration of anti-TNF-α is associated with a range of series side effects, including severe infectious diseases and B cell lymphoma. Therefore, in treating patients with Crohn's disease or ulcerative colitis with anti-TNF-α, it will be desirable to distribute the administered anti-TNF-α in favor of the intestine and colon. It has been found collagen III and type V are relatively abundant in the connective tissues in the intestine and bowel.

II Tumor

Several classes of large numbers of therapeutic agents have been developed and experimented in animal models and in human clinical trials for the treatment of malignant tumors, including diffused and solid tumors and primary and metastatic tumors of varying clinical stages. These therapeutic agents, some of which have been approved by governmental regulatory agencies for use in patients, include (1) a large number of compounds targeting key cellular regulatory pathways or structural components, or damaging DNA or important cellular machinery, (2) antibodies specific for surface antigens of certain cell types or specific for certain tumor-associated antigens and capable of mediating apoptosis, antibody-dependent cellular cytotoxicity (ADCC), or complement-mediated cytolysis (CMC) of the targeted cells, (3) antibodies specific for certain tumor-associated antigens, which are conjugated with potent cytotoxic drugs, (4) immunoregulatory cytokines, such as interferon-α (IFN-α), interleukin-2 (IL-2), or interferon-γ (IFN-γ), which can activate the immune system in fighting against malignant cells, (5) antibodies targeting certain cell surface markers of B and T lymphocytes, e.g., anti-CD20 rituximab, (6) antibodies targeting growth factor receptors, e.g., anti-HER2/Neu trastuzumab and anti-EGFR cetuximab, (7) antibodies targeting vascular endothelial growth factor-A (VEGF-A) for inhibiting angiogenesis, e.g., bevacizumab, and (8) antibodies binding to immune checkpoints, such as PD1 (programmed cell death protein 1, CD279), e.g., nivolumab, PD-L1 (programmed cell death protein ligand 1, CD274), e.g., MPDL3280A, CTLA-4 (cytotoxic T-lymphocyte protein 4, CD152), e.g., ipilimumab, which inhibit the negative feedback of immune reactions and allow continual activation of on-going immune responses.

The usefulness of therapeutic agents for treating cancer as well as for many other diseases is limited or compromised by their toxicity, because the agents also act on some normal cells to some degrees. Therefore, many therapeutic agents have limited therapeutic windows and therefore, in order to control their toxic effects, they are administered in many of the treated patients at suboptimal doses, as far as therapeutic efficacy is concerned, which are insufficient to achieve satisfactory therapeutic effects.

The antibody-drug conjugate approach, which is being pursued actively, requires that the tumor-targeting antibodies together with the carried cytotoxic drugs be internalized by the targeted cells expressing the tumor-associated antigens, which the targeting antibodies recognize. This requirement may potentially limit the power of the current antibody-drug conjugate approach, because cells in a tumor express a tumor-associated antigen at varying densities. Those cells expressing relatively low levels may not be killed by the current antibody-drug conjugates during treatment and will grow up as the therapeutic agents are discontinued.

II-(i) Diffused Tumor

II-(i)-A Targeting Cancerous Cells Originated from Leukocytes

The cancer derived from malignantly transformed cells of the lymphoid and myeloid lineages account for a significant proportion among all cancer. Those tumors are generally diffusive and not solid. Thus, the targeting of leukocyte-derived tumors will involve the targeting of the individual tumor cells. Therefore, the identification of the expression of cell-surface antigens of the tumor cells is a key in the targeting of leukocyte-derived tumors.

Tumors derived from white blood cells (leukocytes) are generally classified into three categories: (1) leukemia found in the blood and bone marrow, (2) lymphoma found in the lymphatic system, and (3) myeloma in many parts of bone marrow and also in the blood.

Leukemia has four broad classifications: (1) acute lymphocytic leukemia (ALL), (2) chronic lymphocytic leukemia (CLL), (3) acute myelogenous leukemia (AML), and (4) chronic myelogenous leukemia (CML). However, as advanced diagnostic and analytic methods are being developed, new types of leukemia, such as B cell CLL, T cell CLL, B cell prolymphocytic leukemia, Hairy cell leukemia, and others are been defined.

Lymphomas are divided into two categories: (1) Hodgkin lymphomas and (2) non-Hodgkin lymphomas. Of the patients who have lymphomas, about 12% have Hodgkin lymphomas and the rest have non-Hodgkin lymphomas. Of the non-Hodgkin lymphomas, most are B cell-derived and there are many subtypes of B cell non-Hodgkin lymphomas. The rest of the non-Hodgkin lymphomas are T cell lymphomas.

Myeloma is derived from antibody-producing plasma cells and is also referred to as plasmacytoma. Myeloma cells are found in bone marrow and can travel in the blood circulation and establish growth in many parts of the bone and hence myeloma is also called multiple myeloma.

While leukemia, lymphomas, and myeloma are derived from myeloid, lymphoid, and plasma cells, the diagnosis of the tumor types is often very complex, involving tissue and cellular examinations with histological, immunohistological, morphological, and cellular marker analyses of the biopsied tumor samples. Since the pluripotent stem cells, the myeloid lineage, which differentiate into granulocytes (neutrophils, eosinophils, and basophils), monocytes and macrophages, and platelets, and the lymphoid lineage, which differentiate into B cells and T cells, undergo many steps of differentiation and maturation, the malignant transformation can occur at any of the differentiation stages. Furthermore, the cancerous transformation may augment and gain certain traits and reduce or lose certain traits.

The surface markers or differentiation antigens, especially those, which have been assigned a CD (cluster of differentiation) number, have become very useful and often necessary to identify the various leukocytes and immunocytes in the studies of innate and adaptive immunity. Often the identification of a cell type requires a set of markers.

For antibody-based therapeutic approaches for targeting cancer of the leukocyte origin, identification of the surface markers of a targeted tumor is very useful and powerful. However, among the patients who have been diagnosed to have the same type of tumor, the surface markers can vary over a large range in terms of density.

II-(i)-B Surface Markers on B Cell-Derived Lymphocytic Leukemia and Lymphoma

Both ALL and CLL are not solid tumors. ALL is derived from lymphoblasts, precursor B cells, precursor T cells, or B cells. ALL consists of the immunophenotypic subtypes: (1) precursor B cell acute lymphoblastic leukemia, which expresses cell surface markers associated with B cell precursors and precursor T cell acute lymphoblastic leukemia, which express markers of precursor T cells, (2) Burkitt's lymphoma, which is derived from B cells of the germinal center and express cell surface markers associated with B cells, and (3) acute biphenotypic leukemia, which express markers of both lymphoid and myeloid cells.

CLL is also referred to as B-cell CLL (B-CLL), because CLL is mostly derived from B cells. Thus, the major difference of the cellular origin between ALL and CLL is that ALL is derived from lymphoblasts, which are the common precursors of B cells and T cells and CLL is derived from B cells. All CLL cells in a patient are from monoclonal, derived original one B cell of a particular set of $V_H$ and $V_L$. The cells of CLL express CD19 and CD20, and characteristically CD5 and CD23.

Hodgkin lymphomas are characterized by the presence of Reed-Sternberg cells, which are multi-nucleated giant cells derived from B cells. There are at least four subtypes of Hodgkin lymphomas based on the morphology of Reed-Sternberg cells and the composition of reactive cell infiltrate in the lymph node biopsy specimen: (1) nodular sclerosing Hodgkin lymphoma, (2) mixed-cellularity, (3) lymphocyte-rich or lymphocytic predominance, and (4) lymphocyte depleted. It is well established that Hodgkin lymphoma is derived from mature B cells. Cells of Hodgkin lymphoma, depending on its immunophenotype, express a subset of CD15, CD20, CD30, CD79a, and CD138. Most of the cases of non-Hodgkin lymphomas are derived from B cells. There are at least 14 subtypes of B-cell non-Hodgkin lymphomas.

B lymphocytes are the source of antigen-specific antibodies and are a critical component of the adaptive immune system for the defense against infectious pathogens. However, B cells can also be pathogenic and the cause of several types of diseases. B-cell disorders are divided into undesired immunoglobulin production (autoimmune and allergic diseases) and uncontrolled proliferation (lymphomas, leukemia). B cells have proven to be effective targets for the treatment of multiple autoimmune disorders and B-lineage cancer. Many approaches pertaining to B-cell depletion for the treatment of B cell malignancies and antibody-mediated diseases have been developed with partial success or are in active experimental stages. These include therapeutic antibodies that target human B-cell surface antigens, such as CD19, CD20, CD22, CD37, CD79a/CD79b, and isotype-specific Ig receptor. Some of such antibodies can cause lysis of B cells. Some other antibodies will cause B cell lysis when the antibodies are conjugated with cytotoxic drugs.

Multiple myeloma, also referred to as plasma cell myeloma, is the second most common hematological malignancies (after non-Hodgkin lymphoma), constituting 1% of all cancers and 2% of all cancer deaths. Multiple myeloma produces large quantities of myeloma proteins and occupies bone marrow and manifests a series of symptoms, including bone pain, anemia, renal failure, infection, and neurological problems. Multiple myeloma is derived from the malignant transformation of plasma cells, which differentiate from B lymphocytes. However, cells of multiple myeloma do not express the most common B cell markers, such as CD19, CD20, and CD22.

A number of therapies and drugs have been experimented and a few have been approved for the treatment of multiple myeloma. These include corticosteroids, chemotherapies, proteasome inhibitors, and immunoregulatory compounds.

II-(i)-C Unique B Cell Antigens Igα, Igβ and Migis-δ as Targets of Antibodies

Igα (CD79a)/Igβ (CD79b) is set of antigens that are expressed in association of the B cell receptor (BCR) complex on the surface of cells of the B-cell lineage. Igα/Igβ is a heterodimeric transmembrane protein, which is composed of two distinct chains Igα and Igβ stabilized by disulfide bonding. Igα/Igβ forms a complex with the BCR and generates a signal following recognition of antigen by the BCR complex. During the development of B cell maturation, Igα/Igβ is expressed in the pre-B-cell stage and is early than CD20 for the expression pattern on the B-cell lineage. Igα/Igβ has been considered as attractive target for the B cell depletion therapy in the treatment of non-Hodgkin lymphomas because Igα/Igβ is expressed on B cells and on most non-Hodgkin lymphomas.

The mIgD and mIgM are coexpressed on the surface of mature B cells and function as part of BCR. The mIgD contains a unique migis-δ peptide segment of 27 AA, which represents the extracellular portions of the membrane-anchoring segment of mIgD and is located between the CH3 domain and transmembrane segment. It has been proposed that migis-δ peptide provides an antigenic site for targeting mIgD-expressing B cells. The site is present on the mIgD-expressing B cells and not on the secreted IgD.

I-(i)-D T Cell Tumors

T lymphocyte subsets through their surface molecules and secreted factors mediate a complex network of immunoregulatory activities on humoral and cellular immune effector functions, including the production of different classes of antibodies, the secretion of various cytokines, and the generation of cytotoxic T cells and other cytolytic cells. Many autoimmune diseases are caused by the abnormal activities of T cells against self-components or cells. For example, in type-I diabetes, the insulin-producing β cells in the islets of Langerhans of pancreas are attacked and killed by autoimmune T cells. The devastating autoimmune diseases, such as systemic lupus erythematosus (SLE), multiple sclerosis, and inflammatory bowel diseases, are caused mainly by T cells. Furthermore, the rejection reaction toward organ or tissue transplants is mediated mainly by T cells.

There are also a few forms of T cell malignancy. Thus, modulating T cell activities or removing T cells has been an active area of drug discovery research. A variety of antibodies and their modified forms against T cell surface antigens, including CD3, CD4, CD8, CD25, and CD28 have been studied in animal models or human clinical trials for treating various human diseases mentioned above. Some antibodies with or without the conjugation with cytotoxic drugs can cause the lysis of the targeted T cell subsets. Some antibodies can cause anergy or an idled, inactive state of T cells without actually lysing the cells.

T lymphocytes play major roles in regulating activities of various immunocytes and various other cell types in adaptive and native immunity. In the development of therapeutic agents to target lymphocytes, fewer candidates have been successfully developed for targeting T cells than for targeting B cells. However, there have been increasing numbers of therapeutic antibodies that are being developed to target surface antigens of T cell subsets. Antibodies targeting T cell surface antigens can potentially be employed to treat malignant tumors derived from T cells. Antibodies may also be used to modulate T cell activities, either to inhibit them or to enhance them.

II-(i)-E Myelogenous Leukemia

AML is derived from myeloid stem cells or myeloid blasts, the precursors for the mature granulocytes and monocytes. Many of the subtypes of AML are caused by mutagens, which cause chromosomal translocations or loss of certain gene segments. Cells of AML derived from various differentiation stages express some subsets of surface markers of CD13, CD14, CD15, CD33, CD34, CD36, CD41, CD61, CD64, CD65, and CD11c. Cells of AML derived from the early precursor myeloid stages express CD34, which is a surface marker of pluripotent stem cells, and CD33, which is a marker of immature myeloid cells. Cells of AML derived from many myeloid differentiation stages express CD15, a marker of mature myeloid cells. CML is a clonal bone marrow stem cell disorder resulted from the malignant transformation of a stem cell or myeloid stem cell, or from the translocation of the Philadelphia chromosome.

II-(ii) Solid Tumor

II-(ii)-A Solid Tumor and Tumor-Associated Antigens

Cells of many types of tumors express certain antigens on cell surface at elevated levels compared to those on normal cells. Those antigens are referred to as tumor-associated antigens. For example, serum samples from patients with pancreatic tumors and many types of gastrointestinal cancer, including colorectal cancer, esophageal cancer, and hepatocellular carcinoma, contain CA19-9 antigen (carbohydrate antigen 19-9, a sialyl-Lewis A antigen). The cells of those tumors express CA19-9 on the extracellular matrix on cell surface. Similarly, serum samples from patients with ovarian cancer, endometrial cancer, fallopian tube cancer, and some other types of cancer have elevated CA-125 (carbohydrate antigen 125, mucin 16) and the cells of those tumors express CA125. Overexpression of cell surface associated glycoprotein mucin 1 (MUC1) is often associated with colon, breast, ovarian, lung, and pancreatic cancer.

The ganglioside GD2 is highly expressed on neuroectoderm-derived tumors and sarcomas, including neuroblastoma, retinoblastoma, melanoma, small cell lung cancer, brain tumors, osteosarcoma, rhabdomyosarcoma, Ewing's sarcoma in children and adolescents, as well as liposarcoma, fibrosarcoma, leiomyosarcoma and other soft tissue sarcoma in adults.

While mesothelin is expressed on normal mesothelial cells, it is expressed on many human cancers, mesothelioma, tumors of the pancreas, ovary, lung, and stomach, cholangiocarcinoma, and triple-negative breast cancer.

Tn antigen is a structural element on glycoproteins, in which N-acetylgalactosamine (GalNAc) is linked to serine or threonine by a glycosidic bond, i.e. as an O-glycan. Addition of single monosaccharide residues creates disaccharide antigens: the Thomsen-Friedenreich antigen (TF antigen or T antigen) is formed by substitution with galactose (Gal(b1-3)GalNAc); the sialyl-Tn antigen (STn antigen) is formed by substitution with sialic acid (Neu5Ac(a2-6)GalNAc. TN and sialy-Tn are not usually found on healthy cell surfaces, but may be found on cancer cells.

Tumor-associated antigens that have been widely studied as markers of tumors or explored as targets for immunological therapies include (1) epidermal growth factor receptors (EGFRs)—human epidermal growth factor 1 (EGFR or HER1), HER2, HER3, HER4, or their mutants; (2) glycoproteins—CA19-9 (bearing Sialyl Lewis$^A$ antigen), CA125 (bearing mucin 16 or MUC 16), cell surface-associated mucin 1 (MUC1), or carcinoembryonic antigen, melanoma-associated antigen (MAGE), prostate-specific membrane antigen (PSMA), prostate stem cell antigen (PSCA), or mesothelin; (3) mucin-related Tn or Sialyl Tn; (4) the blood group Lewis related Lewis", Sialyl Lewis", Sialyl Lewis$^A$, or Lewis$^X$; (5) glycosphingolipids—Globo H or stage-specific embryonic antigen-4 (SSEA-4); or (6) gangliosides—GD2, GD3, GM2, fucosyl GM1, or Neu5GcGM3.

II-(ii)-B Growth Factors, Peptide Hormones, and Cytokines as Targeting Agents for Cells Overexpressing Receptors A number of growth factors, peptide hormones and regulatory cytokines regulate important physiological processes in a human body. These substances mediate their functions through interacting with their receptors on different cell types. The most prominent are endocrine or exocrine cells in organs or compartments or organs bearing function-specific receptors, which respond to growth factors, hormones, or cytokines. For example, the exocrine cells in the pancreas bear receptors that respond to secretin, gastrin, and cholecystokinin (CCK) from duodenum and stomach during food intake and digestive process.

When malignant transformation occurs to the receptor-bearing cells, the tumorous cells maintain the expression of the receptors. In fact, in many cases, an abnormally high expression of the receptors occurs due to certain mutations in the cells, which are not necessarily in the receptors themselves. The affected cells thus become malignantly transformed. The overexpression of receptors on tumors, e.g., somatostatin receptors are strongly expressed on most neuroendocrine tumors, and the targeting of those receptors for therapeutic and diagnostic (e.g., radio-imaging) purposes have been an active area of research. Neuroendocrine tumors are generally rare, but include a long list of tumors of various cell origins, including those of gastroenteropancreatic neuroendocrine tumors, thyroid gland tumors, Merkel cell carcinoma, adrenomedullary tumors, and many others.

Examples of this line of research are numerous. The over-expression of the family of epidermal growth factor receptors (EGFRs) in breast cancer, lung cancer, colon cancer, and many other types of carcinoma is well documented. For example, monoclonal antibody trastuzumab specific for HER2/Neu receptor is broadly used for treating HER2-positive breast cancer. Cetuximab specific for EGFR is being used in treating metastatic colon cancer, metastatic non-small cell lung cancer, and head and neck cancer. Small molecular inhibitors, such as gefitinib and erlotinib, which interrupts the tyrosine kinase domain in EGFR, have also been developed for the treatment of several type of cancer.

Pancreatic cancer is one of the most vicious cancers. Among the various types of pancreatic cancers, the pancreatic (ductal or invasive) adenocarcinoma derived from the exocrine cells account for 85%, although those ductal epithelial cells account only for 10% among all cells in the pancreas. The exocrine cells express receptors for the peptide hormones, gastrin, secretin, or cholecystokinin, which are secreted by the cells in the stomach and duodenum, and respond to those hormones and secrete bicarbonate ions and digestive enzymes. The overexpressed receptors for CCK and gastrin in pancreatic cancer and many other types have also been explored as a target for radioimaging. Other hormones and receptors, which are under active investigation, are somatostatin and gastrin-releasing peptide. In such radio-imaging approaches, CCK or gastrin of their peptide analogues are coupled with chelating groups for radioactive nuclides. In the imaging procedure, the imaging agents bind to the primary or metastasized tumors containing cells expressing the receptors. Peptide hormones or their analogues carrying radionuclides, lutetium-177, yttrium-90, or indium-111, have also been experimented for treating tumors.

II-(ii)-C Immune Checkpoints as Targets

CTLA-4 is a protein receptor that down-regulates the immune system. CTLA-4 is found on the surface of T cells, and acts as an "off" switch when bound to CD80 (B7-1) or CD86 (B7-2) on the surface of antigen presenting cells. Such binding prevents the binding of those receptors by CD28, which activates the immune response. A human IgG1 antibody specific for CTLA-4, ipilimumab, has been approved for treating melanoma and in clinical studies for treating several other types of cancer. The treatment with ipilimumab has been associated with severe and potential fatal immunological side effects due to T cell activation and proliferation.

PD-1 is expressed on the surface of activated T cells. If PD-1 is blocked by its ligand, PD-L1, the T cell becomes inactive. This is a way that the body regulates the immune system to avoid an overreaction of immune responses. Many cancer cells make PD-L1 and thereby disarm the T cells and inhibit them from attacking the cancer cells. Two human antibodies against PD-1, pembrolizumab and nivolumab, have been approved for treating unresectable or metastatic melanoma, which no longer respond to other drugs, and squamous non-small cell lung cancer. An anti-PD-L1 antibody, MPDL3280A, is now in Phase II or III clinical trials for triple-negative breast cancer, metastatic non-small cell lung cancer, bladder carcinoma, and renal cell carcinoma. A large number of anti-PD-1 and anti-PD-L1 antibodies are in research or early clinical trials.

Many researchers are exploring other targets, such as OX40, CD137, and CD27 on the activated T cells and their corresponding ligands, OX40L, CD137L, and CD137 the antigen-presenting cells or tumor cells for releasing the brakes of T cell activation. Those pathways are considered to be milder in T-cell activation strength than the CTLA-4 and PD-1 pathways.

While antibodies specific for PD-1 or PD-L1 look very promising for treating several types of cancer, the current clinical development suggest that those antibodies will require the combination with chemotherapies, other antibodies, or targeted therapies. Also, the antibodies also cause a range of severe side effects. We rationalize that if the antibodies specific for immune checkpoints were carried to the targeted tumor site, better therapeutic efficacy could be achieved, and fewer side effects would occur.

II-(ii)-D Vascular Endothelial Growth Factor as Targets

Vascular endothelial growth factor A (VEGF-A) is essential for angiogenesis (blood vessel formation) as the tumor grows. The blood circulation is required for oxygen and nutrient supplies, waste disposal and many other functions. Antibodies specific for VEGF-A, such as bevacizumab specific for VEGF-A, are effective as a monotherapy or in combination with chemotherapy in treating a few forms of cancer. However, bevacizumab is associated with a range of side effects, including hypertension and heightened risk of bleeding, bowel perforation, and necrotizing fasciitis.

II-(ii)-E Immunoregulatory Cytokines as Cancer Therapeutic Agents

The immunoregulatory cytokines referred to in this invention are those that are known to be stimulatory and are major drivers in activating immune responses. These cytokines include interleukin-2 (IL-2), interferon-$\alpha$ (IFN-$\alpha$), interferon-$\gamma$ (IFN-$\gamma$), and TNF-$\alpha$. Among them, IFN-$\alpha$, which is a strong activator of T cells, has been approved for use in hairy-cell leukemia, AIDS-related Kaposi's sarcoma, follicular lymphoma, chronic myeloid leukemia and melanoma. However, clinical studies so far have not established major therapeutic utilities of those immunoregulatory cytokines in treating tumors, mainly because the therapeutic doses of those cytokines in systematic administrations are limited by the side effects of the cytokines. In general, cytokines act mainly in the microenvironment of the lymphoid system.

III Osteoporosis Disease

An antibody specific for RANKL (CD254), the ligand of RANK (RANK, receptor activator of nuclear factor $\kappa$B), denosumab, is approved for the treatment of osteoporosis. The development of denosumab represents a major advancement in the care for osteoporosis. However, the administration of denosumab causes common side effects, such as infections of the urinary and respiratory tracts, cataracts, constipation, rashes, and joint pain. It is hence desirable that the therapeutic agent is carried preferentially to the bone.

RANKL is a membrane protein, belonging to the tumor necrosis factor ligand family. RANKL is detected at high levels in the lung, thymus, and lymph nodes. It is also detected at low levels in the bone marrow, stomach, peripheral blood, spleen, placenta, leukocytes, heart, thyroid and skeletal muscle. Since IgG anti-RANKL, such as denosumab, can serve a therapeutic agent for osteoporosis, the molecular constructs of this invention should provide as better therapeutic agents than IgG anti-RANKL.

Another target for antibodies for the treatment of osteoporosis is sclerostin, encoded by SOST gene. The glycoprotein is produced and secreted by osteocytes and negatively regulates osteoblastic bone formation. The loss or defective mutation of SOST gene causes progressive bone thickening. A defective mutation in the SOST gene increases bone formation. Antibodies against sclerostin cause increased bone formation, bone mineral density, and stronger bones. The phase I and II clinical trials of two humanized monoclonal antibodies against sclerostin, blosozumab and romosozumab, indicated that the antibody treatment is associated with increased bone mineral density and bone formation and decreased bone resorption.

In light of the foregoing discussion, two types of molecular platforms for constructing the T-E molecules of this invention are provided in the present disclosure. One is based on the "linker unit" configuration (see, Part I to Part IV below), and the other is based on the "Fc" configuration (see, Part V to Part VIII below). Detailed discussion relating to the structure of said two configurations are provided below, as well as the practical applications of each molecular construct.

Part I Peptide Core-Based Multi-Arm Linkers

The first aspect of the present disclosure pertains to a linker unit that comprises, (1) a center core that comprises 2-15 lysine (K) residues, and (2) 2-15 linking arms respectively linked to the K residues of the center core. The present center core is characterized in having or being linked with an azide group, an alkyne group, a tetrazine group, or a strained alkyne group at its N- or C-terminus.

In the preparation of the present linker unit, a PEG chain having a N-hydroxysuccinimidyl (NHS) group at one terminus and a maleimide group at the other terminus is linked to the K residue of the center core by forming an amide bond between the NHS group of the PEG chain and the amine group of the K residue. In the present disclosure, the PEG chain linked to the K residue is referred to as a linking arm, which has a maleimide group at the free-terminus thereof.

According to the embodiments of the present disclosure, the center core is a polypeptide that has 8-120 amino acid residues in length and comprises 2 to 15 lysine (K) residues, in which each K residue and the next K residue are separated by a filler sequence.

According to embodiments of the present disclosure, the filler sequence comprises glycine (G) and serine (S) residues; preferably, the filler sequence consists of 2-15 residues selected from G, S, and a combination thereof. For example, the filler sequence can be,

GS,

GGS,

GSG,

GGGS, (SEQ ID NO: 1)

GSGS, (SEQ ID NO: 2)

GGSG, (SEQ ID NO: 3)

GSGGS, (SEQ ID NO: 4)

SGGSG, (SEQ ID NO: 5)

GGGGS, (SEQ ID NO: 6)

GGSGGS, (SEQ ID NO: 7)

GGSGGSG, (SEQ ID NO: 8)

SGSGGSGS, (SEQ ID NO: 9)

GSGGSGSGS, (SEQ ID NO: 10)

SGGSGGSGSG, (SEQ ID NO: 11)

GGSGGSGGSGS, (SEQ ID NO: 12)

SGGSGGSGSGGS, (SEQ ID NO: 13)

GGGGSGGSGGGGS, (SEQ ID NO: 14)

GGGSGSGSGSGGGS, (SEQ ID NO: 15)

or

SGSGGGGSGGSGSG. (SEQ ID NO: 16)

The filler sequence placed between two lysine residues may be variations of glycine and serine residues in somewhat random sequences and/or lengths. Longer fillers may be used for a polypeptide with fewer lysine residues, and shorter fillers for a polypeptide with more lysine residues. Hydrophilic amino acid residues, such as aspartic acid and histidine, may be inserted into the filler sequences together with glycine and serine. As alternatives for filler sequences made up with glycine and serine residues, filler sequences may also be adopted from flexible, soluble loops in common human serum proteins, such as albumin and immunoglobulins.

According to certain preferred embodiments of the present disclosure, the center core comprises 2-15 units of the sequence of $G_{1-5}SK$. Alternatively, the polypeptide comprises the sequence of $(GSK)_{2-15}$; that is, the polypeptide comprises at least two consecutive units of the sequence of GSK. For example, the present center core may comprises the amino acid sequence of the following, Ac-CGGSGGSGGSKGSGSK, (SEQ ID NO: 17)

Ac-CGGSGGSGGSKGSGSKGSK, (SEQ ID NO: 18)

or

Ac-CGSKGSKGSKGSKGSKGSKGSKGSKGSK, (SEQ ID NO: 19)

in which Ac represents the acetyl group.

According to certain embodiments of the present disclosure, the center core is a polypeptide that comprises the sequence of $(X_{aa}\text{-K})_n$, in which $X_{aa}$ is a PEGylated amino acid having 2 to 12 repeats of ethylene glycol (EG) unit, and n is an integral from 2 to 15.

As described above, the present center core is characterized in having or being linked with an azide group, an alkyne group, a tetrazine group, or a strained alkyne group at its N- or C-terminus. According to some embodiments of the present disclosure, the present center core comprises, at its N- or C-terminus, an amino acid residue having an azide group or an alkyne group. The amino acid residue having an azide group can be, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine. For example, the present center core may have the sequence of, Ac-(GSK)$_{2-7}$-(G$_{2-4}$S)$_{1-8}$-A$^{AH}$,
Ac-A$^{AH}$-(SG$_{2-4}$)$_{1-8}$-(GSK)$_{2-7}$,
Ac-A$^{AH}$-(SG$_{2-4}$)$_{0-7}$-(GSK)$_{2-6}$-(G$_{2-4}$S)$_{1-8}$-C,
Ac-C-(SG$_{2-4}$)$_{0-7}$-(GSK)$_{2-6}$-(G$_{2-4}$S)$_{1-8}$-A$^{AH}$,
Ac-K-(Xaa$_{2-12}$-K)$_{2-4}$-Xaa$_{2-12}$-A$^{AH}$,
Ac-A$^{AH}$-Xaa$_{2-12}$-K-(Xaa$_{2-12}$-K)$_{2-4}$,
Ac-A$^{AH}$-Xaa$_{2-12}$-K-(Xaa$_{2-12}$-K)$_{1-3}$-Xaa$_{2-12}$-C, or
Ac-C-Xaa$_{2-12}$-K-(Xaa$_{2-12}$-K)$_{1-3}$-Xaa$_{2-12}$-A$^{AH}$, in which Xaa is a PEGylated amino acid having specified repeats of EG unit, Ac represents the acetyl group, and A$^{AH}$ represents the AHA residue.

Exemplary amino acid having an alkyne group includes, but is not limited to, L-homopropargylglycine (L-HPG), D-homopropargylglycine (D-HPG), or beta-homopropargylglycine (β-HPG). In this case, the present center core may have the sequence of, Ac-(GSK)$_{2-7}$-(G$_{2-4}$S)$_{1-8}$-G$^{HP}$,
Ac-G$^{HP}$-(SG$_{2-4}$)$_{1-8}$-(GSK)$_{2-7}$,
Ac-G$^{HP}$-(SG$_{2-4}$)$_{0-7}$-(GSK)$_{2-6}$-(G$_{2-4}$S)$_{1-8}$-C,
Ac-C-(SG$_{2-4}$)$_{0-7}$-(GSK)$_{2-6}$-(G$_{2-4}$S)$_{1-8}$-G$^{HP}$
Ac-K-(Xaa$_{2-12}$-K)$_{2-4}$-Xaa$_{2-12}$-G$^{HP}$,
Ac-G$^{HP}$-Xaa$_{2-12}$-K-(Xaa$_{2-12}$-K)$_{2-4}$,
Ac-G$^{HP}$-Xaa$_{2-12}$-K-(Xaa$_{2-12}$-K)$_{1-3}$-Xaa$_{2-12}$-C, or
Ac-C-Xaa$_{2-12}$-K-(Xaa$_{2-12}$-K)$_{1-3}$-Xaa$_{2-12}$-G$^{HP}$, in which Xaa is a PEGylated amino acid having specified repeats of EG unit, Ac represents the acetyl group, and G$^{HP}$ represents the HPG residue.

It is noted that many of the amino acids containing an azide or alkyne group in their side chains and PEGylated amino acids are available commercially in t-boc (tert-butyloxycarbonyl)- or Fmoc (9-fluorenylmethyloxycarbonyl)-protected forms, which are readily applicable in solid-phase peptide synthesis.

According to some working examples of the present disclosure, the center core may comprise the sequence of,

```
                                       (SEQ ID NO: 20)
Ac-G^HP GGSGGSGGSKGSGSK, (SEQ ID NO: 21)
Ac-G^HP GGSGGSGGSKGSGSKGSK, (SEQ ID NO: 22)
Ac-A^AH GGSGGSGGSKGSGSKGSK, (SEQ ID NO: 23)
Ac-G^HP GGSGGSGGSKGSGSKGSGSC, (SEQ ID NO: 24)
Ac-C-Xaa2-K-Xaa2-K-Xaa2-K,
or
                                       (SEQ ID NO: 25)
Ac-C-Xaa6-K-Xaa6-K-Xaa6-K-Xaa6-K-Xaa6-K,
``` in which Xaa is a PEGylated amino acid having specified repeats of EG unit, Ac represents the acetyl group, A$^{AH}$ represents the AHA residue, and G$^{HP}$ represents the HPG residue.

Alternatively, the present center core is linked with a coupling arm, which has a functional group (e.g., an azide group, an alkyne group, a tetrazine group, or a strained alkyne group) at the free-terminus thereof (that is, the terminus that is not linked to the center core). In these cases, the present center core comprises a cysteine residue at its N- or C-terminus. To prepare a linker unit linked with a coupling arm, a PEG chain having a maleimide group at one terminus and a functional group at the other terminus is linked to the cysteine residue of the center core via thiol-maleimide reaction occurred between the maleimide group of the PEG chain and the thiol group of the cysteine residue. In the present disclosure, the PEG chain linked to the cysteine residue of the center core is referred to as the coupling arm, which has a functional group at the free-terminus thereof.

Preferably, the coupling arm has a tetrazine group or a strained alkyne group at the free-terminus thereof. These coupling arms have 2-12 EG units. According to the embodiments of the present disclosure, the tetrazine group is 1,2,3,4-tetrazine, 1,2,3,5-tetrazine, 1,2,4,5-tetrazine, or derivatives thereof. Example of strained alkyne group includes, but is not limited to, trans-cyclooctene (TCO), dibenzocyclooctyne (DBCO), difluorinated cyclooctyne (DIFO), bicyclononyne (BCN), and dibenzocyclooctyne (DICO). According to some embodiments of the present disclosure, the tetrazine group is 6-methyl-tetrazine.

Example of the present center core linked with the coupling arm includes, but is not limited to, Ac-(GSK)$_{2-7}$-(G$_{2-4}$S)$_{1-8}$-C-Xaa$_{2-12}$-tetrazine,
Ac-(GSK)$_{2-7}$-(G$_{2-4}$S)$_{1-8}$-C-Xaa$_{2-12}$-strained alkyne,
Ac-K-(Xaa$_{2-12}$-K)$_{2-4}$-Xaa$_{2-12}$-C-Xaa$_{2-12}$-tetrazine,
Ac-K-(Xaa$_{2-12}$-K)$_{2-4}$-Xaa$_{2-12}$-C-Xaa$_{2-12}$-strained alkyne,
Tetrazine-Xaa$_{2-12}$-C(Ac)-(SG$_{2-4}$)$_{1-8}$-(GSK)$_{2-7}$,
Strained alkyne-Xaa$_{2-12}$-C(Ac)-(SG$_{2-4}$)$_{1-8}$-(GSK)$_{2-7}$,
Tetrazine-Xaa$_{2-12}$-C(Ac)-Xaa$_{2-12}$-K-(Xaa$_{2-12}$-K)$_{2-4}$, and
Strained alkyne-Xaa$_{2-12}$-C(Ac)-Xaa$_{2-12}$-K-(Xaa$_{2-12}$-K)$_{2-4}$.

Alternatively, the center core has an azide or alkyne group at one terminus and a coupling arm with tetrazine or strained alkyne group at the other terminus. Examples are the following:

Ac-A$^{AH}$-(SG$_{2-4}$)$_{0-7}$-(GSK)$_{2-6}$-(G$_{2-4}$S)$_{1-8}$-C-Xaa$_{2-12}$-tetrazine,
Ac-A$^{AH}$-(SG$_{2-4}$)$_{0-7}$-(GSK)$_{2-6}$-(G$_{2-4}$S)$_{1-8}$-C-Xaa$_{2-12}$-strained alkyne,
Tetrazine-Xaa$_{2-12}$-C(Ac)-(SG$_{2-4}$)$_{0-7}$-(GSK)$_{2-6}$-(G$_{2-4}$S)$_{1-8}$-A$^{AH}$,
Strained alkyne-Xaa$_{2-12}$-C(Ac)-(SG$_{2-4}$)$_{0-7}$-(GSK)$_{2-6}$-(G$_{2-4}$S)$_{1-8}$-A$^{AH}$,
Ac-A$^{AH}$-Xaa$_{2-12}$-K-(Xaa$_{2-12}$-K)$_{1-3}$-Xaa$_{2-12}$-C-Xaa$_{2-12}$-tetrazine,
Ac-A$^{AH}$-Xaa$_{2-12}$-K-(Xaa$_{2-12}$-K)$_{1-3}$-Xaa$_{2-12}$-C-Xaa$_{2-12}$-strained alkyne,
Tetrazine-Xaa$_{2-12}$-C(Ac)-Xaa$_{2-12}$-K-(Xaa$_{2-12}$-K)$_{1-3}$-Xaa$_{2-12}$-A$^{AH}$,
Strained alkyne-Xaa$_{2-12}$-C(Ac)-Xaa$_{2-12}$-K-(Xaa$_{2-12}$-K)$_{1-3}$-Xaa$_{2-12}$-A$^{AH}$,
Ac-G$^{HP}$-(SG$_{2-4}$)$_{0-7}$-(GSK)$_{2-6}$-(G$_{2-4}$S)$_{1-8}$-C-Xaa$_{2-12}$-tetrazine,
Ac-G$^{HP}$-(SG$_{2-4}$)$_{0-7}$-(GSK)$_{2-6}$-(G$_{2-4}$S)$_{1-8}$-C-Xaa$_{2-12}$-strained alkyne,
Tetrazine-Xaa$_{2-12}$-C(Ac)-(SG$_{2-4}$)$_{0-7}$-(GSK)$_{2-6}$-(G$_{2-4}$S)$_{1-8}$-G$^{HP}$,
Strained alkyne-Xaa$_{2-12}$-C(AC)-(SG$_{2-4}$)$_{0-7}$-(GSK)$_{2-6}$-(G$_{2-4}$S)$_{1-8}$-G$^{HP}$, Ac-G$^{HP}$-Xaa$_{2-12}$-K-(Xaa$_{2-12}$-K)$_{1-3}$-Xaa$_{2-12}$-C-Xaa$_{2-12}$-tetrazine, Ac-G$^{HP}$-Xaa$_{2-12}$-K-(Xaa$_{2-12}$-K)$_{1-3}$-Xaa$_{2-12}$-C-Xaa$_{2-12}$-strained alkyne, Tetrazine-Xaa$_{2-12}$-C(Ac)-Xaa$_{2-12}$-K-(Xaa$_{2-12}$-K)$_{1-3}$-Xaa$_{2-12}$-G$^{HP}$, and Strained alkyne-Xaa$_{2-12}$-C(Ac)-Xaa$_{2-12}$-K-(Xaa$_{2-12}$-K)$_{1-3}$-Xaa$_{2-12}$-G$^{HP}$.

The polypeptide may also be synthesized using recombinant technology by expressing designed gene segments in bacterial or mammalian host cells. It is preferable to prepare the polypeptide as recombinant proteins if the core has high numbers of lysine residues with considerable lengths. As the length of a polypeptide increases, the number of errors increases, while the purity and/or the yield of the product decrease, if solid-phase synthesis was adopted. To produce a polypeptide in bacterial or mammalian host cells, a filler sequence ranges from a few amino acid residues to 10-20 residues may be placed between two K residues. Further, since AHA and HPG are not natural amino acids encoded by the genetic codes, the N-terminal or C-terminal residue for those recombinant polypeptides is cysteine. After the recombinant proteins are expressed and purified, the terminal cysteine residue is then reacted with short bifunctional cross-linkers, which have maleimide group at one end, which reacts with SH group of cysteine residue, and alkyne, azide, tetrazine, or strained alkyne at the other end.

The synthesis of a polypeptide using PEGylated amino acids involves fewer steps than that with regular amino acids such as glycine and serine resides. In addition, PEGylated amino acids with varying lengths (i.e., numbers of repeated ethylene glycol units) may be employed, offering flexibility for solubility and spacing between adjacent amino groups of lysine residues. Other than PEGylated amino acids, the center cores may also be constructed to comprise artificial amino acids, such as D-form amino acids, homo-amino acids, N-methyl amino acids, etc. Preferably, the PEGylated amino acids with varying lengths of polyethylene glycol (PEG) are used to construct the center core, because the PEG moieties contained in the amino acid molecules provide conformational flexibility and adequate spacing between conjugating groups, enhance aqueous solubility, and are generally weakly immunogenic. The synthesis of PEGylated amino acid-containing center core is similar to the procedures for the synthesis of regular polypeptides.

Optionally, for stability purpose, the present center core has an acetyl group to block the amino group at its N-terminus.

As could be appreciated, the number of the linking arms linked to the center core is mainly determined by the number of lysine resides comprised in the center core. Since there are at least two lysine residues comprised in the present center core, the present linker unit may comprise a plurality of linking arms.

Reference is now made to FIG. 1A. As illustrated, the linker unit 10A comprises a center core 11a comprising one HPG (G$^{HP}$) residue and four lysine (K) residues respectively separated by filler sequences (denoted by the dots throughout the drawings). The filler sequences between the HPG residue and K residue or between any two K residues may comprise the same or different amino acid sequences. In this example, four linking arms 20a-20d are linked to the lysine residues by forming an amide linkage between the NHS group and the amine group of the lysine residue, respectively. As could be appreciated, certain features discussed above regarding the linker unit 10A or any other following linker units are common to other linker units disclosed herein, and hence some or all of these features are also applicable in the following examples, unless it is contradictory to the context of a specific embodiment. However, for the sake of brevity, these common features may not be explicitly repeated below.

Figure 1B:
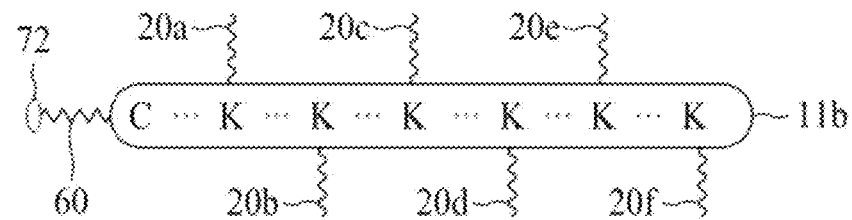

FIG. 1B provides a linker unit 10B according to another embodiment of the present disclosure. The center core 11b comprises one cysteine (C) residue and six lysine (K) residues respectively separated by the filler sequences. In this example, the linker unit 10B comprises six linking arms 20a-20f that are respectively linked to the lysine residues. According to the embodiments of the present disclosure, the linking arm is a PEG chain having 2-20 repeats of EG units.

Unlike the linker unit 10A of FIG. 1A, the linker unit 1B further comprises a coupling arm 60. As discussed above, a PEG chain having a maleimide group at one end and a functional group at the other end is used to form the coupling arm 60. In this way, the coupling arm 60 is linked to the cysteine residue of the center core 11b via thiol-maleimide reaction. In this example, the functional group at the free terminus of the coupling arm 60 is a tetrazine group 72. According to the embodiments of the present disclosure, the coupling arm is a PEG chain having 2-12 repeats of EG units.

When the release of effector elements at the targeted site is required, a cleavable bond can be installed in the linking arm. Such a bond is cleaved by acid/alkaline hydrolysis, reduction/oxidation, or enzymes. One embodiment of a class of cleavable PEG chains that can be used to form the coupling arm is NHS-PEG$_{2-20}$-S—S-maleimide, where S—S is a disulfide bond that can be slowly reduced, while the NHS group is used for conjugating with the amine group of the center core, thereby linking the PEG chain onto the center core. The maleimide group at the free terminus of the linking arm may be substituted by an azide, alkyne, tetrazine, or strained alkyne group.

According to certain embodiments of the present disclosure, the linking arm that is linked to the K residue of the center core has a maleimide group at its free terminus. In this way, a functional element (such as, a targeting element or an effector element) having a thiol group may react with the maleimide group of the linking arm via the thiol-maleimide reaction so that the functional element is linked to the linking arm. For the sake of illustration, the functional elements linked to the linking arms are referred to as the first elements. As could be appreciated, the number of the first elements carried by the present linker unit depends on the number of K residues of the center core (and thus, the number of the linking arms). Accordingly, one of ordinary skill in the art may adjust the number of the first elements of the linker unit as necessary, for example, to achieve the desired targeting or therapeutic effect.

Figure 1C:
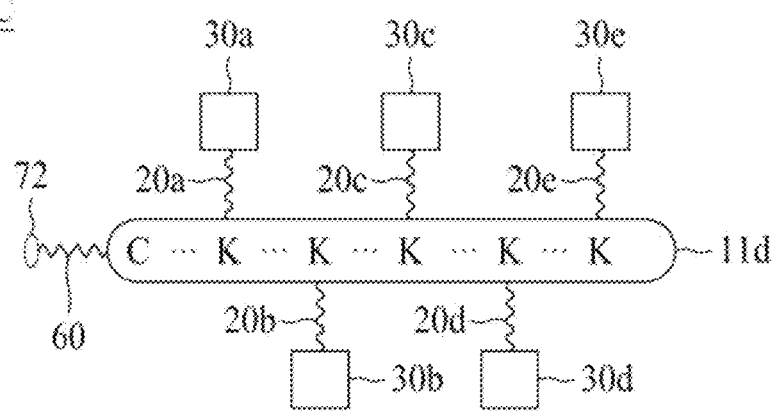

An example of a linker unit 10C having the first elements is illustrated FIG. 1C. Other than the features disused hereafter, FIG. 1C is quite similar to FIG. 1B. First, there are five K residues in the center core 11d, and accordingly, five linking arms 20a-20e are linked thereto, respectively. Second, the linker unit 10C has five first elements 30a-30e linked to each of the linking arms 20a-20e. As disused below, the optional tetrazine group 72 allows for the conjugation with an additional functional element, another molecular construct (see, Part III or Part VII below).

In order to increase the intended or desired effect (e.g., the therapeutic effect), the present linker unit may further comprise a second element in addition to the first element. For example, the second element can be either a targeting element or an effector element. In optional embodiments of the present disclosure, the first element is an effector element, while the second element may be another effector element, which works additively or synergistically with or independently of the first element. Still optionally, the first and second elements exhibit different properties; for example, the first element is a targeting element, and the second element is an effector element, and vice versa. Alternatively, the first element is an effector element, and the second element is an element capable of improving the pharmacokinetic property of the linker unit, such as solubility, clearance, half-life, and bioavailability.

According to one embodiment of the present disclosure, the first element is the targeting element that renders the present linker unit specifically target to a lesion site, the second element is the effector element that elicits a therapeutic effect once the present linker unit is delivered to the lesion site. For example, in the treatment of diffused tumor, the present linker unit may comprise a plurality of targeting elements as the first elements and one effector element as the second element. In this case, the targeting element specifically targets the cell surface antigen expressed on the diffused tumor (e.g., CD5, CD19, CD20, CD22, CD23, CD30, CD37, CD79a, or CD79b); while the effector element (e.g., the antibody fragment specific for CD3 or CD16a) recruits T cells or NK cells to kill the tumor cells.

According to an alternative embodiment of the present disclosure, the first element is the effector element and the second element is the targeting element. For example, in the treatment of autoimmune disease, the present linker unit may comprise one targeting element that specifically targets the tissue-associated extracellular matrix protein (e.g., α-aggrecan, collagen I, collagen II, collagen III, collagen V, collagen VII, collagen IX, and collagen XI) and a plurality of effector elements that produce an therapeutic effect on the lesion site.

Structurally, the second element is linked to the azide, alkyne, tetrazine, or strained alkyne group at the N- or C-terminus of the center core. Specifically, the second element may be optionally conjugated with a short PEG chain (preferably having 2-12 repeats of EG units) and then linked to the N- or C-terminal amino acid residue having an azide group or an alkyne group (e.g., AHA residue or HPG residue). Alternatively, the second element may be optionally conjugated with the short PEG chain and then linked to the coupling arm of the center core.

According to some embodiments of the present disclosure, the center core comprises an amino acid having an azide group (e.g., the AHA residue) at its N- or C-terminus; and accordingly, a second element having an alkyne group is linked to the N- or C-terminus of the center core via the CuAAC reaction. According to other embodiments of the present disclosure, the center core comprises an amino acid having an alkyne group (e.g., the HPG residue) at its N- or C-terminus; and a second element having an azide group is thus capable of being linked to the N- or C-terminus of the center core via the "Copper(I)-catalyzed alkyne-azide cycloaddition (CuAAC)" reaction (or the "click" reaction for short) as exemplified in Scheme 1.

<<Scheme 1 CuAAC reaction>>

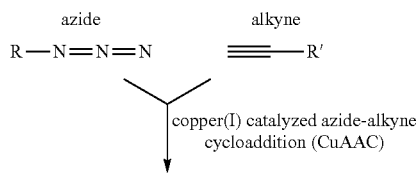

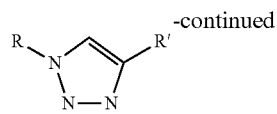

The CuAAC reaction yields 1,5-disubstituted 1,2,3-triazole. The reaction between alkyne and azide is very selective and there are no alkyne and azide groups in natural biomolecules. Furthermore, the reaction is quick and pH-insensitive. It has been suggested that instead of using copper (I), such as cuprous bromide or cuprous iodide, for catalyzing the click reaction, it is better to use a mixture of copper (II) and a reducing agent, such as sodium ascorbate to produce copper (I) in situ in the reaction mixture. Alternatively, the second element can be linked to the N- or C-terminus of the present center core via a copper-free reaction, in which pentamethylcyclopentadienyl ruthenium chloride complex is used as the catalyst to catalyze the azide-alkyne cycloaddition.

Figure 1D:
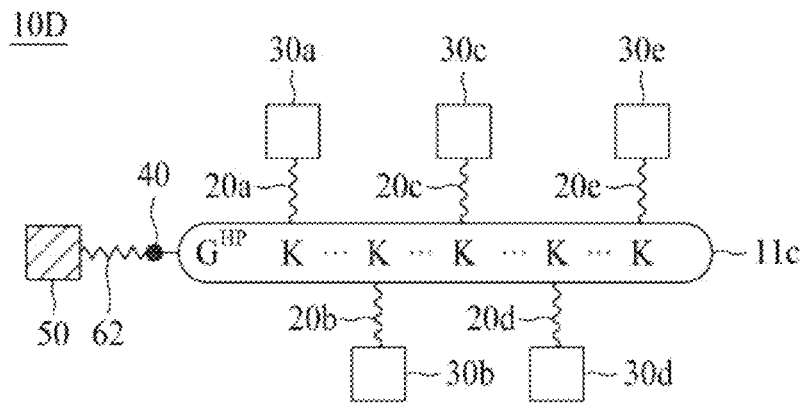

FIG. 1D provides an example of the present linker unit 10D carrying a plurality of first elements and one second element. In this example, the center core 11c comprises one HPG ($G^{HP}$) residue and five lysine (K) residues. Five linking arms 20a-20e are respectively linked to the five K residues of the center core 11c; and five first elements 30a-30e are respectively linked to said five linking arms 20a-20e via the thiol-maleimide reaction. In addition to the first elements, the linker unit 10D further comprises one second element 50 that is linked to one end of a short PEG chain 62. Before being conjugated with the center core 11c, the other end of the short PEG chain 62 has an azide group. In this way, the azide group may reacted with the HPG residue that having an alkyne group via CuAAC reaction, so that the second element 50 is linked to the center core 11c. The solid dot 40 depicted in FIG. 1D represents the chemical bond resulted from the CuAAC reaction occurred between the HPG residue and the azide group.

Alternatively, the second element is linked to the center core via a coupling arm. According to certain embodiments of the present disclosure, the coupling arm has a tetrazine group, which can be efficiently linked to a second element having a TCO group via the inverse electron demand Diels-Alder (iEDDA) reaction (see, scheme 2). According to other embodiments of the present disclosure, the coupling arm has a TCO group, which is capable of being linked to a second element having a tetrazine group via the iEDDA reaction. In the iEDDA reaction, the strained cyclooctenes that possess a remarkably decreased activation energy in contrast to terminal alkynes is employed, and thus eliminate the need of an exogenous catalyst.

Figure 1E:
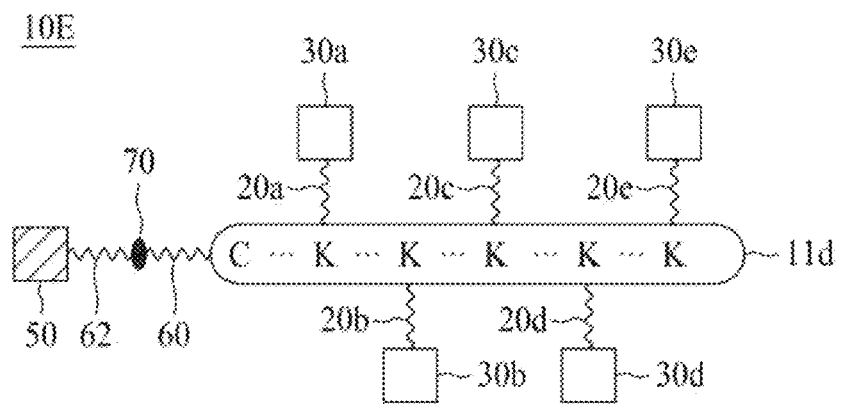

Reference is now made to FIG. 1E, in which the center core 11d of the linker unit 10E comprises a terminal cysteine (C) residue and five lysine (K) residues. As depicted in FIG. 1E, five linking arms 20a-20e are respectively linked to the five K residue of the center core 11d, and then five first elements 30a-30e are respectively linked to the five linking arms 20a-20e via thiol-maleimide reactions. The cysteine residue is linked to the coupling arm 60, which, before being conjugated with the second element, comprises a tetrazine group or a TCO group at its free-terminus. In this example, a second element 50 linked with a short PEG chain 62 having a corresponding TCO or tetrazine group can be linked to the coupling arm 60 via the iEDDA reaction. The ellipse 70 as depicted in FIG. 1E represents the chemical bond resulted from the iEDDA reaction occurred between the coupling arm 60 and the short PEG chain 62.

<<Scheme 2 iEDDA Reaction>>

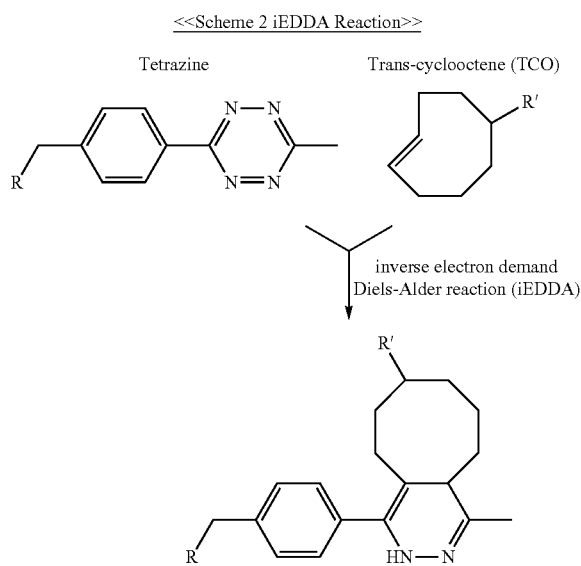

According to other embodiments of the present disclosure, before the conjugation with a second element, the coupling arm has an azide group. As such, the coupling arm can be linked to the second element having a strained alkyne group (e.g., the DBCO, DIFO, BCN, or DICO group) at the free-terminus of a short PEG chain via SPAAC reaction (see, scheme 3), and vice versa.

Figure 1F:
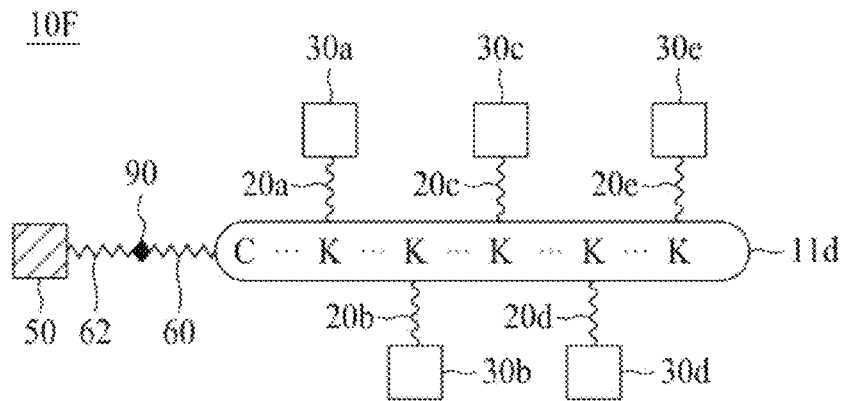

Reference is now made to FIG. 1F, in which the linker unit 10F has a structure similar to the linker unit 10E of FIG. 1E, except that the coupling arm 60 comprises an azide or a strained alkyne group (e.g., the DBCO, DIFO, BCN, or DICO group), instead of the tetrazine or TCO group. Accordingly, the second element 50 linked with a short PEG chain 62 may have a corresponding strained alkyne (e.g., DBCO, DIFO, BCN, or DICO) or azide group, so that it can be linked to the coupling arm 60 via the SPAAC reaction. The diamond 90 as depicted in FIG. 1F represents the chemical bond resulted from the SPAAC reaction occurred between the coupling arm 60 and the short PEG chain 62.

<<Scheme 3 SPAAC reaction>>

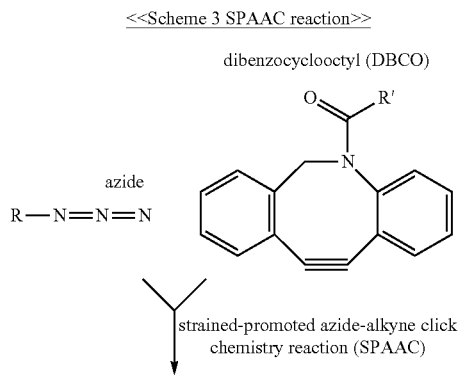

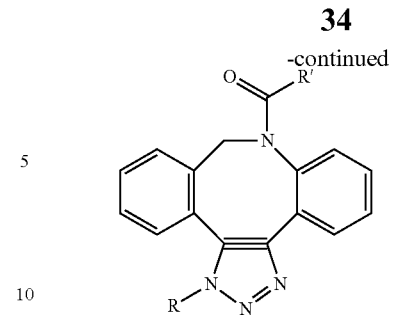

Scheme 4 is an exemplary illustration of the process of preparing the present linker unit. In step 1, the center core comprising the amino acid sequence of (GSK)$_3$ and a L-azidohomoalanine (AHA) residue at the C-terminus thereof is prepared. In step 2, three linking arms are respectively linked to the lysine (K) residues of the center core via forming an amide bond between the NHS group and the amine group; the linking arm linked to the center core has a maleimide (Mal) group at the free-terminus thereof. In step 3, three anti-A antigen scFvs (scFv αA) as the first element are respectively linked to the linking arms via the thiol-maleimide reaction. Meanwhile, in step 4, one anti-B antigen scFv (scFv αB) as the second element is linked with a short PEG chain that has 4 repeats of EG units and a DBCO group at the free terminus. Finally, in step 5, the second element is linked to the AHA residue of the center core via the SPAAC reaction.

<<Scheme 4 Preparation of linker unit linked with two different scFvs via linking arm and C-terminal amino acid residue>>

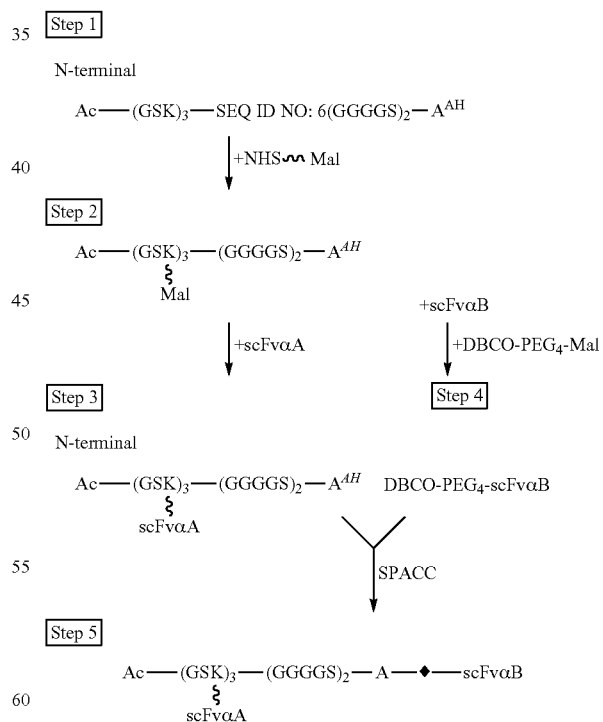

Scheme 5 illustrates another example of the process for preparing the present linker unit. In step 1, the center core comprising the amino acid sequence of (K-Xaa)$_3$ and a cysteine residue at the C-terminus thereof is prepared. In step 2, a PEG chain (as the coupling arm) that has the maleimide (Mal) group at one terminus and a tetrazine group at the other terminus is linked to the cysteine residue via the thiol-maleimide reaction. Then, in step 3, three linking arm are respectively linked to the lysine (K) residues of the center core. Next, three anti-A antigen scFvs (scFv αA) as the first elements are respectively linked to the linking arms via the thiol-maleimide reaction as described in step 4. Meanwhile, in step 5, one anti-B antigen scFv (scFv αB) as the second element is linked with a short PEG chain that has 3 repeats of EG units and a TCO group at the free terminus. Finally, in step 6, the second element is linked to the coupling arm via the iEDDA reaction.

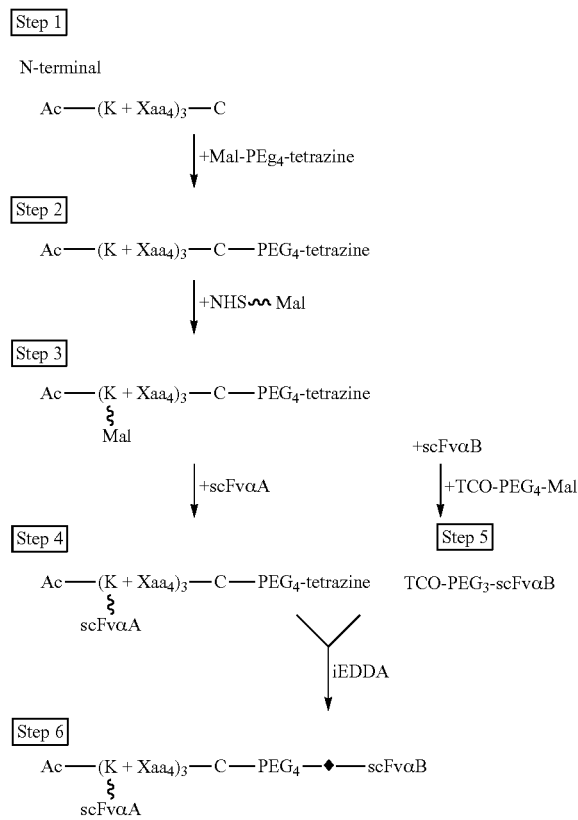

<<Scheme 5 Preparation of linker unit linked with two different scFvs via linking arm and coupling arm>>

PEGylation is a process, in which a PEG chain is attached or linked to a molecule (e.g., a drug or a protein). It is known that PEGylation imparts several significant pharmacological advantages over the unmodified form, such as improved solubility, increased stability, extended circulating life, and decreased proteolytic degradation. According to one embodiment of the present disclosure, the second element is a PEG chain, which has a molecular weight of about 20,000 to 50,000 daltons.

Figure 1G:
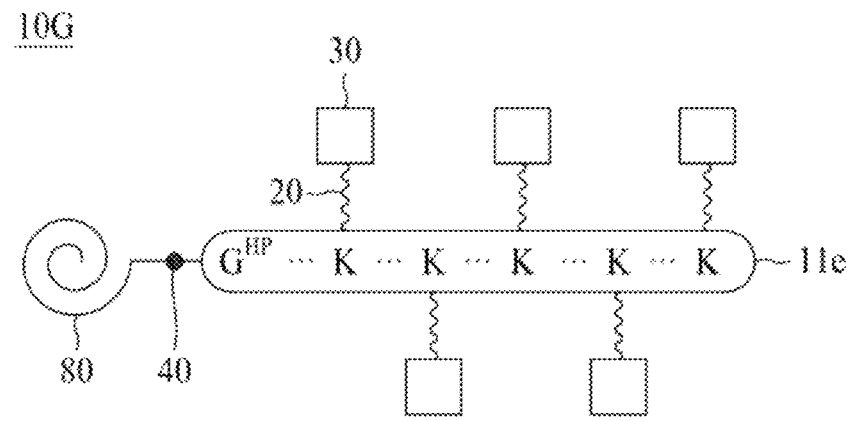

FIG. 1G provides an alternative example of the present linker unit (linker unit 10G), in which five first elements 30 are respectively linked to the lysine residues via the linking arms 20 and the HPG ($G^{HP}$) residue of the center core Ile is linked with a PEG chain 80 via the CuAAC reaction. The solid dot 40 depicted in FIG. 1G represents the chemical bond resulted from the CuAAC reaction occurred between the AHA residue and the PEG chain 80.

Figure 1H:
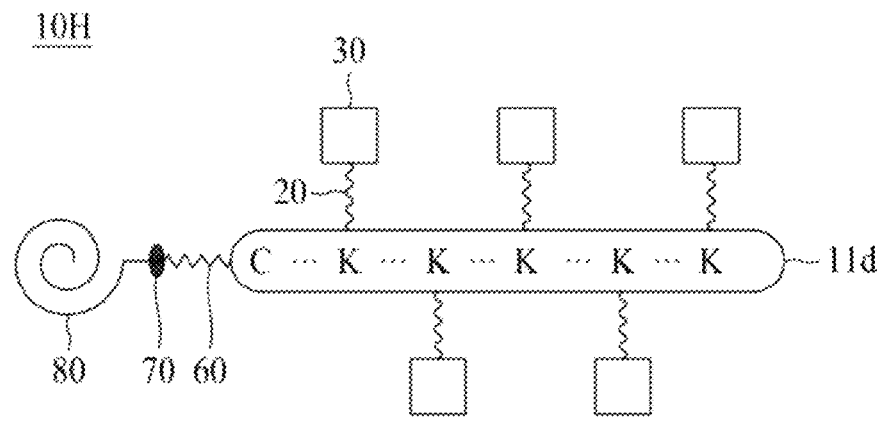

FIG. 1H provides another example of the present disclosure, in which the N-terminus of the center core 13d is a cysteine residue that is linked to a coupling arm 60. A PEG chain 80 can be efficiently linked to the coupling arm 60 via the iEDDA reaction. The ellipse 70 of the linker unit 10H represents the chemical bond resulted from the iEDDA reaction occurred between the coupling arm 60 and the PEG chain 80.

Figure 1I:
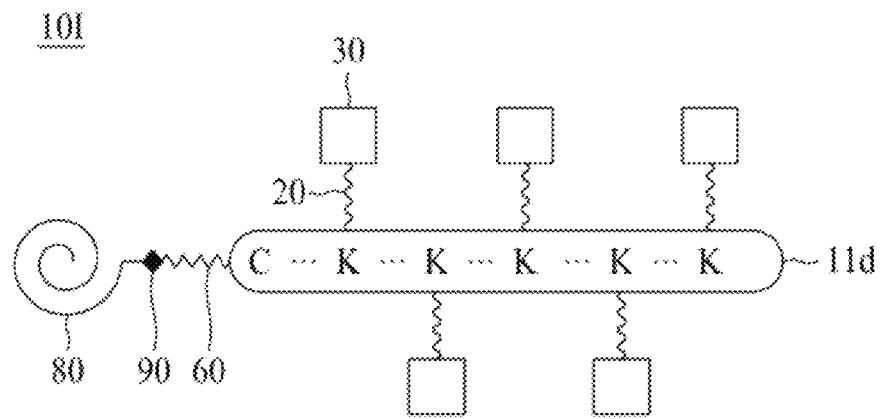

FIG. 1I provides an alternative example of the present linker unit, in which the linker unit 10I has a structure similar to the linker unit 10H of FIG. 1H, except that the PEG chain 80 is linked to the coupling arm 60 via the SPAAC reaction. The diamond 90 depicted in FIG. 1I represents the chemical bond resulted from the SPAAC reaction occurred between the coupling arm 60 and the PEG chain 80.

According to some embodiments of the present disclosure, in addition to the first and second elements, the present linker unit further comprises a third element. In this case, one of the N- and C-terminus of the center core is an amino acid having an azide group or an alkyne group, while the other of the N- and C-terminus of the center core is a cysteine residue. The lysine residues of the center core are respectively linked with the linking arms, each of which has a maleimide group at its free terminus; whereas the cysteine residue of the center core is linked with the coupling arm, which has a tetrazine group or a strained alkyne group at its free terminus. As described above, the first element is therefore linked to the linking arm via the thiol-maleimide reaction, and the second element is linked to the coupling arm via the iEDDA reaction. Further, a third element is linked to the terminal amino acid having an azide group or an alkyne group via the CuAAC reaction or SPAAC reaction.

Optionally, the first, second, and third elements are different. According to one embodiment of the present disclosure, the linker unit may have two different kinds of targeting elements and one kind of effector element, two different kinds of effector elements and one kind of targeting element, or one kind of targeting element, one kind of effector element, and one element capable of improving the pharmacokinetic property of the linker unit, such as solubility, clearance, half-life, and bioavailability.

Figure 1J:
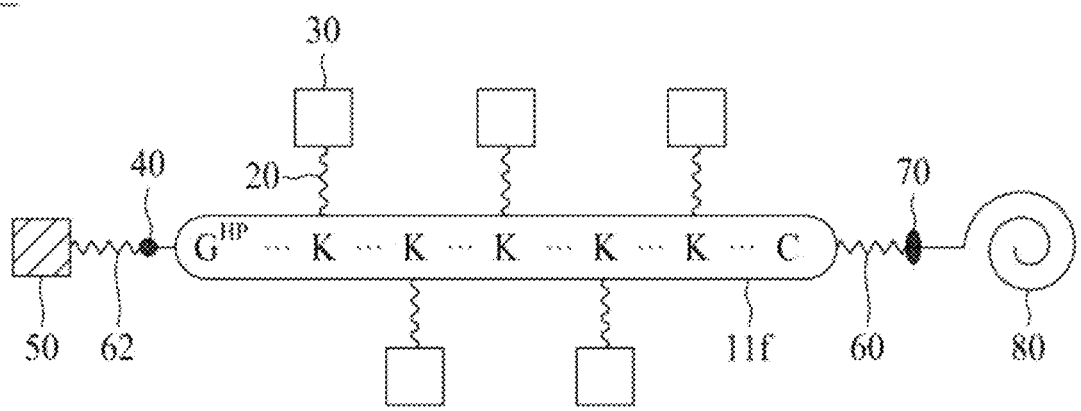

Reference is now made to the linker unit 10J of FIG. 1J, in which the center core 11f has an HPG ($G^{HP}$) residue at the N-terminus thereof and a cysteine residue at the C-terminus thereof. The linking arms 20 and the coupling arm 60 are respectively linked to the lysine (K) residues and the cysteine (C) residue of the center core 11f. Further, five first elements 30 are respectively linked to the five linking arms 20, the second element (i.e., the PEG chain) 80 is linked to the coupling arm 60, and the third element 50 is linked to the HPG residue via the short PEG chain 62. The solid dot 40 indicated the chemical bond resulted from the CuAAC reaction occurred between the HPG residue and the short PEG chain 62; while the ellipse 70 represents the chemical bond resulted from the iEDDA reaction occurred between the coupling arm 60 and the PEG chain 80.

Figure 1K:
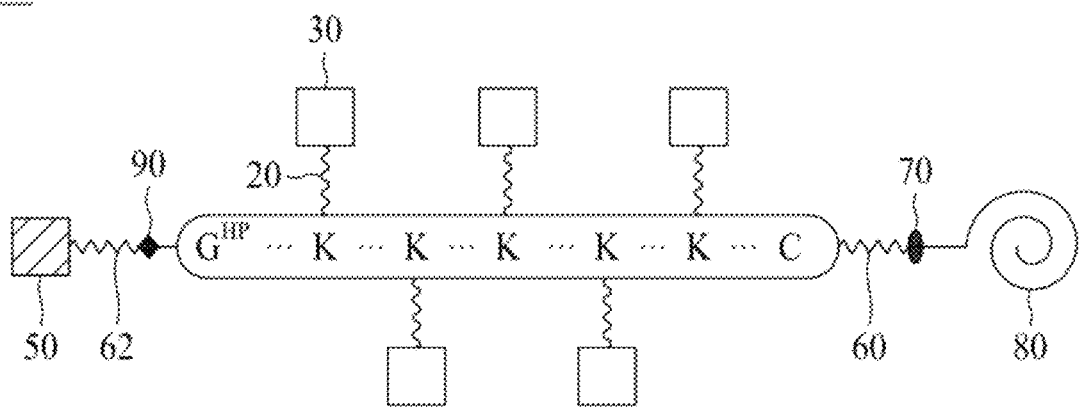

FIG. 1K provides another embodiment of the present disclosure, in which the linker unit 10K has the similar structure with the linker unit 10J of FIG. 1J, except that the short PEG chain 62 is linked with the HPG residue via the SPAAC reaction, instead of the iEDDA reaction. The diamond 90 in FIG. 1K represents the chemical bond resulted from the SPAAC reaction occurred between the short PEG chain 62 and the HPG residue.

In the preferred embodiments of this disclosure, the linking arms have a maleimide group in the free terminus for conjugating with first elements having the sulfhydryl group via the thiol-maleimide reaction. Also, there is one cysteine residue or an amino acid residue with an azide or alkyne group at a terminus of the peptide core for attaching a coupling arm for linking a second element.

It is conceivable for those skilled in the arts that variations may be made. A conjugating group, other than maleimide, such as azide, alkyne, tetrazine, or strained alkyne may be used for the free terminus of the linking arms, for linking with first elements with a CuAAC, iEDDA, or SPAAC reaction. Also the cysteine residue (or an amino acid residue with an azide or alkyne group) of the peptide core needs not to be at the N- or C-terminus. Furthermore, two or more of such residues may be incorporated in the peptide core to attach multiple coupling arms for linking a plurality of second elements.

Part II Uses of Peptide Core-Based Multi-Arm Linkers

Compared with previously known therapeutic constructs, the present linker unit discussed in Part I is advantageous in two points:

(1) The number of the functional elements may be adjusted in accordance with the needs and/or applications. The present linker unit may comprise two elements (i.e., the first and second elements) or three elements (i.e., the first, second, and third elements) in accordance with the requirements of the application (e.g., the disease being treated, the route of administration of the present linker unit, and the binding avidity and/or affinity of the antibody carried by the present linker unit). For example, when the present linker unit is directly delivered into the tissue/organ (e.g., the treatment of eye), one element acting as the effector element may be enough, thus would eliminate the need of a second element acting as the targeting element. However, when the present linker unit is delivered peripherally (e.g., oral, enteral, nasal, topical, transmucosal, intramuscular, intravenous, or intraperitoneal injection), it may be necessary for the present linker unit to simultaneously comprise a targeting element that specifically targets the present linker unit to the lesion site; and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described in Part I of the present disclosure, the number of the first element may vary with the number of lysine residue comprised in the center core. If the number of lysine residue in the center core ranges from 2 to 15, then at least two first elements may be comprised in each linker unit. Thus, instead of providing one single molecule (e.g., cytotoxic drug and antibody) as traditional therapeutic construct or method may render, the present linker unit is capable of providing more functional elements (either as targeting elements or as effector elements) at one time, thereby greatly improves the therapeutic effect.

In certain therapeutic applications, it is desirable to have a single copy of a targeting or effector element. For example, in using an scFv for targeting an extracellular matrix protein for delivering a bundle of scFv for neutralizing a pro-inflammatory cytokine, a single copy of the scFv specific for the extracellular protein is desirable, so that unwanted effects due to overly tight binding may be avoided. In another example, in using scFv specific for CD3 or CD16a to recruit T cells or NK cells to kill targeted tumor cells bound by a bundle of scFv specific for a tumor-associated antigen on the tumor cells, a single copy of the scFv specific for CD3 or CD16a is desirable, so that unwanted effects due to cross-linking of the CD3 or CD16a may be avoided. In still another example, it is desirable to have only one copy of long-chain PEG for enhancing pharmacokinetic properties. Two or more long PEG chains may cause tangling and affect the binding properties of the targeting or effector elements.

Based on the advantages listed above, the second aspect of the present disclosure pertains to a use of the present linker unit. Specifically, the present disclosure provides a method for treating different diseases (including immune disorder, diffused tumor, solid tumor, osteoporosis disease, and age-related macular degeneration), in which the method comprising administering a subject in need thereof a therapeutically effective amount of the present linker unit.

A first set of diseases treatable by the present linker unit is the immune disorder. Illustrative linker units suitable for treating immune disorders include a first element that is an antibody fragment specific for a pro-inflammatory cytokine or a receptor of the cytokine; or a soluble receptor specific for the cytokine; and a second element that is an antibody fragment specific to the tissue specific extracellular matrix protein.

According to one embodiment, the present linker unit suitable for treating psoriasis comprises a first element of an scFv specific for TNF-α, shared protein of IL-12 and IL-23, IL-17, or the receptor of IL-17; and a second element of an scFv specific for collagen I or collagen VII.

According to another embodiment, the present linker unit suitable for treating systemic lupus erythematosus (SLE), cutaneous lupus, or Sjogren's syndrome comprises an scFv specific for BAFF as the first element; and an scFv specific for collagen I or collagen VII as the second element.

Some skin diseases, such as atopic dermatitis, pemphigus vulgaris, and several types of urticaria, which have obvious inflammatory manifestation in the skin, are not treated with antibodies targeting specific TNF-α, shared protein of IL-12 and IL-23, IL-17, or BAFF, because those antibodies are not found to be sufficiently efficacious. It is rational to expect that if those anti-inflammatory antibodies are distributed favorable to the skin, they may be able to treat those skin diseases.

According to still another embodiment, the present linker unit is used to treat rheumatoid arthritis, psoriatic arthritis, or ankylosing spondylitis. In the embodiment, the first element is an scFv specific for TNF-α, IL-1, IL-6, shared protein of IL-12 and IL-23, IL-17, IL-6R, or IL-17R; and the second element is an scFv specific for collagen II, collagen IX, collagen XI, or α-aggrecan.

According to further another embodiment, the present linker unit suitable for treating inflammatory bowel disease (e.g., Crohn's disease and ulcerative colitis) comprises an scFv specific for TNF-α as the first element; and an scFv specific for collagen III or collagen V as the second element.

In the treatment of diffused tumor (for example, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma), the first element of the present linker unit is the antibody fragment specific for the cell surface antigen associated with and/or overexpressed on the diffused tumor; and the second element of the present linker unit is the antibody fragment specific for the cell surface antigen CD3 or CD16a. According to the embodiments of the present disclosure, the cell surface antigen associated with and/or overexpressed on the diffused tumor is CD5, CD19, CD20, CD22, CD23, CD27, CD30, CD33, CD34, CD37, CD38, CD43, CD72a, CD78, CD79a, CD79b, CD86, CD134, CD137, CD138, or CD319.

For treating B-lymphocyte-derived lymphoma or leukemia, the first element is an scFv specific for CD5, CD19, CD20, CD22, CD23, CD30, CD37, CD79a, or CD79b; and the second element is an scFv specific for CD3 or CD16a.

In the treatment of plasmacytoma or multiple myeloma, the first element is an scFv specific for CD38, CD78, CD138, or CD319; and the second element is an scFv specific for CD3 or CD16a.

To treat T-cell derived lymphoma or leukemia, the first element is an scFv specific for CD5, CD30, or CD43; and the second element is an scFv specific for CD3 or CD16a.

As to the treatment of myelogenous leukemia, the first element is an scFv specific for CD33 or CD34; and the second element is an scFv specific for CD3 or CD16a.

Another set of diseases treatable by the present linker unit is solid tumors, which can be melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, or head and neck squamous cell carcinoma. According to the embodiment of the present disclosure, the first element of the present linker unit is a peptide hormone, a growth factor, or an scFv specific for a tumor-associated antigen; and the second element is an scFv specific for the cell surface antigen CD3 or CD16a.

According to the embodiments of the present disclosure, the peptide hormone is secretin, cholecystokinin (CCK), somatostatin, or thyroid-stimulating hormone (TSH).

In the embodiments of the present disclosure, the growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF).

According to one embodiment, the tumor-associated antigen is selected from the group consisting of human epidermal growth factor receptor (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM).

In some instances, some tumor-associated antigen may be shed from the solid tumor of a subject and wanders into the circulation system of the subject. In these cases, the present method for treating solid tumor comprises the step of, (a) subjecting the subject to a blood dialysis procedure using an antibody specific for one or more tumor-associated antigens to remove the tumor-associated antigens that are shed from the tumor and wanders into the circulation of the subject; and (b) administering the present linker unit for treating the solid tumor.

For the purpose of treating osteoporosis disease, the first element of the present disclosure is an scFv specific for ligand of receptor activator of nuclear factor κB (RANKL); and the second element of the present disclosure is a second scFv specific for collagen I or osteonectin.

According to the embodiments of the present disclosure, the present linker unit is useful in treating age-related macular degeneration (AMD), in which the first element of the present linker unit is an scFv specific for VEGF-A; and the second element of the present disclosure is a long PEG chain having a molecular weight of about 20,000 to 50,000 daltons.

EXPERIMENTAL EXAMPLES

Example 1: Synthesis of Peptide 1 (SEQ ID NO: 17), Peptide 2 (SEQ ID NO: 18), and Peptide 3 (SEQ ID NO: 19) as Peptide Cores, and Conjugation of SH Group of Cysteine Residue with Maleimide-PEG$_3$-Transcyclooctene (TCO) as Conjugating Arm Peptides 1 to 3 were synthesized by solid-phase peptide synthesis method and purified with reverse phase high-performance liquid chromatography (HPLC) using Shimadzu Nexera-i LC-2040C 3D HPLC system to 95% purity. The reverse phase HPLC used a Kromasil 100-5C18 column (250 mm×4.6 mm; 5 μm), with a mobile phase of acetonitrile and 0.1% trifluoroacetic acid, a linear gradient of 10% to 45% acetonitrile over 15 minutes, at a flow rate of 1.0 mL/min and a column temperature of 25° C.

Figure 2:
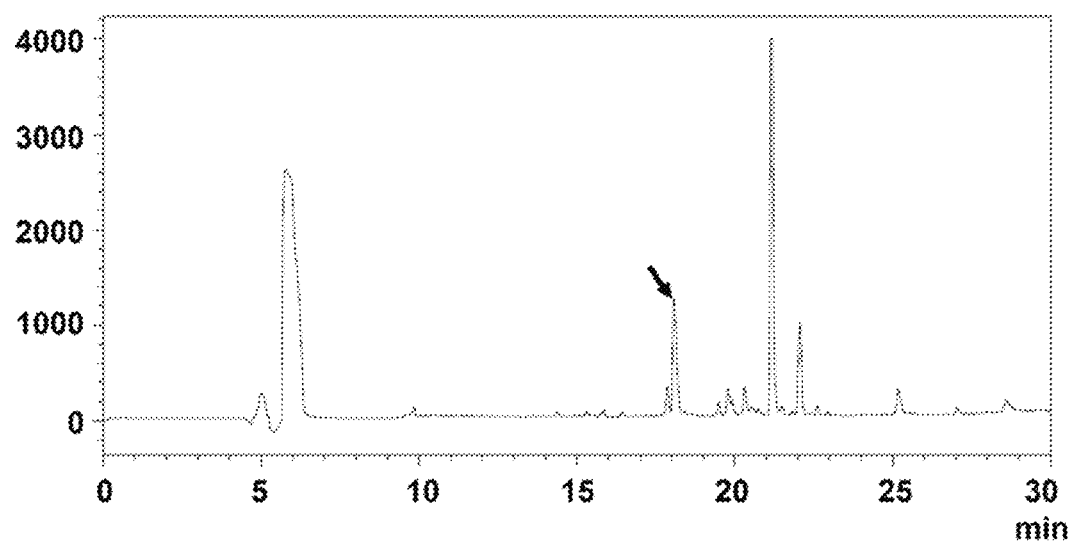
FIG. 2 shows the reverse phase HPLC elution profile for the purification of TCO-peptide 2. Peptide 2 is SEQ ID NO:18.

The purified peptide was dissolved in 100 mM sodium phosphate buffer (pH 7.0) containing 50 mM NaCl and 5 mM EDTA at a final concentration of 2 mM. The dissolved peptide was reduced by 1 mM tris(2-carboxyethyl)phosphine (TCEP) at 25° C. for 2 hours. For conjugating the SH group of the cysteine residue with maleimide-PEG$_3$-TCO (Conju-probe Inc., San Diego, USA) to create a functional linking group TCO, the peptide and maleimide-PEG$_3$-TCO were mixed at a 1/10 ratio and incubated at pH 7.0 and 25° C. for 24 hours. TCO-conjugated peptides were purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C. FIG. 2 showed the reverse phase HPLC elution profile for the purification of TCO-peptide 2; with the peak of the TCO-peptide 2 being indicated with an arrow.

The identification of the three synthesized TCO-peptides (illustrated below) was carried out by mass spectrometry MALDI-TOF. Mass spectrometry analyses were performed by Mass Core Facility of Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany).

The present TCO-peptide 1, as illustrated below, had a molecular weight (m.w.) of 1807.0 daltons.

(SEQ ID NO: 17)

The present TCO-peptide 2, as illustrated below, had a m.w. of 2078.9 daltons.

(SEQ ID NO: 18)

The present TCO-peptide 3, as illustrated below, had a m.w. of 3380.8 daltons.

```
            Ac
            |
TCO—PEG₃—CGSKGSKGSKGSKGSKGSKGSKGSKGSK
```

Example 2: Synthesis of Peptides 1 and 2 as Peptide Cores, and Conjugation of SH Group of Cysteine Residue with Maleimide-PEG₄-Tetrazine as Conjugating Arm Peptides 1 and 2 were prepared as in Example 1, and then dissolved in 100 mM sodium phosphate buffer (pH 7.0) containing 50 mM NaCl and 5 mM EDTA at 2 mM final concentration. The dissolved peptide was reduced by 1 mM TCEP at 25° C. for 2 hours. For conjugating the SH group of cysteine residue with maleimide-PEG₄-tetrazine (Conjuprobe Inc.) to create a functional linking group tetrazine, the peptide and maleimide-PEG₄-tetrazine were mixed at a 1/5 ratio and incubated at pH 7.0 and 4° C. for 24 hours. Tetrazine-conjugated peptides were purified by reverse phase HPLC on a Supelco C18 column (250 mm×10 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C. The identification of said two synthesized tetrazine-peptides was carried out by mass spectrometry MALDI-TOF set forth in the preceding Example.

The present tetrazine-peptide 1, as illustrated below, had a m.w. of 1912.7 daltons.

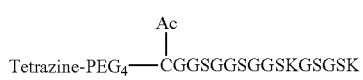
(SEQ ID NO: 17)
```
                     Ac
                     |
Tetrazine-PEG₄—CGGSGGSGGSKGSGSK
```

The present tetrazine-peptide 2, as illustrated below, had a m.w. of 2185.2 daltons.

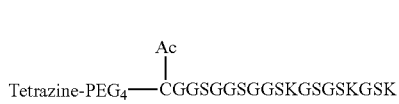
(SEQ ID NO: 18)
```
                     Ac
                     |
Tetrazine-PEG₄—CGGSGGSGGSKGSGSKGSK
```

Example 3: Synthesis of Peptides 1 and 2 as Peptide Cores, and Conjugation of SH Group of Cysteine Residue with Maleimide-PEG₅-DBCO as Conjugating Arm Peptides 1 and 2 were prepared as in the earlier Example. The peptide was dissolved in 100 mM sodium phosphate buffer (pH 7.0) containing 50 mM NaCl and 5 mM EDTA at 2 mM final concentration. The dissolved peptide was reduced by 1 mM TCEP at 25° C. for 2 hours. For conjugating the SH group of cysteine residue with dibenzylcyclooctyne (DBCO) to create a functional linking group of DBCO, the peptide and maleimide-PEG₅-DBCO (Conjuprobe Inc.) were mixed at a 1/5 ratio and incubated at pH 7.0 and the room temperature for 24 hours. DBCO-conjugated peptides were purified by reverse phase HPLC on a Supelco C18 column (250 mm×10 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C. The identification of the two synthesized DBCO-peptides was carried out by mass spectrometry MALDI-TOF.

The present DBCO-peptide 1, as illustrated below, had a m.w. of 1941.8 daltons.

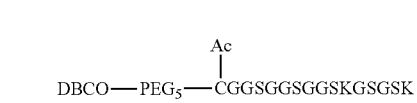
(SEQ ID NO: 17)
```
              Ac
              |
DBCO—PEG₅—CGGSGGSGGSKGSGSK
```

The present DBCO-peptide 2, as illustrated below, had a m.w. of 2213.9 daltons.

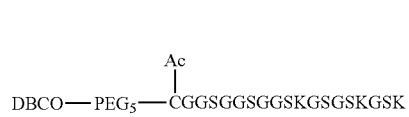
(SEQ ID NO: 18)
```
              Ac
              |
DBCO—PEG₅—CGGSGGSGGSKGSGSKGSK
```

Example 4: Synthesis of Peptide 4 (SEQ ID NO: 20), Peptide 5 (SEQ ID NO: 21), and Peptide 6 (SEQ ID NO: 22) as Peptide Cores Peptides 4 to 6 were synthesized by solid-phase peptide synthesis method, and then purified by reverse phase HPLC to 95% purity. The unnatural amino acids, homopropagylglycine ($G^{HP}$) and azidohomoalanine ($A^{AH}$) contained an alkyne and an azide group, respectively. The reverse phase HPLC used a Supelco C18 column (250 mm×4.6 mm; 5 µm), with a mobile phase of acetonitrile and 0.1% trifluoroacetic acid, a linear gradient of 2% to 90% acetonitrile over 30 minutes, at a flow rate of 1.0 mL/min and a column temperature of 25° C.

The identification of said three synthesized peptides was carried out by mass spectrometry MALDI-TOF. The present peptide 4 (Ac-$G^{HP}$GGSGGSGGSKGSGSK; SEQ ID NO: 20) had a molecular weight of 1317.0 daltons; the present peptide 5 (Ac-$G^{HP}$GGSGGSGGSKGSGSKGSK; SEQ ID NO: 21) had a m.w. of 1589.9 daltons; while the present peptide 6 (Ac-$A^{AH}$GGSGGSGGSKGSGSKGSK; SEQ ID NO: 22) had a m.w. of 1634.66 daltons.

Example 5: Synthesis of Peptide 7 (SEQ ID NO: 23) as Peptide Core and Conjugation of SH Group of Cysteine Residue with Maleimide-PEG₃-TCO or Maleimide-PEG₄-Tetrazine as Conjugating Arm Peptide 7 (Ac-$G^{HP}$GGSGGSGGSKGSGSKGSGSC; SEQ ID NO: 23) was synthesized, and the conjugation of the crosslinkers was performed as described in above examples. The synthesized TCO-peptide 7 and tetrazine-peptide 7 were examined using MALDI-TOF.

The present TCO-peptide 7, as illustrated below, had a m.w. of 1736.78 daltons.

Ac-$G^{HP}$-GGSGGSGGSKGSGSKGSGSC-PEG₃-TCO

The present tetrazine-peptide 7, as illustrated below, had a m.w. of 1820.62 daltons.

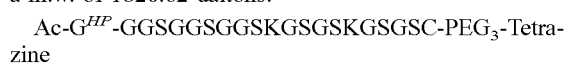
Ac-$G^{HP}$-GGSGGSGGSKGSGSKGSGSC-PEG₃-Tetrazine

Example 6: Synthesis of Peptide 8 (SEQ ID NO: 24) as Peptide Core, and Conjugation of SH Group of Cysteine Residue with Maleimide-PEG$_3$-TCO, Maleimide-PEG$_4$-Tetrazine or Maleimide-PEG$_5$-DBCO as Conjugating Arm Peptide 8 (Ac-C-Xaa-K-Xaa-K-Xaa-K; wherein Xaa was a PEGylated amino acid with 2 EG units; SEQ ID NO: 24) was synthesized by solid-phase peptide synthesis method and then purified using reverse phase HPLC to 95% purity. The reversed phase HPLC was conducted using a Kromasil 100-5C18 column (250 mm×4.6 mm; 5 μm), with a mobile phase of water and 0.1% TFA, a linear gradient of 10% to 40% acetonitrile over 12 minutes, at a flow rate of 1.0 mL/min and a column temperature of 25° C.

The identification of the synthesized peptide 8 was carried out by mass spectrometry ESI-MS. High resolution and high mass accuracy experiments were done on a LTQ Orbitrap XL ETD mass spectrometer (Thermo Fisher Scientific, San Jose, Calif.) equipped with standard ESI ion source. Mass ESI-TOF analyses were performed by GRC Mass Core Facility of Genomics Research Center, Academia Sinica, Taipei, Taiwan. The sample of the synthesized peptide showed a strong molecular ion at 981.9, corresponding to [M–H]$^-$, indicating that the actual molecular weight of the PEGylated peptide was 983.0 daltons.

The conjugation of the crosslinkers was performed as described in above examples, and mass spectrometry ESI-MS was used to examine the products (illustrated below, in which the Xaa$_2$ denotes a PEGylated amino acid with two EG units).

The present TCO-peptide 8, as illustrated below, had a m.w. of 1478.87 daltons.

TCO-PEG$_3$-C-(Xaa$_2$-K)$_3$

The present tetrazine-peptide 8, as illustrated below, had a m.w. of 1584.92 daltons.

Tetrazine-PEG$_4$-C-(Xaa$_2$-K)$_3$

The present DBCO-peptide 8, as illustrated below, had a m.w. of 1613.8 daltons

DBCO-PEG$_5$-C-(Xaa$_2$N$_3$

Example 7: Synthesis of Peptide 9 (SEQ ID NO: 25) as Peptide Core, and Conjugation of SH Group of Cysteine Residue with Maleimide-PEG$_3$-TCO as Conjugating Arm Peptide 9 (Ac-C-Xaa-K-Xaa-K-Xaa-K-Xaa-K-Xaa-K; wherein Xaa was a PEGylated amino acid with 6 EG units; SEQ ID NO: 25) was prepared as set forth in an earlier Example. The identification of the synthesized peptide 9 was carried out by mass spectrometry ESI-MS. The sample of the synthesized peptide showed a strong molecular ion at 828.0, corresponding to [M+3H]$^{3+}$, indicating that the actual molecular weight of the PEGylated peptide was 2480.7 daltons.

The conjugation of the crosslinker was performed as set forth in above examples, and then examined with mass spectrometry ESI-MS. The present TCO-peptide 9, as illustrated below, had a m.w. of 2975 daltons.

TCO-PEG$_3$-C-(Xaa$_6$-K)$_5$

Example 8: Synthesis of Linker Unit by Conjugating NHS-PEG$_{12}$-Maleimide to NH$_2$ Groups of TCO-Peptides 1 and 2

Figure 3:
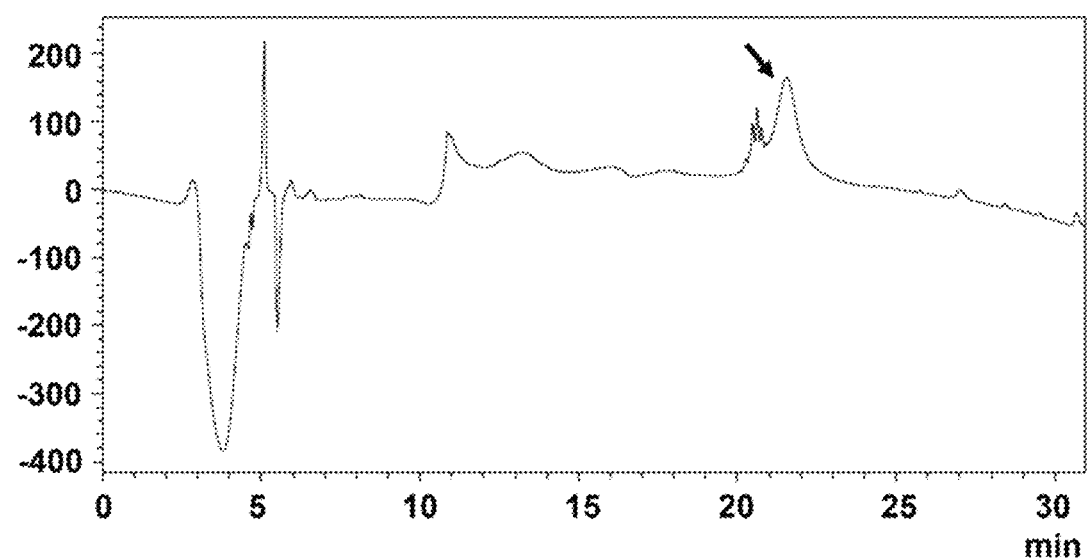
FIG. 3 shows the reverse phase HPLC profile for the purification of $PEG_{12}$-maleimide-conjugated TCO-peptide 2.

Two linking arms of PEG$_{12}$-maleimide were attached to the peptide core TCO-peptide 1; while three linking arms of PEG$_{12}$-maleimide were attached to the peptide core TCO-peptide 2. The crosslinker, NHS-PEG$_{12}$-maleimide (succinimidyl-[(N-maleimido-propionamido)-dodecaethyleneglycol] ester), was purchased from Thermo Fisher Scientific Inc. (Waltham, USA). The conjugation procedure was performed per the manufacturer's instruction; the peptide with lysine residues was dissolved in the conjugation buffer, phosphate buffered saline (PBS, pH 7.5) at 100 mM. NHS-PEG$_{12}$-maleimide crosslinker was added to the dissolved peptide at 1 mM final concentration (20-fold molar excess over 0.1 mM peptide solution). The reaction mixtures were incubated for 18 hours at room temperature. PEG$_{12}$-maleimide-conjugated TCO-peptide 1 and peptide 2 were purified by reverse phase HPLC on a Supelco C18 column (250 mm×4.6 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C. FIG. 3 showed the reverse phase HPLC profile for the purification of PEG$_{12}$-maleimide-conjugated TCO-peptide 2, with the peak being indicated with an arrow.

The identification of the PEG$_{12}$-maleimide-conjugated TCO-peptide 1 and peptide 2 was carried out by mass spectrometry MALDI-TOF.

The present PEG$_{12}$-maleimide-conjugated TCO-peptide 1, as illustrated below, was a peptide core-based linker unit carrying one coupling arm with a TCO group and two PEG linking arms with maleimide groups. The result of mass spectrometry MALDI-TOF indicated that the present molecular construct had a m.w. of 3330.7 daltons.

(SEQ ID NO: 17)

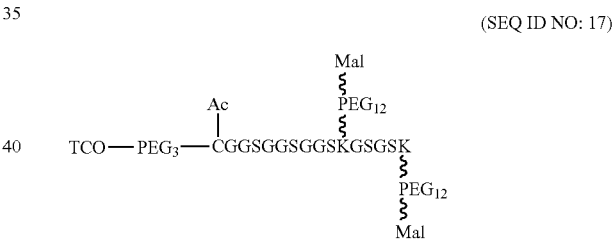

Figure 4:
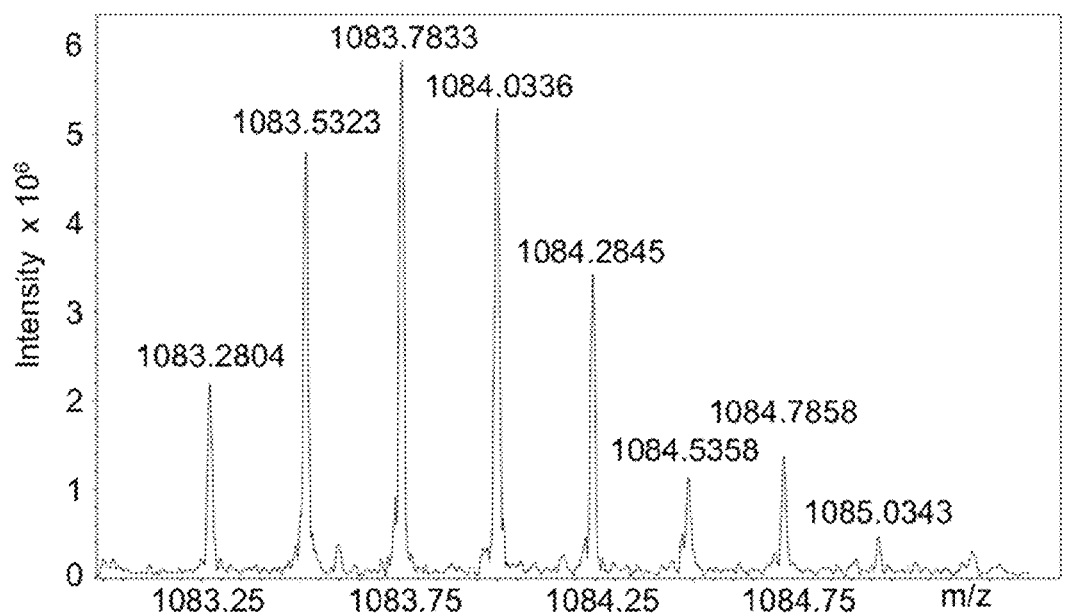
FIG. 4 shows the mass spectrometry MALDI-TOF result of $PEG_{12}$-maleimide-conjugated TCO-peptide 2.

The present PEG$_{12}$-maleimide-conjugated TCO-peptide 2, as illustrated below, was a peptide core-based linker unit carrying one coupling arm with a TCO group and three PEG linking arms with maleimide groups. FIG. 4 showed the mass spectrometry MALDI-TOF result, indicating that the present molecular construct had a m.w. of 4332 daltons; (ESI-TOF) m/z (z=4): [M+4H]$^+$; calculated for $C_{185}H_{313}N_{31}O_{83}S_1$ 1083.7829; found 1083.7833), corresponding to [M+Na]$^+$.

(SEQ ID NO: 18)

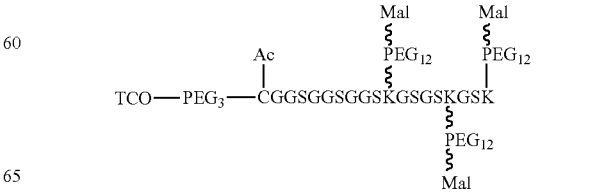

Example 9: Synthesis of Linker Unit by
Conjugating NHS-PEG$_{12}$-Maleimide to NH$_2$
Groups of Tetrazine-Peptide 2 and DBCO-Peptide
1

Three linking arms of PEG$_{12}$-maleimide were attached to tetrazine-peptide 2, while two linking arms were attached to DBCO-peptide 1. The conjugation of NHS-PEG$_{12}$-maleimide to the NH$_2$ groups of the lysine residues of the peptide cores was performed as described in the earlier Examples, and the products were identified using mass spectrometry MALDI-TOF.

Figure 5A:
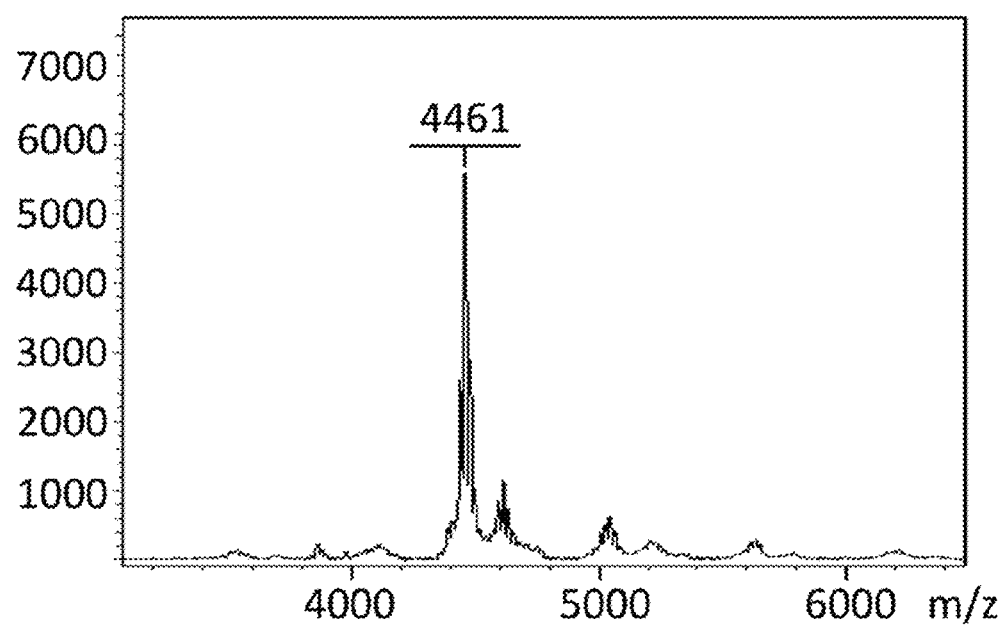
FIGS. 5A and 5B respectively show the mass spectrometry MALDI-TOF result of $PEG_{12}$-maleimide-conjugated tetrazine-peptide 2 and DBCO-peptide 2.

As illustrated below, the present PEG$_{12}$-maleimide-conjugated tetrazine-peptide 2 carried one coupling arm with a tetrazine group and three PEG linking arms with maleimide groups. FIG. 5A showed the mass spectrometry MALDI-TOF result, indicating that the construct had a m.w. of 4461 daltons.

(SEQ ID NO: 18)

```
                    Mal         Mal
                     ⌇           ⌇
                    PEG₁₂       PEG₁₂
            Ac       ⌇           ⌇
             |       ⌇           ⌇
Tetrazine-PEG₄—CGGSGGSGGSKGSGSKGSK
                         ⌇
                        PEG₁₂
                         ⌇
                        Mal
```

Figure 5B:
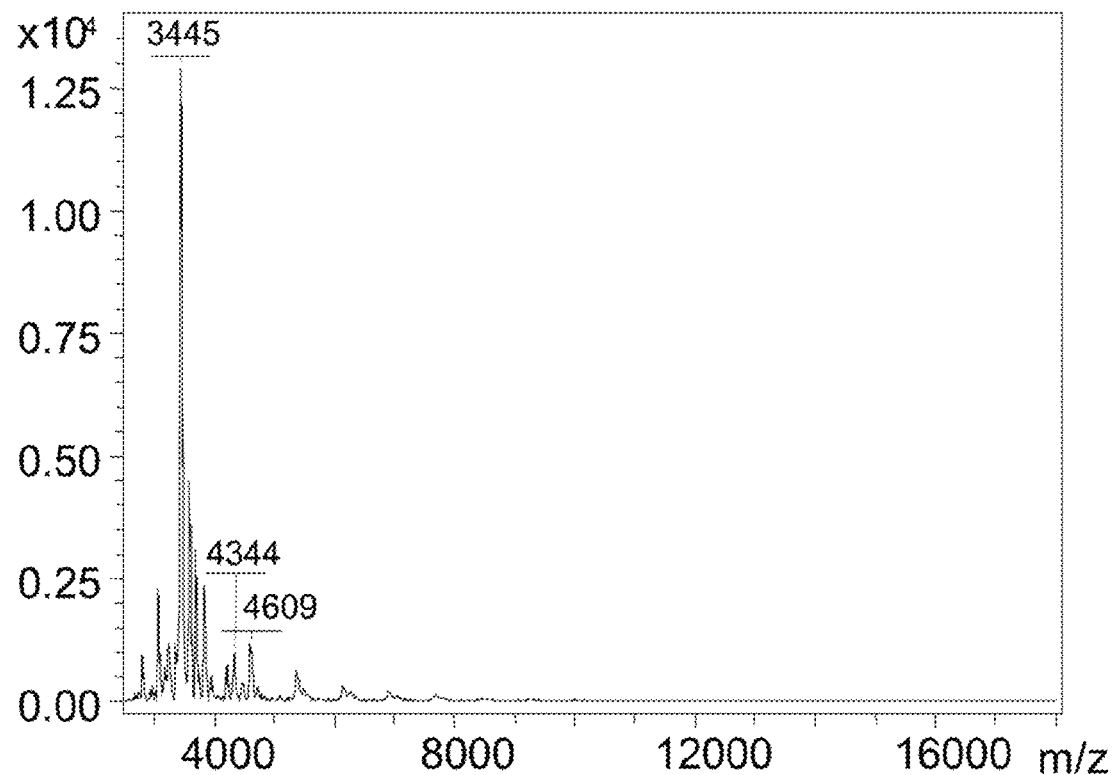

As illustrated below, the present PEG$_{12}$-maleimide-conjugated DBCO-peptide 1 carried one linking arm with a DBCO group and two PEG linking arms with maleimide groups. FIG. 5B showed the mass spectrometry MALDI-TOF result, indicating that the construct had had a m.w. of 3445 daltons.

(SEQ ID NO: 17)

```
                Mal
                 ⌇
                PEG₁₂
         Ac      ⌇
          |      ⌇
DBCO—PEG₃—CGGSGGSGGSKGSGSK
                  ⌇
                 PEG₁₂
                  ⌇
                 Mal
```

Example 10: Synthesis of Linker Unit by
Conjugating NHS-PEG$_{12}$-Maleimide to NH$_2$
Groups of Peptides 4 to 6

Two linking arms of PEG$_{12}$-maleimide were attached to the peptide 4; while three linking arms of PEG$_{12}$-maleimide were attached to the peptide 5 and peptide 6. The conjugation of NHS-PEG$_{12}$-maleimide to the NH$_2$ groups of the lysine residues of the peptide cores was performed as in the earlier Example, and the products were identified using mass spectrometry MALDI-TOF.

The present PEG$_{12}$-maleimide-conjugated peptide 4, as illustrated below, had a m.w. of 2817.3 daltons; it was a peptide core-based linker unit carrying one alkyne group and two PEG linking arms with maleimide groups.

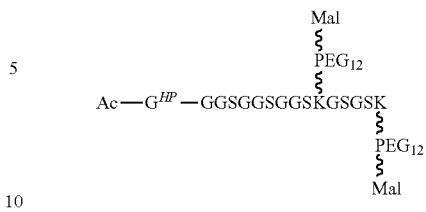

(SEQ ID NO: 20)

The present PEG$_{12}$-maleimide-conjugated peptide 5 (illustrated below) had a m.w. of 3839.2 daltons; it was a peptide core-based linker unit carrying one alkyne group and three PEG linking arms with maleimide groups.

(SEQ ID NO: 21)

```
                    Mal         Mal
                     ⌇           ⌇
                    PEG₁₂       PEG₁₂
                     ⌇           ⌇
        Ac—G^{HP}—GGSGGSGGGSKGSGSKGSK
                         ⌇
                        PEG₁₂
                         ⌇
                        Mal
```

PEG$_{12}$-maleimide-conjugated peptide 6 (illustrated below) had a m.w. of 3811.5 daltons; it was a peptide core-based linker unit carrying one azide group and three PEG linking arms with maleimide groups.

(SEQ ID NO: 22)

```
                    Mal         Mal
                     ⌇           ⌇
                    PEG₁₂       PEG₁₂
                     ⌇           ⌇
        Ac—A^{HA}—GGSGGSGGSKGSGSKGSK
                         ⌇
                        PEG₁₂
                         ⌇
                        Mal
```

Example 11: Synthesis of Linker Unit by
Conjugating NHS-PEG$_{12}$-Maleimide to NH$_2$
Groups of TCO-Peptide 7 and Tetrazine-Peptide 7

Two linking arms of PEG$_{12}$-maleimide were attached to a peptide core, the peptide 7 from the preceding Examples. The conjugation of NHS-PEG$_{12}$-maleimide to the NH$_2$ groups of the lysine residues of the peptide core was performed as described above, and the identification was carried out by mass spectrometry MALDI-TOF.

The present PEG$_{12}$-maleimide-conjugated TCO-peptide 7, as illustrated below, had a m.w. of 3237.63 daltons; it was a peptide core-based linker unit carrying one an alkyne group, one coupling arm with a TCO group, and two PEG linking arms with maleimide groups.

(SEQ ID NO: 23)

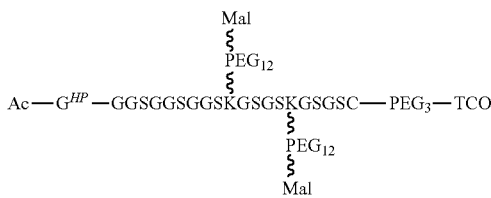

The present PEG$_{12}$-maleimide-conjugated tetrazine-peptide 7, as illustrated below, had a m.w. of 3342.98 daltons; it was a peptide core-based linker unit carrying one alkyne group, one coupling arm with a tetrazine group, and two PEG linking arms with maleimide groups.

(SEQ ID NO: 23)

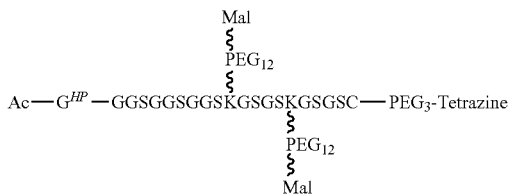

Example 12: Synthesis of Linker Unit by Conjugating NHS-PEG$_{12}$-Maleimide to NH$_2$ Groups of TCO-Peptide 8 and Tetrazine-Peptide 8

Three linking arms of PEG$_{12}$-maleimide were attached to the peptide cores, TCO-peptide 8 and tetrazine-peptide 8. The conjugation of NHS-PEG$_{12}$-maleimide to the NH$_2$ groups of the lysine residues of the peptide core was performed as in Example 8, and the identification was carried out by mass spectrometry MALDI-TOF.

The present PEG$_{12}$-maleimide-conjugated TCO-peptide 8 (illustrated below) had a m.w. of 3774.9 daltons; it was a linker unit based on PEGylated amino acid and lysine; it carried one coupling arm with a TCO group and three PEG linking arms with maleimide groups.

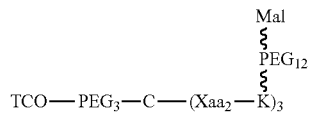

Figure 6:
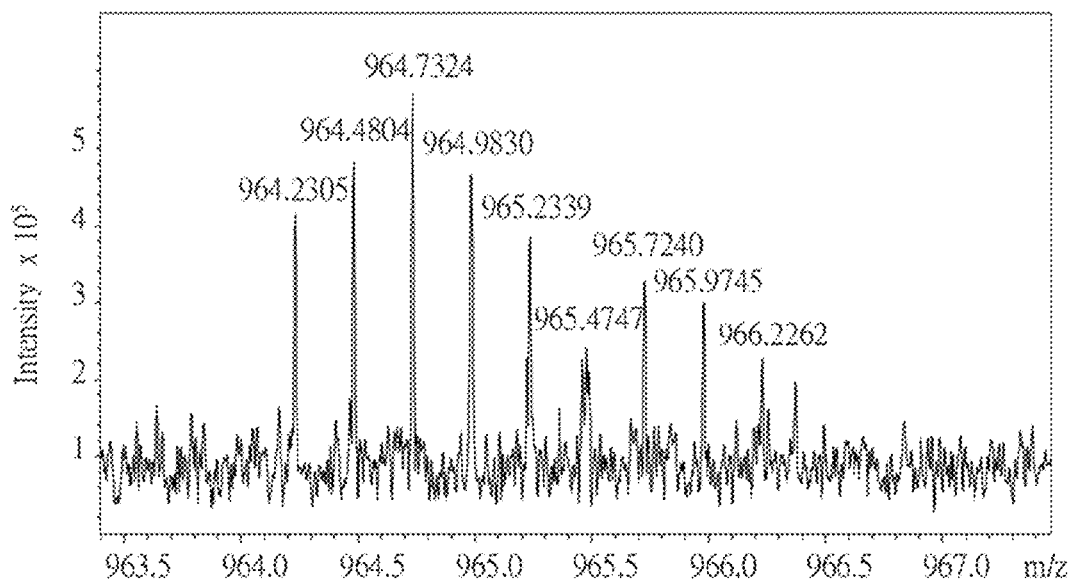
FIG. 6 shows the mass spectrometry ESI-TOF result of $PEG_{12}$-maleimide-conjugated tetrazine-peptide 8.

The present PEG$_{12}$-maleimide-conjugated tetrazine-peptide 8 (illustrated below) had a m.w. of 3856.94 daltons (FIG. 6; (ESI-TOF) m/z (z=4): [M+4H]$^+$ Calculated for C$_{171}$H$_{287}$N$_{23}$O$_{71}$S$_1$H$_3$Na 964.7363; Found 964.7324); it was a linker unit based on PEGylated amino acid and lysine; it carried one coupling arm with a tetrazine group and three PEG linking arms with maleimide groups.

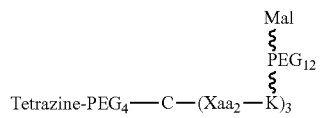

Example 13: Synthesis of Linker Unit by Conjugating NHS-PEG$_6$-Maleimide to NH2 Groups of TCO-Peptide 9

Five linking arms of PEG$_6$-maleimide were attached to the peptide cores, TCO-peptide 9. The conjugation of NHS-PEG$_6$-maleimide to the NH$_2$ groups of the lysine residues of the peptide core was performed as in Example 8, the identification was carried out by mass spectrometry MALDI-TOF.

Figure 7:
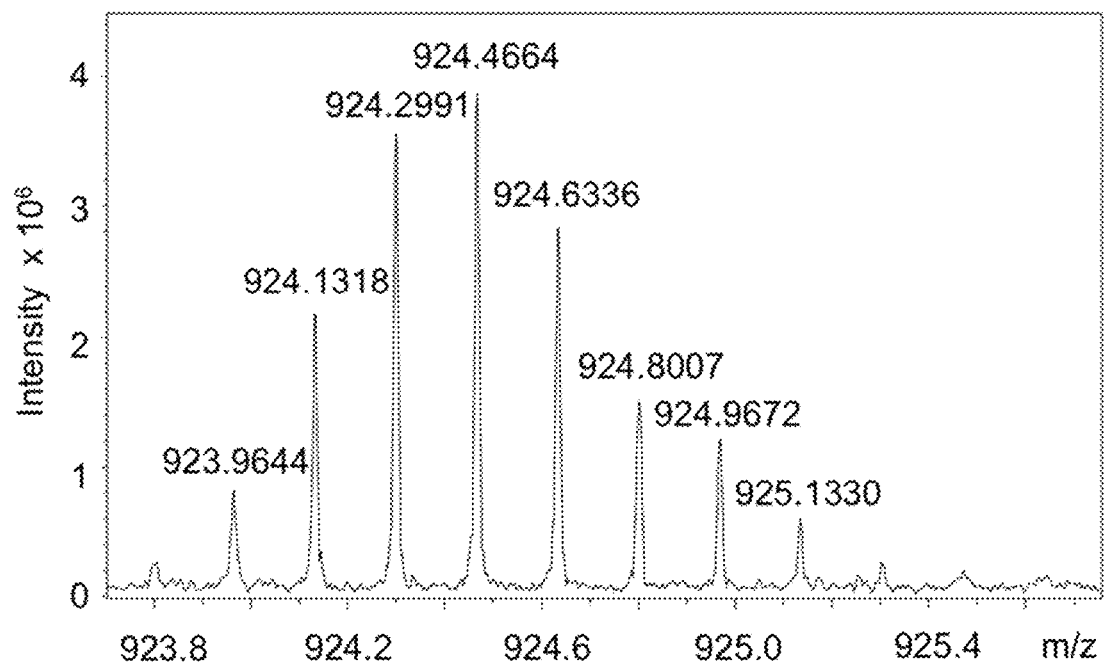
FIG. 7 shows the mass spectrometry ESI-TOF result of $PEG_6$-maleimide-conjugated TCO-peptide 9.

PEG$_6$-maleimide-conjugated TCO-peptide 9 (illustrated below) had a m.w. of 5543.78 daltons (FIG. 7; (ESI-TOF) m/z (z=6): [M+6H]$^+$ Calculated for C$_{244}$H$_{421}$N$_{29}$O$_{101}$S$_1$Na 924.297; Found 924.299); it was a linker unit based on PEGylated amino acid and lysine; it carried one coupling arm with a TCO group and five PEG linking arms with maleimide groups.

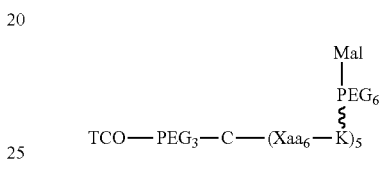

Example 14: Conjugation of Five DM1-SMCC Molecules to TCO-Peptide 9

Figure 8:
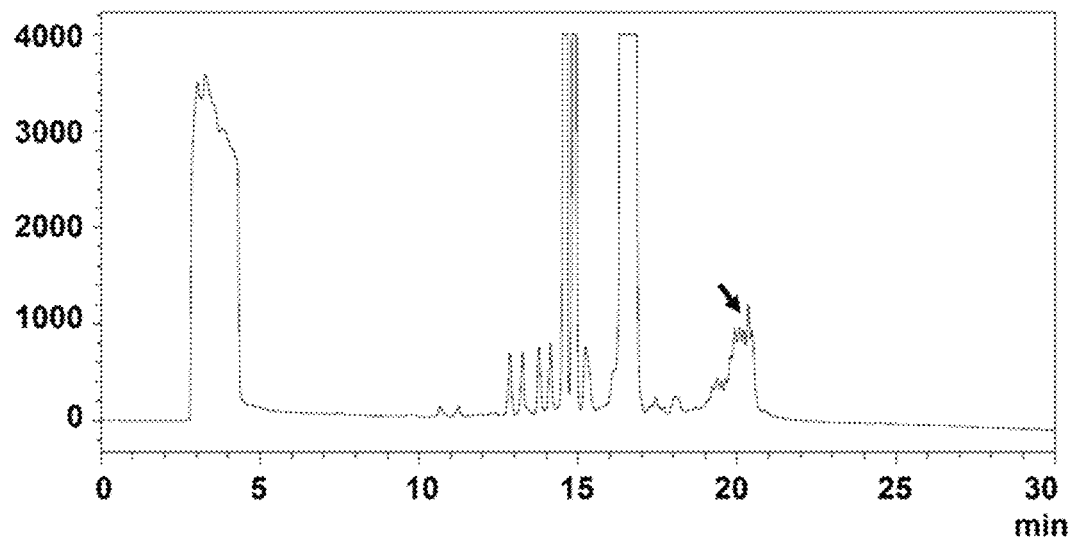
FIG. 8 shows the reverse phase HPLC profile for the purification of TCO-peptide 9 with 5 DM1-SMCC molecules.
Figure 9:
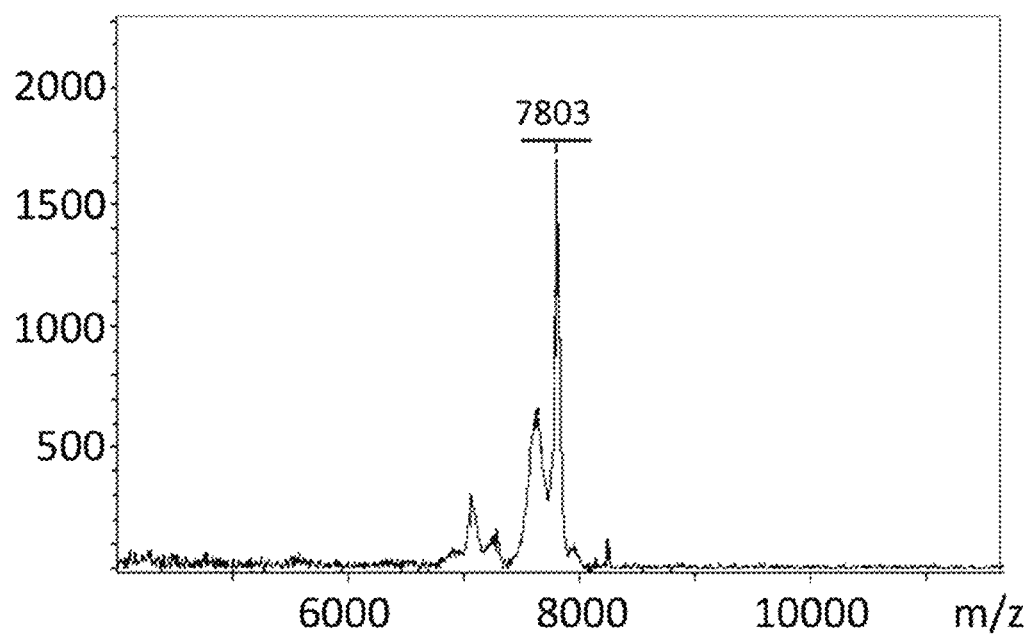
FIG. 9 shows the mass spectrometry result of TCO-peptide 9 with 5 DM1-SMCC molecules.

DM1-SMCC, which was N$_2$'-Deacetyl-N$_2$'-(3-mercapto-1-oxopropyl)-maytansine (DM1) modified by a linker, succinimidyl-4-(N-maleimido-methyl) cyclohexan-1-carboxylate (SMCC), was purchased from ALB Technology Inc., Hong Kong, China. TCO-peptide 9 with free amine groups was dissolved in 100 mM sodium phosphate buffered at pH 7.5. DM1-SMCC was added to the TCO-peptide 9 solution at 1 mM final concentration (25-fold molar excess over the 0.04 mM TCO-peptide 9 solution) by adding 4 µl of the 250 mM DM1-SMCC solution per milliliter of NH$_2$-containing TCO-peptide 9 solution. The reaction mixtures were incubated for 24 hours at room temperature. The reaction product was separated by HPLC and then lyophilized. The TCO-peptide 9 with five DM1-SMCC molecules was purified by reverse phase HPLC on a Supelco C18 column (250 mm×4.6 mm; 5 µm), using a mobile phase of acetonitrile and 0.1% trifluoroacetic acid, a linear gradient of 30% to 100% acetonitrile over 30 minutes, at a flow rate of 1.0 mL/min and a column temperature of 25° C. FIG. 8 showed the reverse phase HPLC profile for the purification of TCO-peptide 9 with five DM1-SMCC molecules (also referred to as a drug bundle); the peak being indicated with an arrow. The mass spectroscopic analysis of the thus-synthesized drug bundle, as provided in FIG. 9, indicated that the molecular construct had a m.w. of 7803 daltons.

The present drug bundle, as illustrated below, was composed of a linker unit with a free TCO functional group and a set of five DM1 molecules as effector elements.

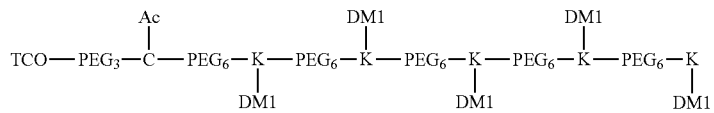

Example 15: Conjugation of LPS Molecules to TCO-Peptide 1

LPS from *Salmonella enterica* sv. *Minnesota* (Cat No. L2137, Sigma) was chromatographically purified on the Superdex 200 10/300 Tricon column (HR, GE Healthcare) in an ÄKTA Explorer FPLC system. The elution buffer, 50 mM HEPES, pH7.5, was used. The sample was injected and eluted isocratically at 0.5 mL/min and collected in 1-mL fractions. The fractions containing LPS were then dialyzed against MilliQ water using a 3500 MWCO membrane at 4° C. overnight. The dialyzed LPS were lyophilized for subsequent conjugation.

Figure 10:
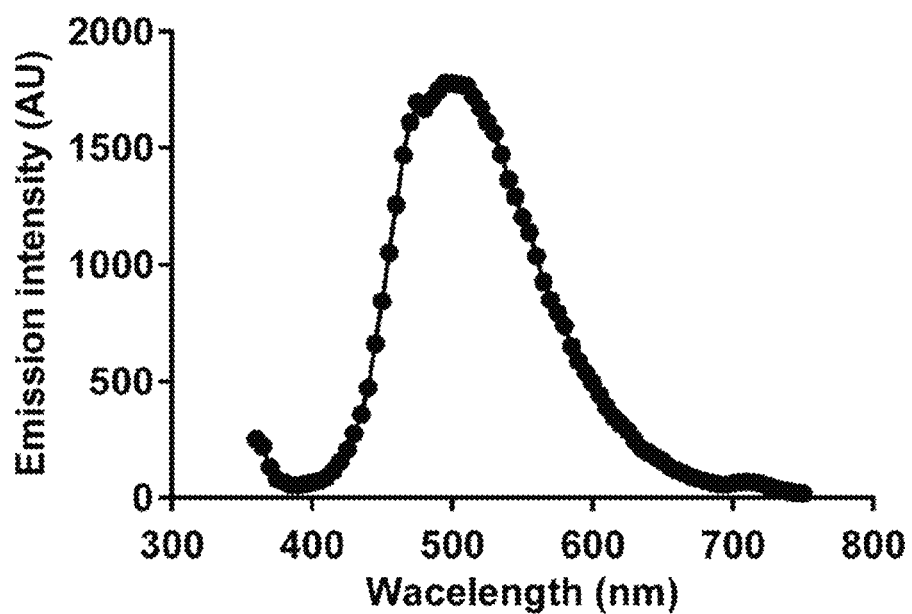
FIG. 10 shows that LPS, upon the reaction with dansyl hydrazine, exhibited an emission maximum at 495 nm in fluorescence spectrophotometric analysis.

Before the conjugation, the purified LPS was activated as follows. An amount of 1 ml of 2 mg/ml of an aqueous LPS solution was vortexed for 3 min and sonicated for 15 min at 25° C. Then, 1 ml of 4.5 mM sodium deoxycholate (NaDC) was added; 100 µl of 2.5 mM EDTA solution was added. The mixture was stirred for 30 minutes at 37° C., sonicated for 15 minutes, and stirred for another 30 minutes at 37° C. 40 µl of 100 mg/ml 1-cyano-4-dimethylaminopyridinium tetrafluoroborate (CDAP) in acetonitrile was added. After 30 seconds, 40 µl of 0.2M aqueous triethylamine (TEA) was added. The mixture was kept at 25° C. for further 150 seconds with stirring to allow activation of LPS by CDAP LPS derived from *Salmonella enterica* sv. *Minnesota* was reacted with dansyl hydrazine to introduce a hydrazine group for subsequent coupling with amine group on a linker unit. Briefly, 1 ml of 2.0 mg/ml dansyl hydrazine in 0.1 M sodium borate buffer, pH 9.3, was added to the CDAP-activated LPS. The mixture was left to react overnight in the dark at 25° C. under stirring. The reaction was quenched by adding 100 µl of ethanolamine. The unreacted dansyl hydrazine was removed by dialysis against Milli-Q water using a 3,500 MWCO dialysis membrane for 24 hours at 4° C. in the dark. The sample was characterized using fluorescence spectroscopy by measuring the emission spectra under the excitation at 325 nm. FIG. 10 showed that LPS, upon the reaction with dansyl hydrazine, exhibited an emission maximum at 495 nm in fluorescence spectrophotometric analysis.

The identification of the purified LPS and the dansyl-activated LPS was carried out by mass spectrometry MALDI-TOF. The purified LPS had a m.w. of 3143 daltons; the dansyl-activated LPS had a m.w. of 3651 daltons, indicating one LPS conjugated with two dansyl hydrazine molecules; one dansyl hydrazine molecule had a m.w. of 265 daltons.

The conjugation of LPS molecules to the NH$_2$ groups of the lysine residues of TCO-peptide 1 was performed. Briefly, 0.67 mole of the dansyl-activated LPS was mixed with 0.067 mole of TCO-peptide 1 in 0.1 M sodium bicarbonate buffer, pH 9.5, at room temperature overnight.

The present drug bundle, as illustrated below, was composed of a linker unit with a free TCO functional group and a set of two LPS molecules as effector elements.

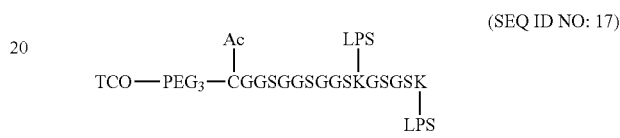

(SEQ ID NO: 17)

Example 16: Conjugation of a Imiquimod Molecule with NHS-PEG$_6$-Maleimide-Conjugated TCO-Peptide 9

Figure 11:
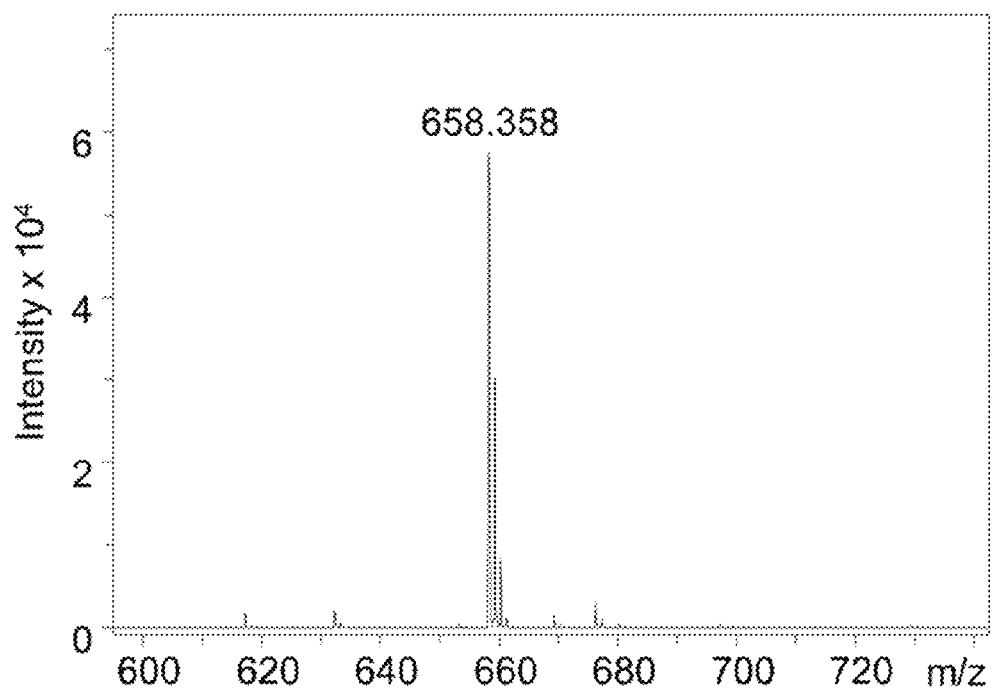
FIG. 11 shows mass spectrometric analysis of $PEG_5$-NHS conjugated with imiquimod.

The NH$_2$ group of the imiquimod molecule was reacted with a homo-bifunctional crosslinker, NHS-PEG$_5$-NHS (Conju-probe Inc.) at a 1:3.5 molar ratio. Mass spectrometric analysis showed that PEG$_5$-NHS conjugated with imiquimod had a m.w. of 658.36 daltons (FIG. 11).

The product, imiquimod-PEG$_5$-NHS, was purified by HPLC to remove the excess, unreacted crosslinkers. TCO-peptide 9 and imiquimod-PEG$_5$-NHS were then mixed in 100 mM sodium phosphate buffer at pH 7.5 at 25° C. for 18 hours. Mass spectrometric analysis showed that the drug bundle with imiquimod had a m.w. of 5135 daltons.

The present drug bundle, as illustrated below, was composed of a linker unit with a free TCO functional group and a set of five imiquimod molecules as effector elements.

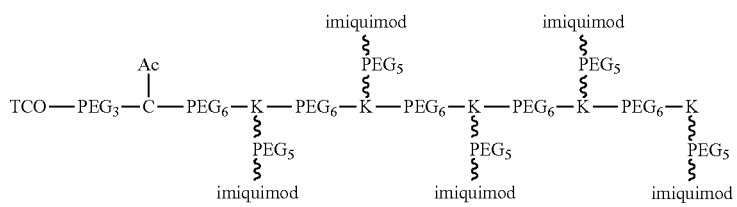

Example 17: Conjugation of DOTA-NHS to TCO-Peptide 9

DOTA-NHS (1,4,7,10-tetraazacyclododecane-1,4,7,10-tetraacetic acid N-hydroxy-succinimide ester) was purchased from Macrocyclics, Inc. Dallas, USA. Conjugation of DOTA-NHS to TCO-peptide 9 employed a two-step procedure as illustrated in Scheme 14.

<<Scheme 14 Two-step procedure for conjugation of DOTA-NHS to TCO-peptide 9>>

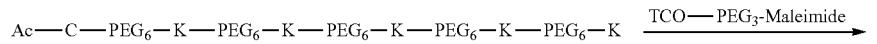

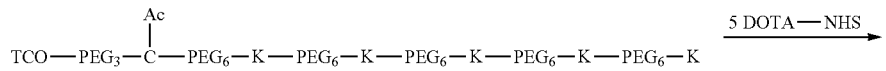

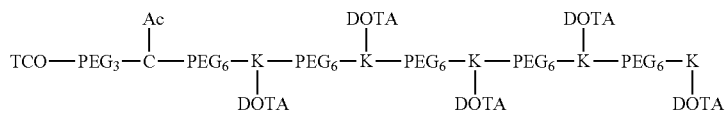

In the first step, TCO-peptide 9 was dissolved in the conjugation buffer (phosphate buffered saline, PBS, with 5 mM EDTA pH 7.0) at 1 mM. The reaction mixtures were incubated for overnight at room temperature. In the second step, the DOTA-NHS ester was added to the incubated solution at 100 mM final concentration (1:100 molar ratio or 1:20 equivalent ratio). Since the DOTA-NHS ester was acidic because of containing TFA, the pH of the solution was adjusted to 8.0 in order to activate the NHS ester-$NH_2$ coupling reaction. The reaction mixtures were incubated overnight at room temperature.

Figure 12A:
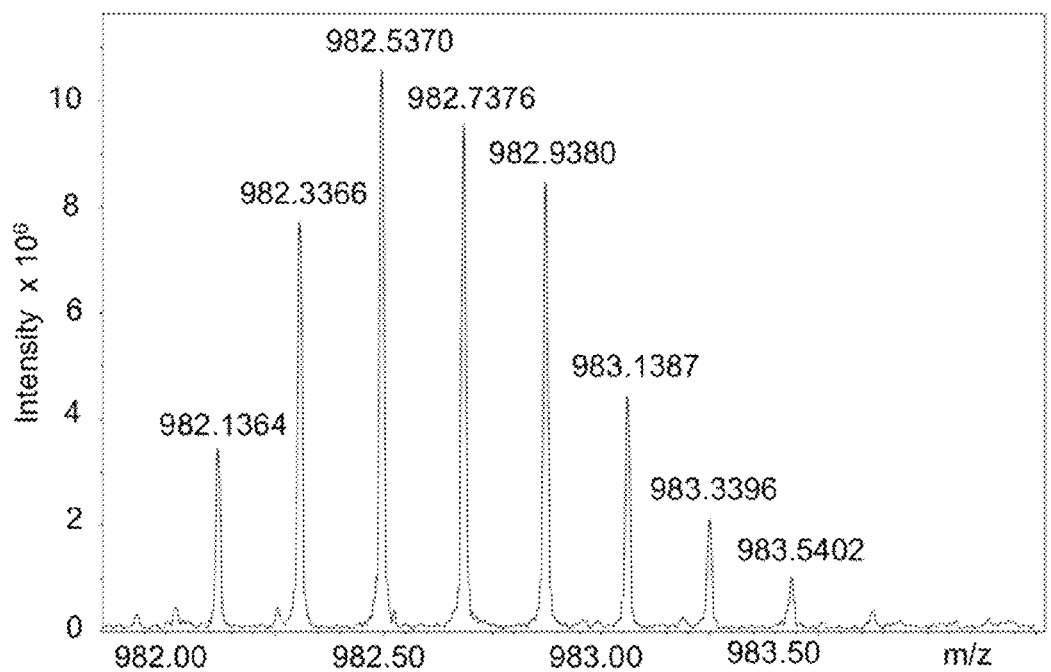
FIG. 12A shows mass spectrometry ESI-TOF result of DOTA-conjugated TCO-peptide 9.

According to the data in FIG. 12A, the present molecular construct had a m.w. of 4907.685; (ESI-TOF) m/z (z=5): $[M+3H]^+$; calculated for $C_{214}H_{38}N_{39}O_{86}S_1$ 982.5358; found 982.5370.

Example 18: Chelation of Yttrium Atoms by DOTA-Conjugated Linker Unit Based on TCO-Peptide 9

Scheme 15 showed the chelation of five $Y^{3+}$ ions by DOTA-conjugated TCO-peptide 9. Herein, $Y(NO_3)_3$ solution was added to the reaction mixtures at a 1:100 molar ratio, incubated for 2 hours at room temperature. Free DOTA-NHS and $Y^{3+}$ ions were removed from reaction mixtures by using NAP-10 Sephadex G-25 column.

<<Scheme 15 Chelation of Yttrium atom by DOTA-conjugated TCO-peptide 9>>

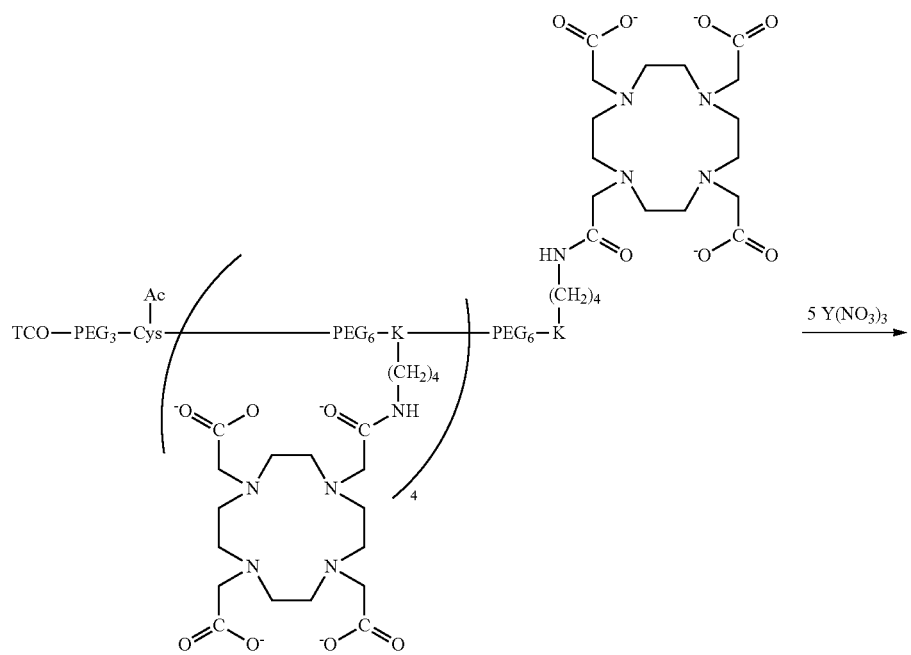

-continued

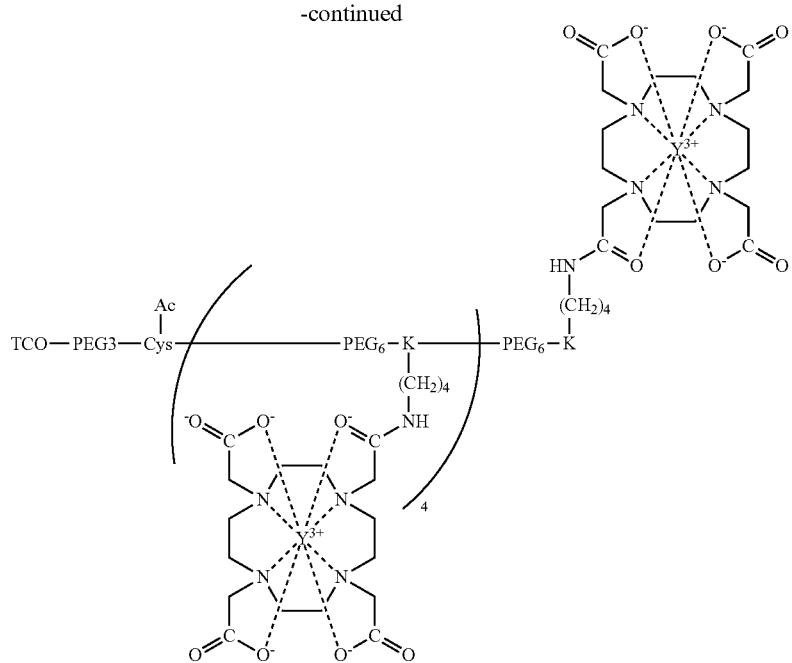

Figure 12B:
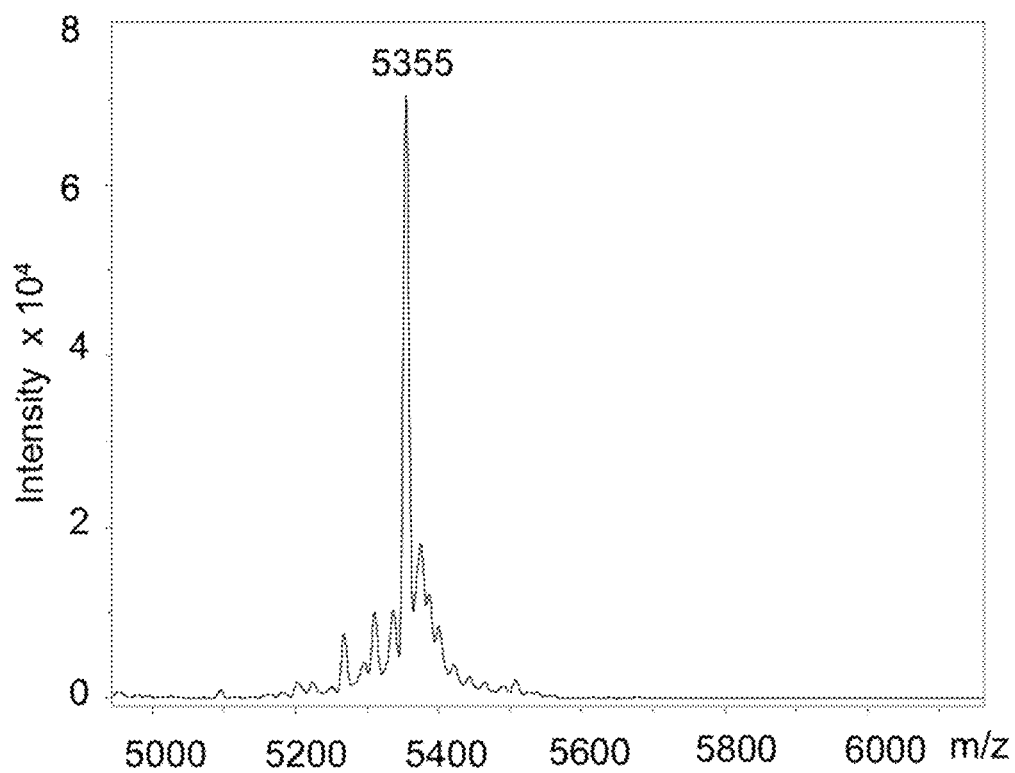
FIG. 12B shows the mass spectrometric result of $Y^{3+}$-chelated, DOTA-conjugated TCO-peptide 9.

DOTA-conjugated TCO-peptide 9 with bound $Y^{3+}$ ions was analyzed by mass spectroscopy MALDI-TOF. Mass spectrometric analysis showed that the sample of DOTA-conjugated TCO-peptide 9 with bound $Y^{3+}$ ions had a m.w. of 5355 daltons (FIG. 12B).

Illustrated below is the present drug bundle, which was composed of a linker unit with a free TCO functional group and a set of five DOTA groups respectively chelating an $Y^{3+}$ ion as effector elements.

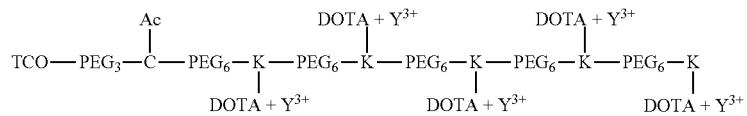

Example 19: Isolation of $V_H$ and $V_L$ Sequences from Hybridoma Cell Lines Producing Monoclonal Antibodies Respectively Specific for Human CD79a, CD79b, and Collagen VII for the Preparation of scFv Mouse B cell hybridoma 24C10 producing anti-CD79a antibody and hybridoma 1F10 producing anti-CD79b antibody were generated in our laboratory employing standard hybridoma methodology. The mouse hybridoma line LH7.2 specific for human collagen VII was a gift from Prof. Irene M. Leigh, University of Dundee, U. K. Poly(A)+ RNA was reverse-transcribed with a SuperScript III RT-PCR system (Invitrogen, Carlsbad, USA), and the first strand cDNA was synthesized. To determine the sequence of variable region of 24C10, 1F10, and LH7.2, cDNA of $V_H$ and $V_L$ were amplified by PCR using a set of DNA primers provided by Ig-primer Sets (Novagen, Madison, USA) according to the manufacturer's instructions. The sequences of $V_H$ and $V_L$ for all clones were determined.

The cDNA sequences of $V_H$ and of $V_L$ of mouse anti-human CD79a monoclonal antibody clone 24C10 are indicated in SEQ ID NO: 26 and SEQ ID NO: 27, respectively; the cDNA sequences of $V_H$ and of $V_L$ of mouse anti-human CD79b monoclonal antibody clone 1F10 are indicated in SEQ ID NO: 28 and SEQ ID NO: 29, respectively; the cDNA sequences of $V_H$ and of $V_L$ of mouse anti-human collagen VII monoclonal antibody clone LH7.2 are indicated in SEQ ID NO: 30 and SEQ ID NO: 31, respectively.

Example 20: Preparation of scFv Specific for Human CD79b or Collagen VII

To produce the scFv of anti-CD79b antibody 1F10 (SEQ ID NO: 21) and scFv of anti-human collagen VII antibody LH7.2 (SEQ ID NO: 33), DNA sequences encoding $V_L$-GSTSGSGKPGSGEGSTKG (residues 109-126 of SEQ ID NO:33)-$V_H$-SEQ ID NO:6 (GGGGS)$_2$-C were synthesized. A flexible linker GGGGSGGGGS (residues 250-259 of SEQ ID NO:33) and a cysteine residue were installed at the C-terminus of the scFv, so that the modified scFv could be subsequently linked to the maleimide group of linking arms in various linker units of this invention.

Figure 13A:
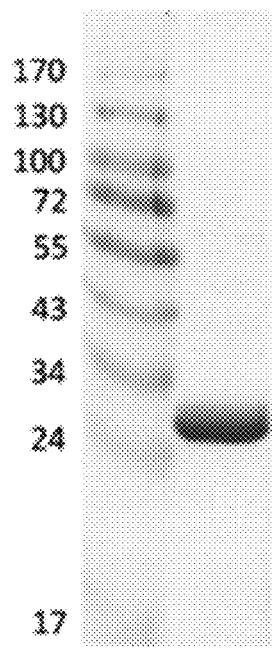
FIGS. 13A and 13B respectively show SDS-PAGE and ELISA analysis of purified scFv proteins of anti-CD79b antibody 1F10.
Figure 13B:
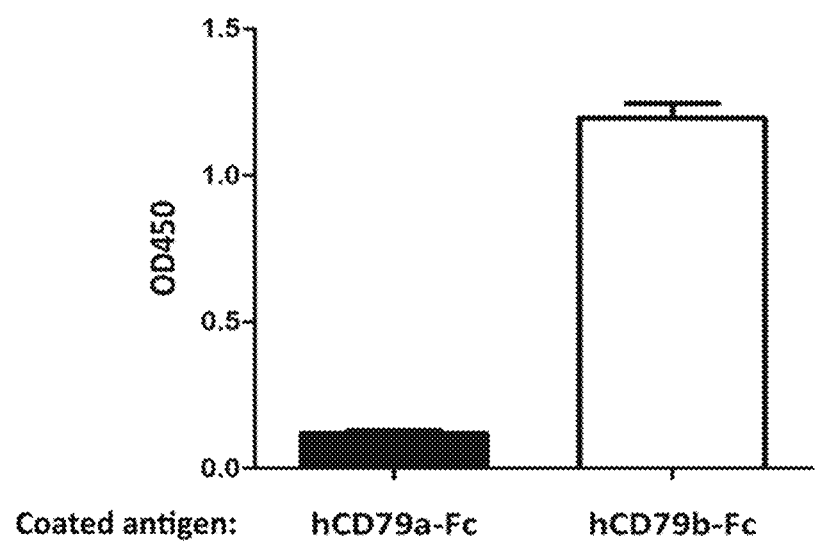
Figure 13C:
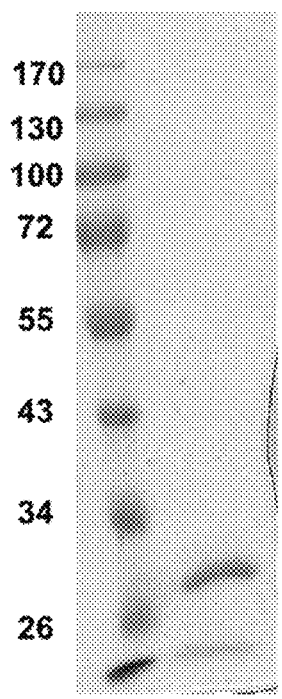
FIG. 13C and FIG. 13D respectively show SDS-PAGE and ELISA analysis of purified scFv proteins of anti-collagen VII antibody LH7.2.
Figure 13D:
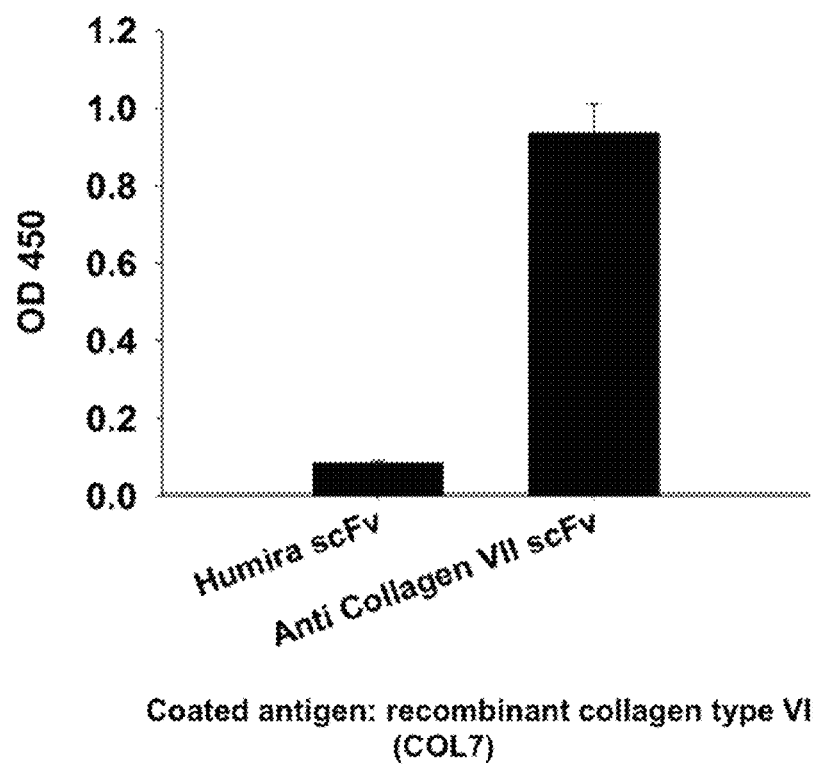

The scFv-encoding sequence was placed in pG1K expression cassette. Expi293F cells were seeded at a density of 2.0×10$^6$ viable cells/ml in Expi293F expression medium and maintained for 18-24 hours prior to transfection to ensure that cells were actively dividing at the time of transfection. On the day of transfection, 7.5×10$^8$ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for another 6 days. Culture supernatants were harvested and scFv proteins in the media were purified using Protein L affinity chromatography. FIGS. 13A and 13B respectively showed SDS-PAGE and ELISA analysis of purified scFv proteins of anti-CD79b antibody 1F10. FIG. 13C and FIG. 13D respectively showed SDS-PAGE and ELISA analysis of purified scFv proteins of anti-collagen VII antibody LH7.2.

Example 21: Production of scFv of Trastuzumab, Rituximab, Centuximab, Nivolumab, Ipilimumab, Ranibizumab, Adalimumab, and Mutated Teplizumab by HEK293 Overexpression System The scFv derived from those antibodies were designed to contain a flexible linker of GGGGSGGGGS (residues 250-259 of SEQ ID NO:33) and a terminal cysteine residue at the C-terminus. The cysteine residue provides a sulfhydryl group for conjugation with maleimide group present at the free ends of linking arms in various linker units. To produce the scFv of trastuzumab, rituximab, centuximab, nivolumab, ipilimumab, ranibizumab, adalimumab, and a mutated teplizumab, we used the $V_H$ and $V_L$ DNA sequences of those humanized antibodies without further codon optimization. DNA sequences encoding $V_L$-GSTSGSGKPGSGEGSTKG (residues 109-126 of SEQ ID NO:33)-$V_H$-SEQ ID NO:6 (GGGGS)$_2$-C were synthesized. The teplizumab antibody molecule contains a cysteine residue in CDR3 of $V_H$, which interferes with SH-maleimide conjugation explained above. We therefore prepared a mutated teplizumab substituting the cysteine residue with a serine residue. The amino acid sequences of the scFv of trastuzumab, rituximab, centuximab, nivolumab, ipilimumab, ranibizumab, adalimumab, and the mutated teplizumab, prepared for the experiments of this invention are set forth in SEQ ID NOs: 34 to 41, respectively.

For preparing scFv proteins using mammalian expression systems, we used the overexpression system based on Expi293F™ cell line for preparing 10-500 mg of scFv for experimentation. The yields were sufficient for preparing various constructs involving a specific scFv for in vitro tests and rodent animal models. The system employed ExpiFectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium (Gibco, New York, USA).

Figure 14A:
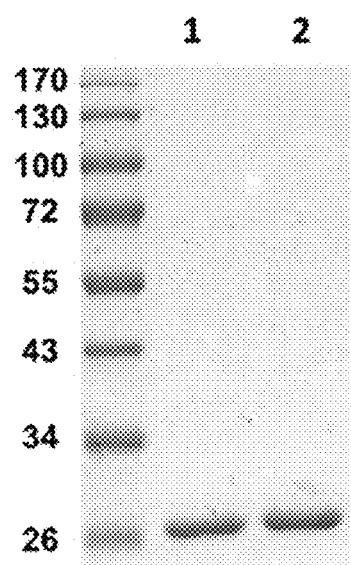
FIG. 14A shows SDS-PAGE analysis of purified scFv of trastuzumab and adalimumab.
Figure 14B:
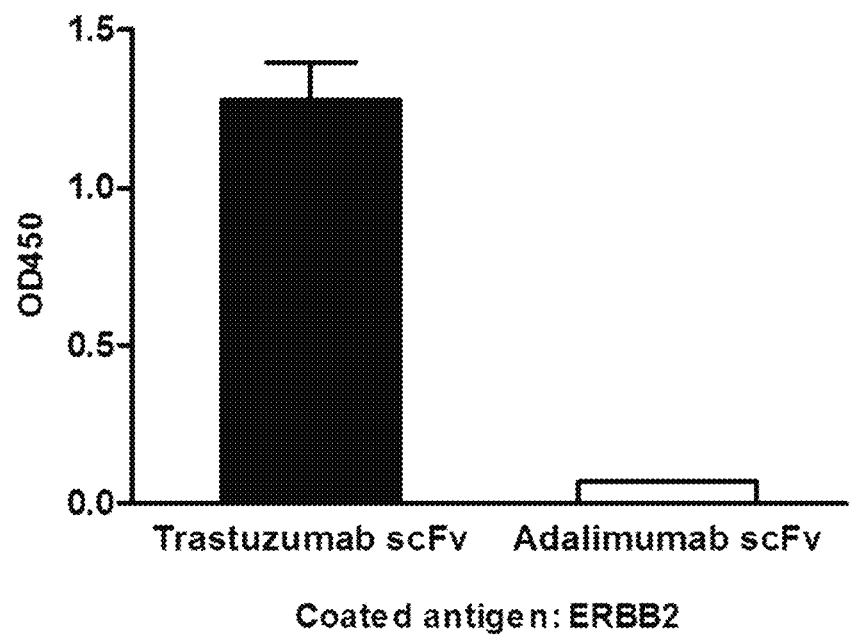
FIGS. 14B and 14C respectively show ELISA analyses of purified scFv of trastuzumab and adalimumab.
Figure 14C:
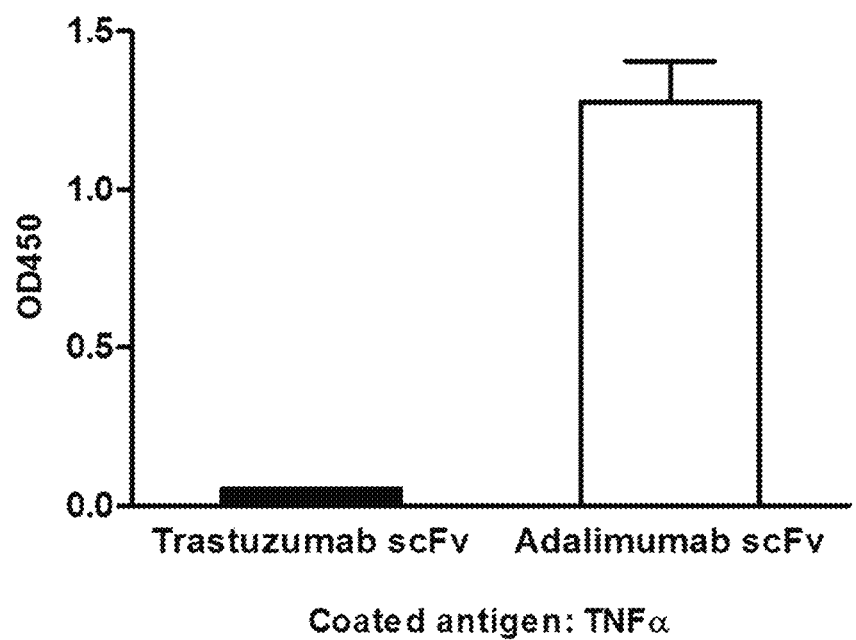
Figure 14D:
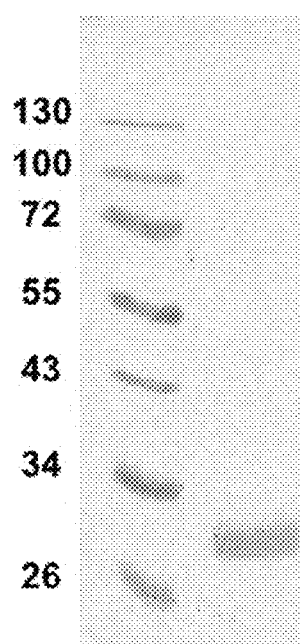
FIGS. 14D and 14E respectively show SDS-PAGE and ELISA analyses of purified scFv of centuximab.
Figure 14E:
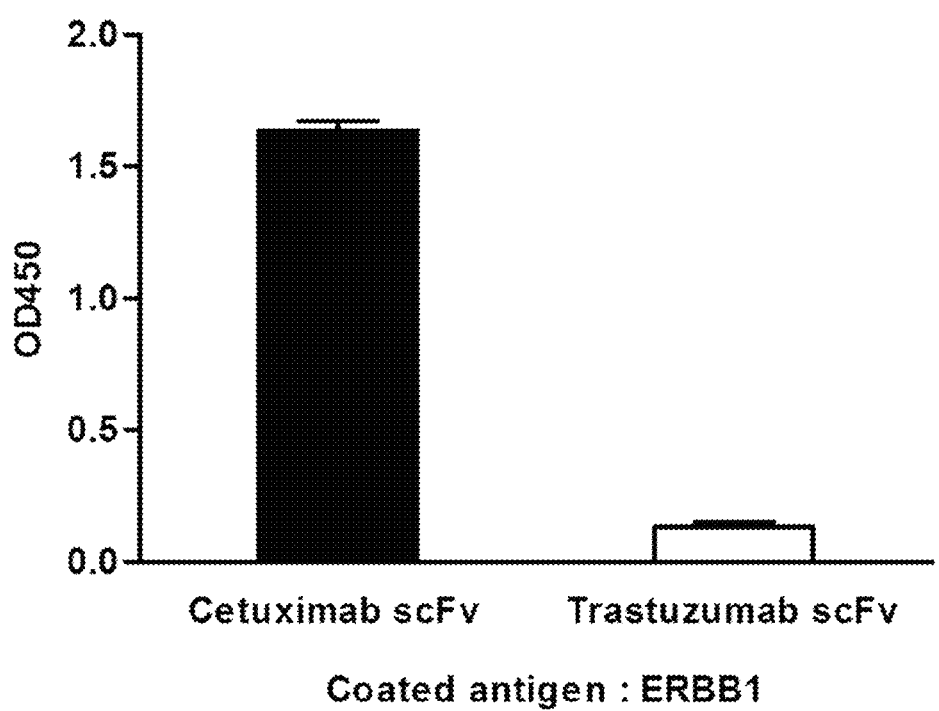

The scFv-encoding sequence was placed in pG1K expression cassette. Expi293F cells were seeded at a density of $2.0\times10^6$ viable cells/ml in Expi293F expression medium and maintained for 18 to 24 hours prior to transfection to ensure that the cells were actively dividing at the time of transfection. On the day of transfection, $7.5\times10^8$ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for another 5 to 6 days. Culture supernatants were harvested and scFv proteins in the media were purified using Protein L affinity chromatography. In our experience with adalimumab and trastuzumab scFv proteins, over 300 mg of purified scFv could be obtained from the 1 liter culture. FIG. 14A showed SDS-PAGE (10%) analysis of purified scFv of trastuzumab (lane 1) and adalimumab (lane 2), while FIGS. 14B and 14C respectively showed ELISA analyses of purified scFv of trastuzumab and adalimumab. FIGS. 14D and 14E respectively showed SDS-PAGE and ELISA analyses of purified scFv of centuximab, in which the trastuzumab scFv (anti-HER2 scFv) was used as a negative control.

Example 22: Production of scFv of Adalimumab by an Yeast *Pichia* Expression System The intended scFv constructs were the same as in the preceding Example, while the signal peptides used were different.

DNA sequence of scFv of adalimumab was synthesized and subcloned using primers (forward 5'-GTATCTCTCGA-GAAAAGAGATATTCAGATGACGCAATCCCC-3' (SEQ ID NO: 42) and reverse 5'-GTATCTGCGGCCGCT-TAACAGGAGCCACCGCCAC-3' (SEQ ID NO: 43)) containing XhoI and NotI restriction sites into pPICZα expression vector, in which the Kex2 signal peptide allowed for extracellular secretion of scFv of adalimumab. The expression plasmid was then transformed into *Pichia pastoris* by electroporation. To screen for high yield clones, ELISA was performed to measure the expression levels of scFv of adalimumab. Out of 480 transformants, five were selected for further protein induction and examination by SDS-PAGE. The clone scFv_1-A2 was selected for subsequent large-scale fermentation.

The high-yield clone scFv_1-A2 was inoculated in 100 mL of buffered glycerol-complex medium (BMGY, containing 1% yeast extract, 2% peptone, 100 mM $K_3PO_4$, 1.34 YNB, 0.4 mg/L biotin and 1% glycerol, pH 6.0) and cultured at 30° C., 200 rpm for 24 hours. On the next day, the culture was changed to a fermentation condition maintaining at 30° C., 30% of dissolved oxygen and pH 6.0. After being fermented for 24 hours, nitrogen source (YE, peptone) and methanol (0.5%, v/v) was added to induce protein expression. The culture supernatant was harvested for protein purification.

Figure 15A:
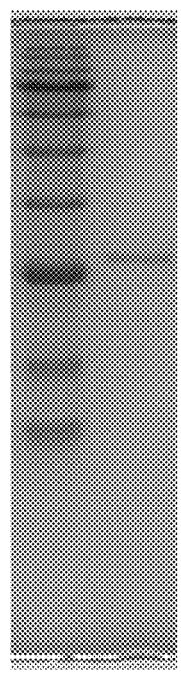
FIG. 15A shows SDS-PAGE analysis of the purified scFv of adalimumab.
Figure 15B:
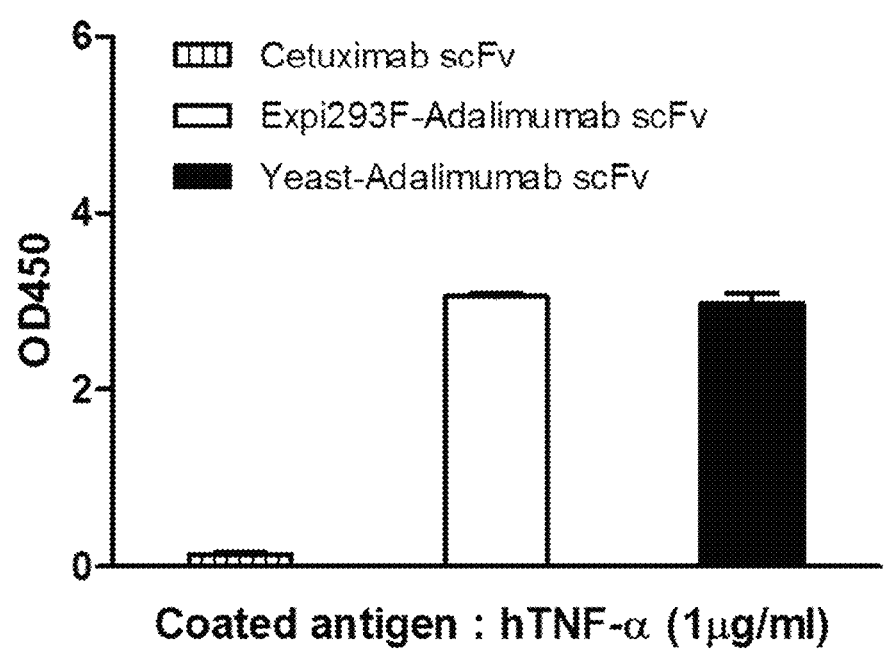
FIG. 15B shows ELISA analysis of the purified scFvs of adalimumab.

A mass spectrometric analysis showed that the scFv had a m. w. of 27296.28 daltons. FIG. 15A showed SDS-PAGE analysis of the purified scFv of adalimumab, and FIG. 15B showed ELISA analysis of the purified scFvs of adalimumab. The size of the scFv was as expected and the yeast-produced scFv of adalimumab bound to human TNF-α equally well as Expi-293F-produced scFv of adalimumab.

Example 23: Preparation of CCK Analogue

The peptide analogue of CCK (CGGGGSDY(SO$_4$H)L(N) GWL(N)DF-NH$_2$; SEQ ID NO: 44) was designed to be composed of an 8-amino acid segment of CCK with three unusual amino acid residues and a consecutive N-terminal extension of six amino acid residues (CGGGGS, residues 1-6 of SEQ ID NO:44) with a cysteine residue at the terminal. The tyrosine residue (Y) was sulfated at its OH group on the aromatic ring and L(N) was a norleucine residue. The cysteine residue provided an SH group for conjugation with PEG-maleimide linking arms of the linker unit according to the present disclosure. The peptide was custom-synthesized by Kelowna Inc., Taipei, Taiwan.

Example 24: Preparation of TCO- and DBCO-scFv Specific for CD3

The DNA sequence encoding SEQ ID NO: 41 was synthesized and expressed as in the above Examples. The sequences of $V_L$ and $V_H$ of scFv specific for CD3 were those of $V_L$ and $V_H$ of mutated Teplizumab. For the conjugation with Mal-PEG$_3$-TCO and Mal-PEG$_5$-DBCO (Conju-probe, Inc.), the cysteine residue at the C-terminal end of the purified scFv of the mutated teplizumab was reduced by incubating 5 mM DTT at room temperature for 4 hours with gentle shaking. The buffer of reduced anti-CD3 scFv was exchanged to sodium phosphate buffer (100 mM sodium phosphate, pH7.0, 50 mM NaCl, and 5 mM EDTA) by using NAP-10 Sephadex G-25 column. After the reduction reaction and buffer exchange, conjugation was conducted overnight at room temperature in a reaction molar ratio of 1:1 ([Mal-PEG$_3$-TCO or Mal-PEG$_5$-DBCO:[scFv]]. The excess crosslinker was removed by a desalting column and the TCO-conjugated and DBCO-conjugated scFv products were analyzed.

Figure 16A:
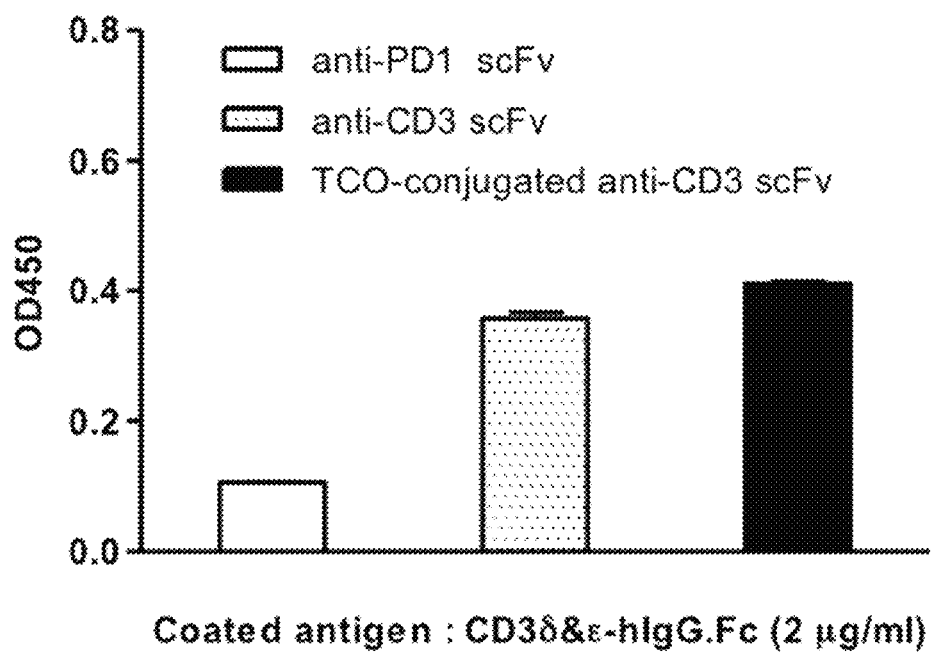
FIG. 16A and FIG. 16B show, respectively, the ELISA analysis of TCO-conjugated scFv and DBCO-conjugated scFv specific for CD3.
Figure 16B:
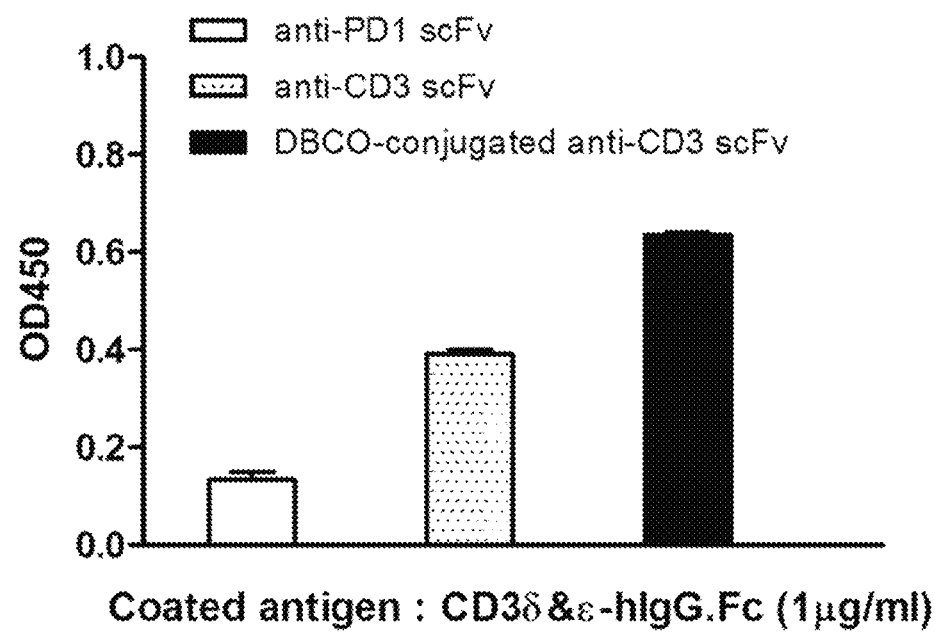

The results of mass spectroscopy MALDI-TOF analysis indicated that the sample of TCO-conjugated scFv specific for CD3 had a m.w. of 28053 daltons; while the sample of DBCO-conjugated scFv specific for CD3 had a m.w. of 28178 daltons. The purity of TCO-conjugated scFvs specific for CD3 was identified through Coomassie staining of 12% SDS-PAGE (data not shown). FIG. 16A and FIG. 16B show, respectively, the ELISA analysis of TCO-conjugated scFv and DBCO-conjugated scFv specific for CD3, in which anti-PD1 scFv and anti-CD3 scFv were used as a negative control and positive control, respectively. According to the ELISA results, both TCO-conjugated scFv and DBCO-conjugated scFv specific for CD3 bound to CD3-Fc-fusion protein.

Example 25: Conjugation of Three scFvs Specific for CD79b to Three PEG$_{12}$-Maleimide Linking Arms Based on Tetrazine-Peptide 2

This example aimed to demonstrate that three scFvs could be conjugated to the three PEG$_{12}$-maleimide linking arms based on tetrazine-peptide 2. Prior to conjugation with the tetrazine-peptide 2 that had three PEG$_{12}$-maleimide linking arms, 1F10 scFv was incubated with DTT at a molar ratio of 2:1 ([DTT]:[scFv]) at 25° C. for 4 hours with gentle shaking to keep its C-terminal cysteine in reduced form. Subsequently, the buffer of reduced 1F10 scFv was exchanged to maleimide-SH coupling reaction buffer (100 mM sodium phosphate, pH 7.0, 50 mM NaCl and 5 mM EDTA) by using an NAP-10 Sephadex G-25 column (GE Healthcare). After the reduction and buffer exchange, the conjugation to the tetrazine-peptide 2 having three PEG$_{12}$-maleimide linking arms was conducted overnight at 4° C. at a molar ratio of 1:4 ([linker]:[Protein]).

Example 26: Purification of the Targeting Linker Unit Containing Three scFvs Specific for CD79b Linked to the Three PEG$_{12}$-Maleimide Linking Arms Based on Tetrazine-Peptide 2

Figure 17A:
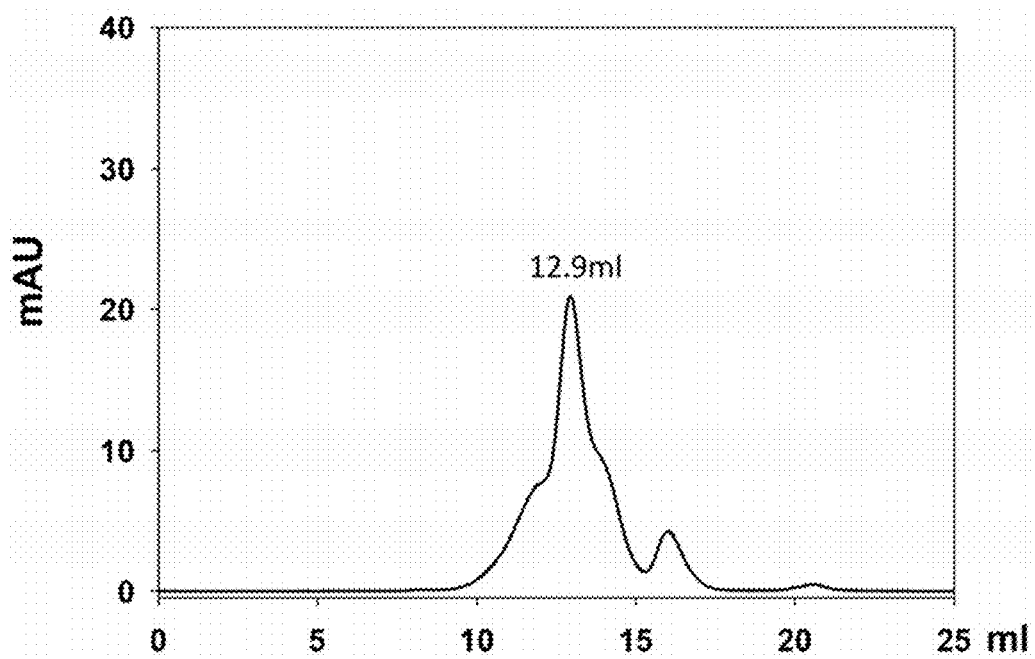
FIG. 17A is the FPLC elution profile on a synthesized linker unit composed of a free tetrazine functional group and a set of three scFvs specific for human CD79b.
Figure 17B:
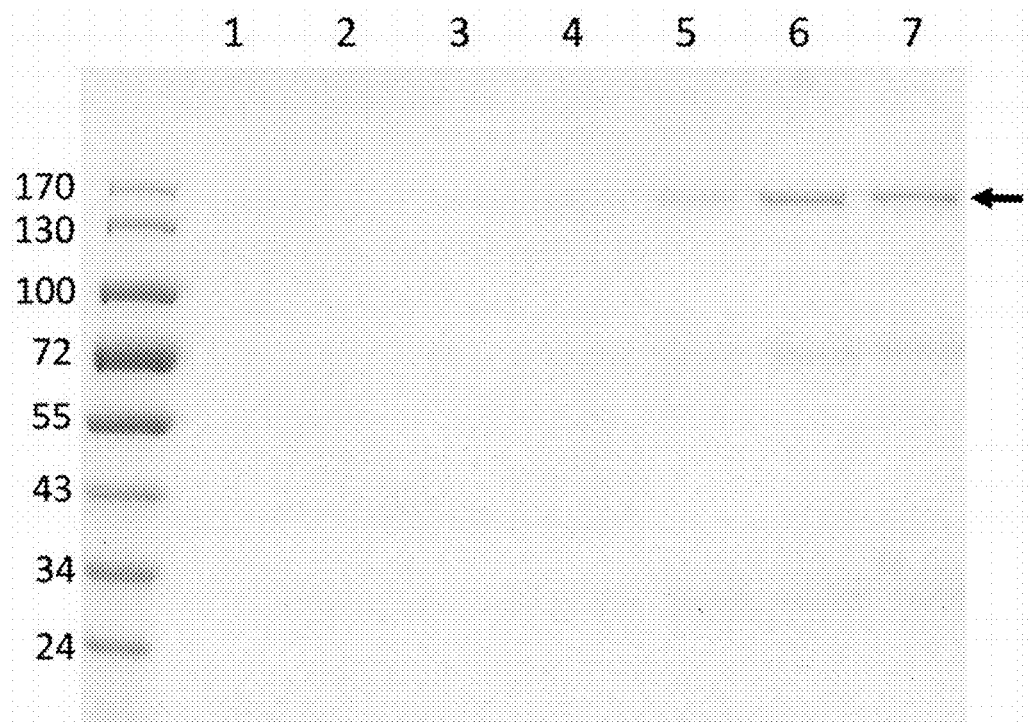
FIG. 17B shows the SDS-PAGE analysis result.

The reaction mixture of the preceding example was applied to a size exclusion chromatography column S75. The PEG$_{12}$-maleimide-conjugated tetrazine-peptide 2 conjugated with three scFvs specific for CD79b was separated from the free scFv, free PEG$_{12}$-maleimide-conjugated tetrazine-peptide 2 and the PEG$_{12}$-maleimide-conjugated tetrazine-peptide 2 conjugated with 1 and two scFvs specific for CD79b by size exclusion chromatography column S75. FIG. 17A was the FPLC elution profile on a synthesized targeting linker unit composed of a linker unit with a free tetrazine functional group and a set of three scFvs specific for human CD79b as targeting elements. The product (i.e., the PEG$_{12}$-maleimide-conjugated tetrazine-peptide 2 having a free tetrazine functional group and being conjugated with a set of three scFvs specific for CD79b) was purified in the elution fractions and shown in lane 5 to 7 of the 10% SDS-PAGE analysis shown in FIG. 17B.

Figure 17C:
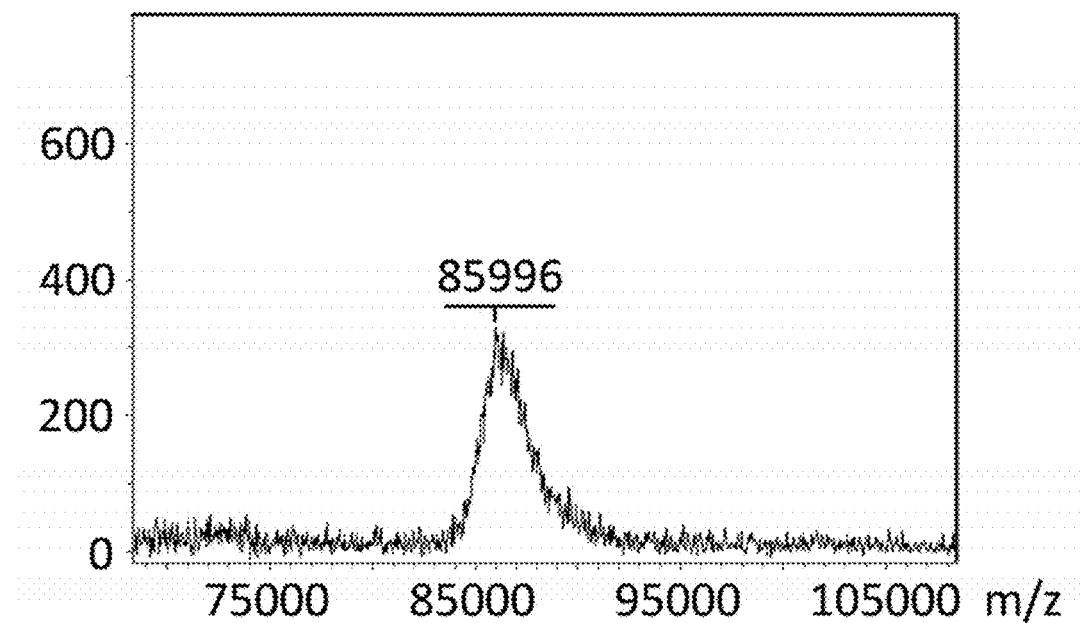
FIG. 17C shows the mass spectrometry MALDI-TOF result.

Example 27: Analysis of Targeting Linker Unit Containing Three scFvs Specific for CD79b Linked to the Three PEG$_{12}$-Maleimide Linking Arms Based on Tetrazine-Peptide 2 by Mass Spectrometry MALDI-TOF The sample of the targeting linker unit of three scFvs specific for CD79b linked to the three PEG$_{12}$-maleimide linking arms based on tetrazine-peptide 2 was confirmed by using mass spectrometry MALDI-TOF. The median of experimental molecular weight was consistent with the median of theoretical molecular weight of three 1F10 scFv conjugated to tetrazine-peptide 2 with three PEG$_{12}$-maleimide linking arms. According to the mass spectrometric profile in FIG. 17C, the present targeting linker unit had the median molecular weight of 85996 daltons. Illustrated below is the present targeting linker unit that was composed of a linker unit with a free tetrazine functional group and a set of three scFvs specific for human CD79b as targeting elements.

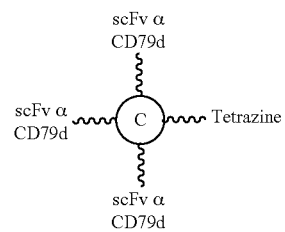

Figure 18A:
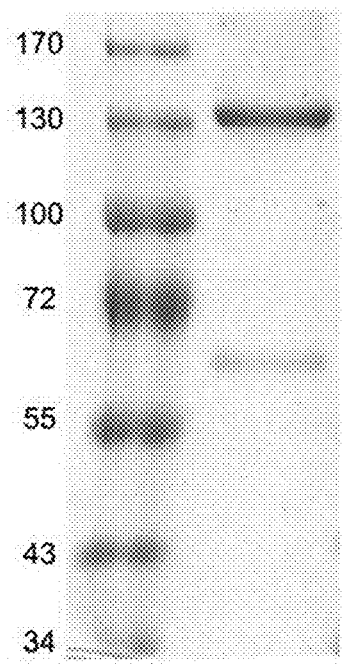
FIG. 18A and FIG. 18B respectively show the SDS-PAGE and mass spectrometry analysis result of tetrazine-peptide 2 conjugated with three scFvs specific for HER2/neu.
Figure 18B:
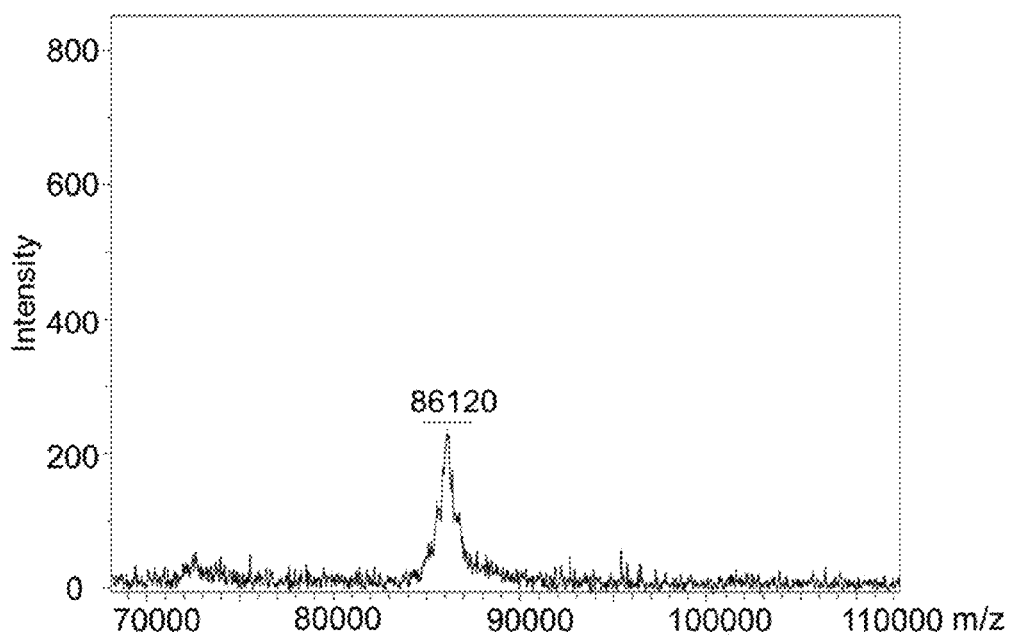

Example 28: Preparation of Targeting Linker Unit Based on Tetrazine-Peptide 2 with Three scFvs Specific for HER2/Neu The conjugation of scFv to the linker unit of prepared in an earlier Example and the purification and analysis of the product were the same as described in the preceding Examples. FIG. 18A showed the SDS-PAGE analysis of the synthesized product, indicating that the preparation was relatively pure. However, molecules with substantial PEG component generally migrate slowly in SDS-PAGE than proteins with the same molecular weight. FIG. 18B showed the mass spectrometric analysis, indicating that the purified linker unit had a m.w. of 86120 daltons. Illustrated below is the present targeting linker unit, which was composed of a linker unit with one free tetrazine functional group and a set of three scFvs specific for human HER2/neu as targeting elements.

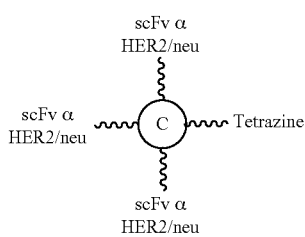

Example 29: Preparation of Effector Linker Units Based on TCO-Peptide 2 with Three scFvs Specific for TNF-α or PD-1

The conjugation of scFv to the linker unit prepared and the purification and analysis of the product were the same as the preceding Examples.

Figure 18C:
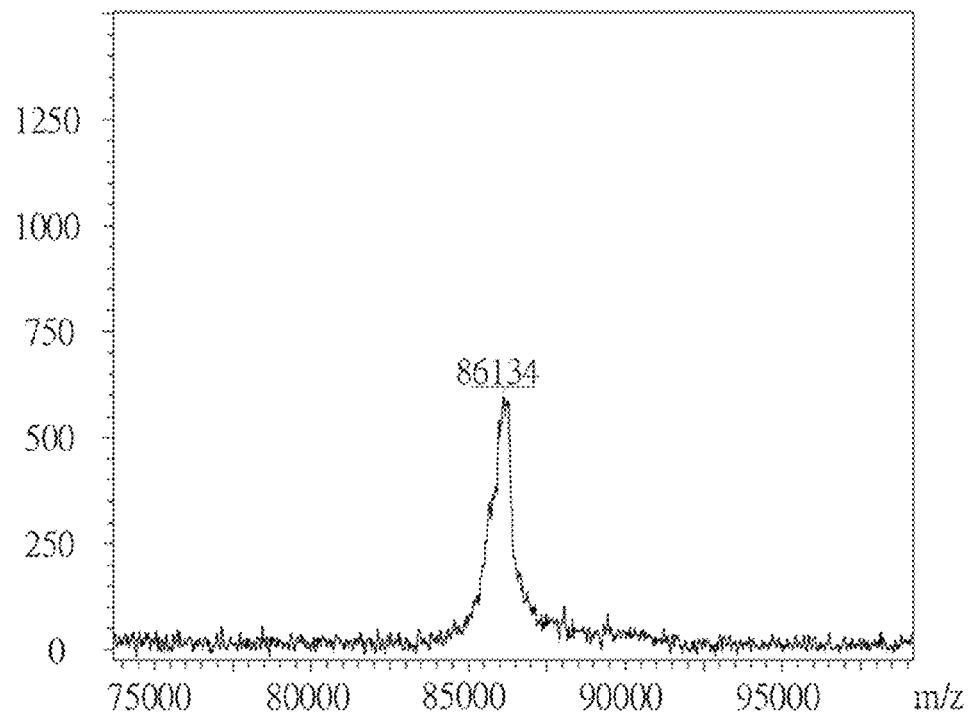
FIG. 18C shows the mass spectrometry result of TCO-peptide 2 conjugated with three scFvs specific for TNF-.

Shown in FIG. 18C was the mass spectrometric analysis of the present effector linker unit that was composed of a linker unit with a free TCO functional group and a set of three scFv specific for human TNF-α as effector elements (illustrated below). As indicated in FIG. 18C, this effector linker unit had a molecular weight of 86134 daltons.

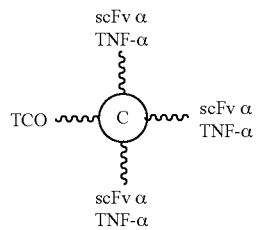

Figure 18D:
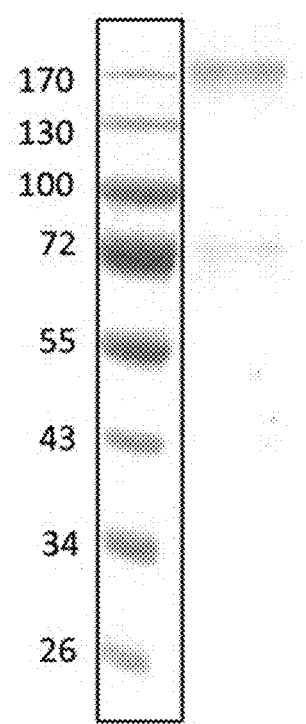
FIGS. 18D and 18E respectively show the SDS-PAGE and mass spectrometry analysis of TCO-peptide 2 conjugated with three scFvs specific for PD-1.
Figure 18E:
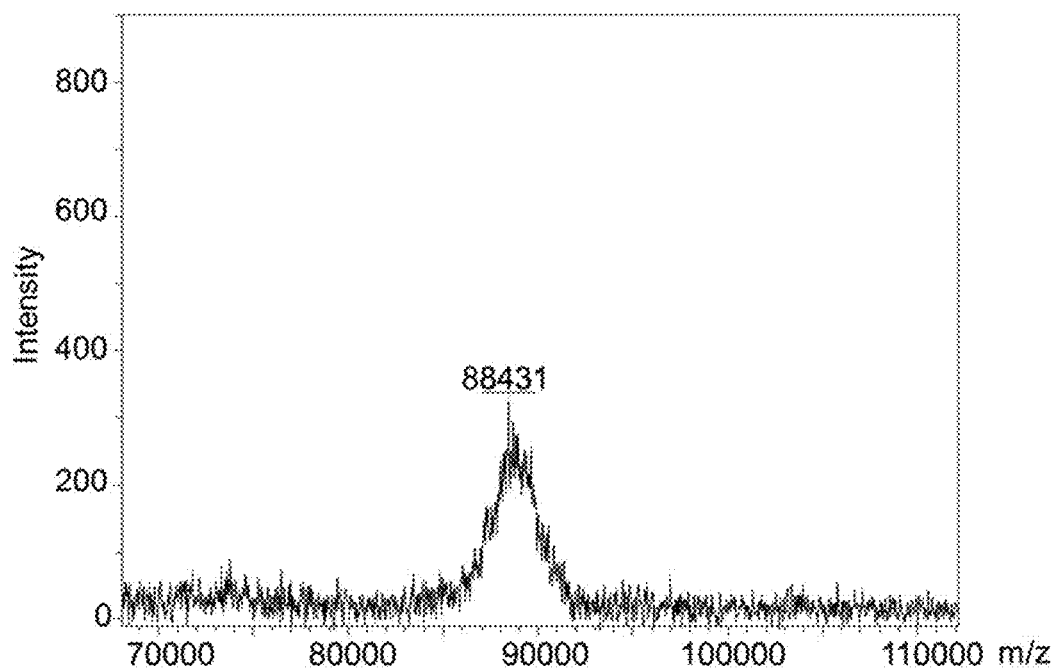

FIG. 18D and FIG. 18E respectively showed SDS-PAGE and mass spectrometric analyses of another effector linker unit that had one free TCO functional group and a set of three scFvs specific for human PD-1 as effector elements (illustrated below). As indicated in FIG. 18E, this effector linker unit had a molecular weight of 88431 daltons.

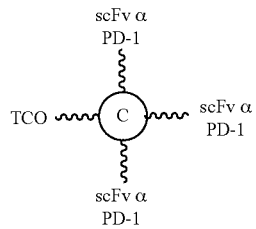

Figure 19:
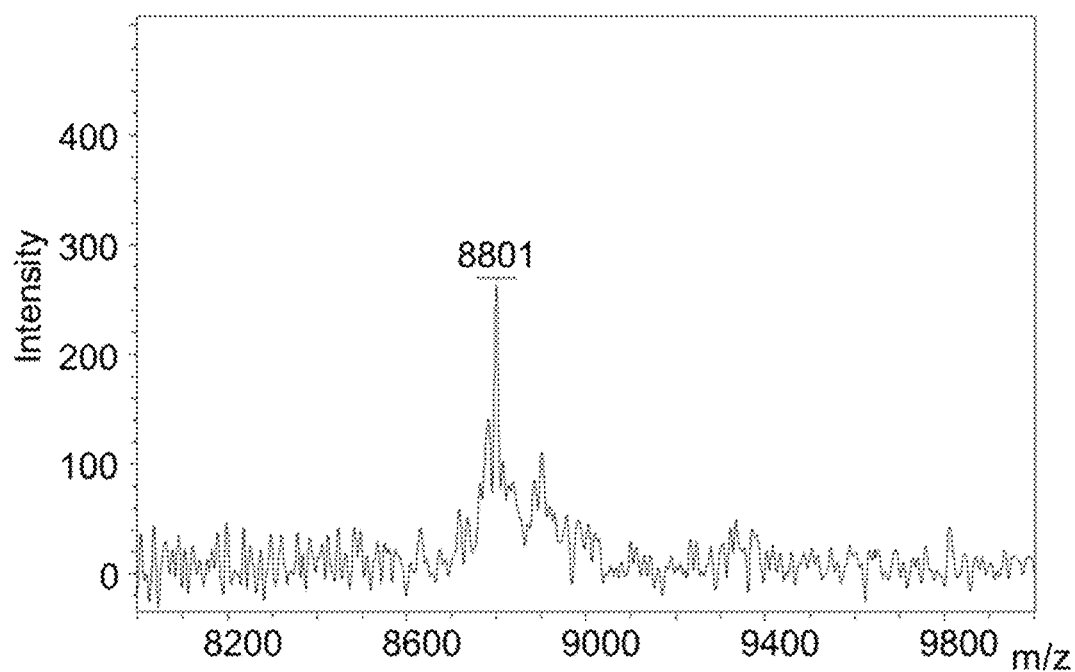
FIG. 19 shows mass spectrometry analysis result of tetrazine-peptide 2 conjugated with 3 CCK peptides.

Example 30: Preparation of Targeting Linker Unit Based on Tetrazine-Peptide 2 with Three CCK Peptide Molecules The CCK peptide was prepared in an earlier Example. The conjugation of the peptide to the 3-arm linker was performed as described in the preceding Examples. Mass spectrometric analysis showed that the linker unit with three CCK peptides had a m.w. of 8801 daltons (FIG. 19). Specifically, this targeting linker unit was composed of a linker unit with a free tetrazine functional group and a set of three CCK peptides as targeting elements.

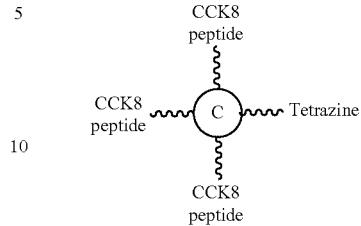

Example 31: Preparation of Targeting Linker Unit Based on TCO-Peptide 7 with Two scFvs Specific for CD20

In this example, a linker unit with two functional groups for conjugating with different linker units was prepared. This targeting linker unit served as the center linker unit in a molecular construct with three linker units, which comprised two targeting linker units and one effector linker unit. In our design, the two targeting linker units were joined via iEDDA reaction between the tetrazine and TCO groups, while the center linker unit and the effector linker unit were joined via CuAAC reaction between the alkyne and azide groups.

Figure 20:
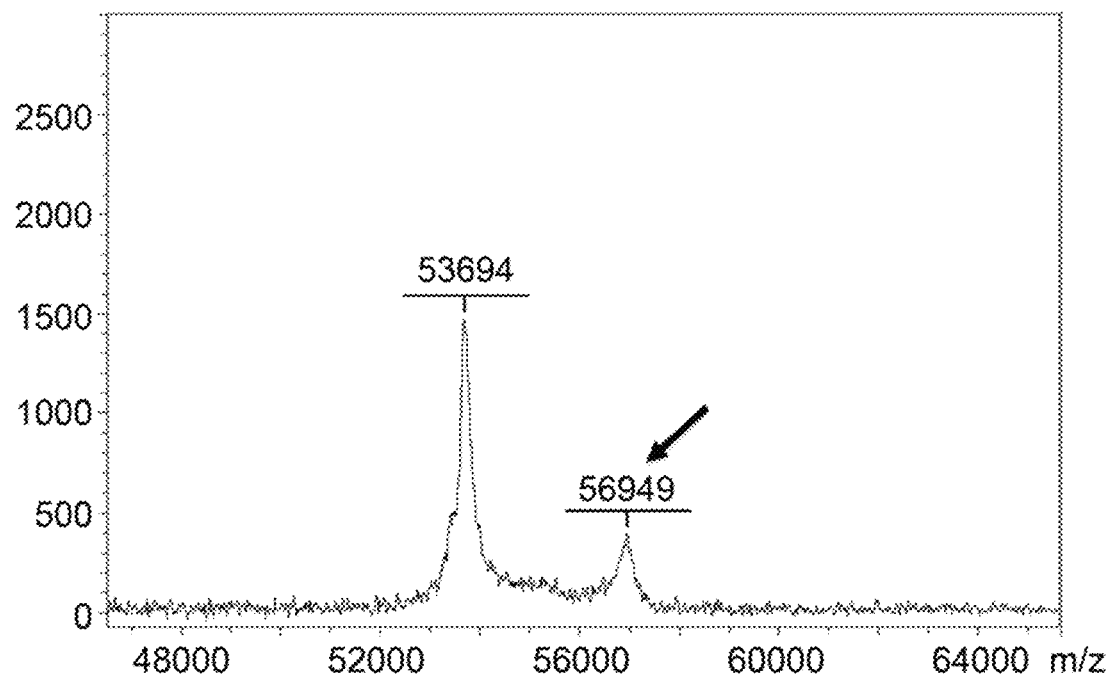
FIG. 20 shows mass spectrometry analysis result of TCO-peptide 7 conjugated with two scFvs specific for CD20.

The conjugation of scFvs to the linker unit prepared in an earlier Example and the purification and analysis of the product were the same as described in preceding Examples. The resultant targeting linker-unit (illustrated below) was composed of a linker-unit with a free TCO functional group, a free alkyne group, and a set of two scFvs specific for human CD20 as targeting elements. The mass spectrometric analysis provided in FIG. 20 indicated that such targeting linker unit had m.w. of 56949 daltons (indicated with an arrow).

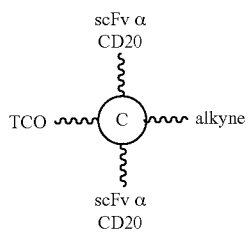

Example 32: Conjugation of Two scFvs Specific for VEGF-A to Linker Unit with One Free TCO Group and Two PEG Linking Arms with Maleimide Groups The conjugation of scFv to the linker unit prepared in an earlier Example and the purification and analysis of the product were the same as described in preceding Examples.

Figure 21:
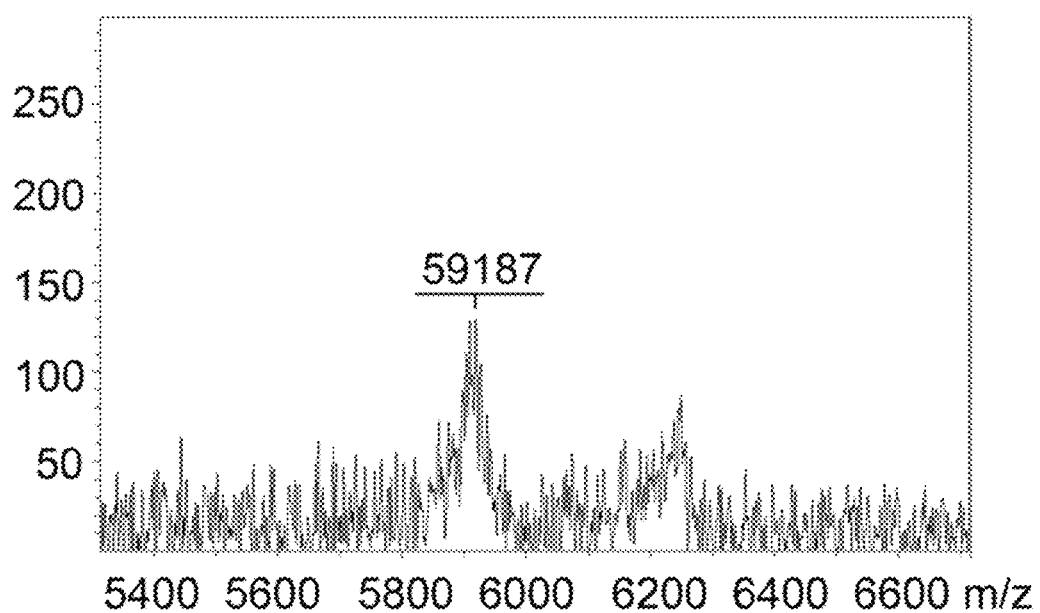
FIG. 21 shows mass spectrometry analysis result of TCO-peptide 1 conjugated with two scFvs specific for VEGF-A.

Illustrated below is the resultant linker unit, an effector linker-unit being composed of a linker unit with a free TCO functional group and a set of two scFvs specific for human VEGF-A as effector elements. The mass spectrometric analysis indicated that this linker unit had a m.w. of 59187 daltons (FIG. 21).

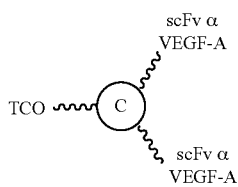

Example 33: Preparation of Molecular Construct with Three scFv Specific for CD79b as Targeting Element and One scFv Specific for CD3 as Effector Element In this example, the targeting linker unit of the preceding examples and a TCO-scFv specific for CD3 were coupled via tetrazine-TCO iEDDA reaction. Specifically, the targeting linker unit had three scFv specific for CD79b and one free tetrazine group.

Figure 22A:
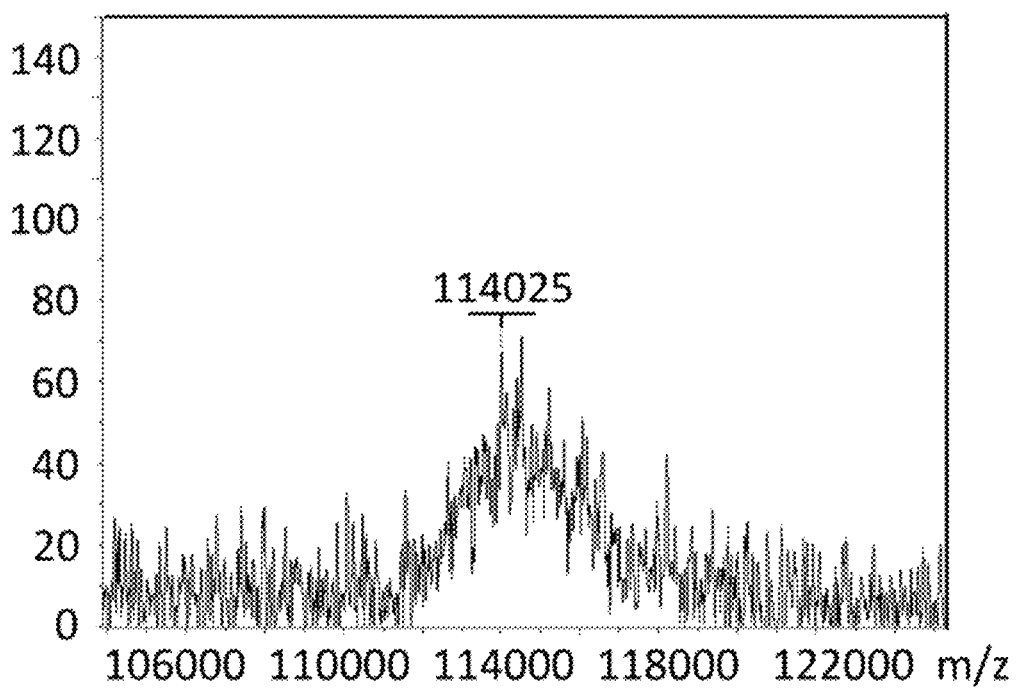
FIG. 22A shows the mass spectrometry analysis result of a molecular construct with three scFvs specific for CD79b and one scFv specific for CD3.

The procedure for tetrazine-TCO ligation was performed per the manufacturer's instructions (Jena Bioscience GmbH, Jena, Germany). Briefly, 113 μl of the targeting linker unit (12.4 mg/ml) was added to the solution containing the effector unit at a molar ratio of 1:2 ([tetrazine]:[TCO]). The reaction mixture was incubated for 3 hours at room temperature. The product was subjected to mass spectrometric analysis, and the result indicated a molecular weight of 114025 daltons (FIG. 22A).

The product, a single linker unit molecular construct with three scFvs specific for CD79b as targeting elements and one scFv specific for CD3 as an effector element, is illustrated below.

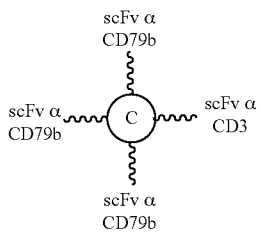

Example 34: Preparation of Molecular Construct with Three scFvs Specific for HER2/Neu as Targeting Element and One scFv Specific for CD3 as Effector Element The targeting linker unit prepared in an earlier Example and the TCO-scFv specific for CD3 were coupled via the tetrazine-TCO iEDDA reaction.

Figure 22B:
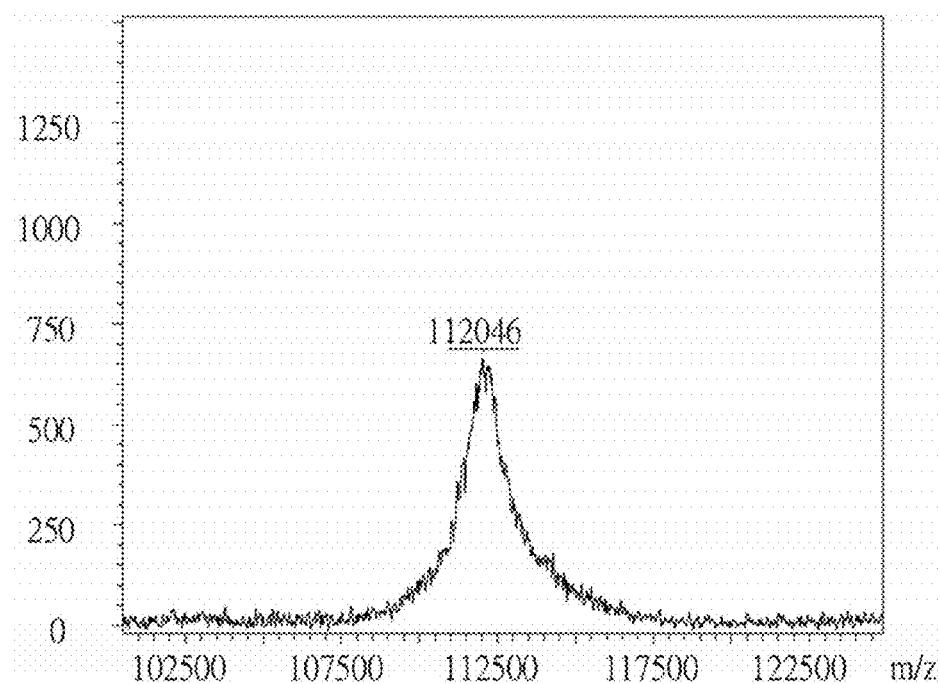
FIG. 22B shows the mass spectrometry analysis result of a molecular construct with three scFvs specific for HER2/neu and one scFv specific for CD3.

The procedure for tetrazine-TCO ligation was performed as described in the previous Example. The product, as illustrated below, was a single linker unit molecular construct with three scFvs specific for HER2/neu as targeting elements and one scFv specific for CD3 as an effector element. The mass spectrometric analysis shown in FIG. 22B indicated that this molecular construct had a molecular weight of 112046 daltons.

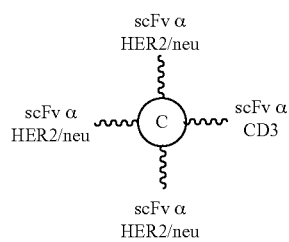

Figure 23:
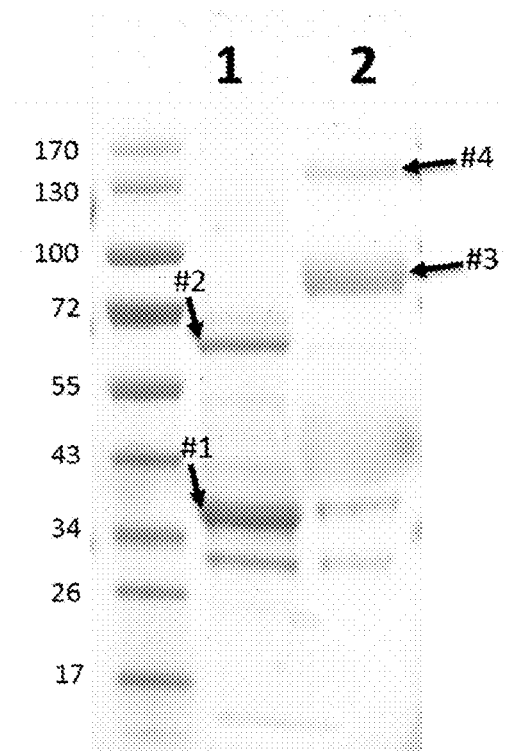
FIG. 23 shows the SDS-PAGE analysis of the reaction mixtures of TCO-peptide 1 after the conjugation with scFv of anti-VEGF-A and further with tetrazine-20 kDa PEG.

Example 35: Preparation of Molecular Construct with Effector Linker Unit with Two scFvs Specific for VEGF-A and Long-Chain PEG The long-chain PEG (linear, 20 kDa) with a tetrazine group at one end was purchased from Click Chemistry Tools (Scoottsdale, Pa., USA). The coupling of the effector linker unit and tetrazine-long-chain PEG were coupled by an iEDDA reaction using a protocol similar to that described in the above Example. FIG. 23 showed the SDS-PAGE analysis of the reaction mixtures of TCO-peptide 1 after the conjugation with scFv of anti-VEGF-A (lane 2) and further with tetrazine-20 kDa PEG (Lane 2). Arrow #1 and #2 were respectively TCO-peptide 1 conjugated with one and two scFvs of anti-VEGF-A; arrow #3 and #4 were respectively TCO-peptide 1 conjugated with one and two scFvs of anti-VEGF-A, as well as one tetrazine-20 kDa PEG chain.

Illustrated below is the present molecular construct with two scFvs of anti-VEGF-A and one 20 kDa PEG chain.

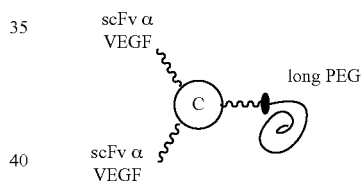

Example 36: Assay of Biological Activity of LPS Upon the Conjugation to Peptide Core Through Linking Arm To test the LPS biological activity of linker unit conjugated with LPS, TLR 4 stimulation cell-based assay was performed using HEK-Blue™ detection kit (InvivoGen, San Diego, USA) according to manufacturer's instruction. HEK-Blue™ hTLR4 cells express two human genes, TLR4 and MD-2/CD14 co-receptor genes, and contain the secreted embryonic alkaline phosphatase (SEAP) reporter gene for monitoring nuclear factor (NF)-κB activation. Upon interaction with the TLR4 agonist, TLR4 transduces a signal to trigger the activation of NF-κB and to express secreted alkaline phosphatase, which can be detected by using detection medium (HEK-Blue™ detection, a medium used for the quantification of secreted alkaline phosphatase; InvivoGen) and measured with a spectrophotometer.

Briefly, HEK-hTLR4 cells were cultured at a density of $2.5 \times 10^4$ cells in 96-well plates and maintained in complete DMEM with selective antibiotics, normocin. Cells were stimulated with different concentrations (2-fold dilutions from 100 μg/ml) of crude LPS, purified LPS, dansyl hydrazine modified LPS, and the LPS conjugated to peptide core for 18 hours. The activation of TLR4 was analyzed by measuring SEAP from the culture medium using a spectrophotometer at 620 nm.

Figure 24:
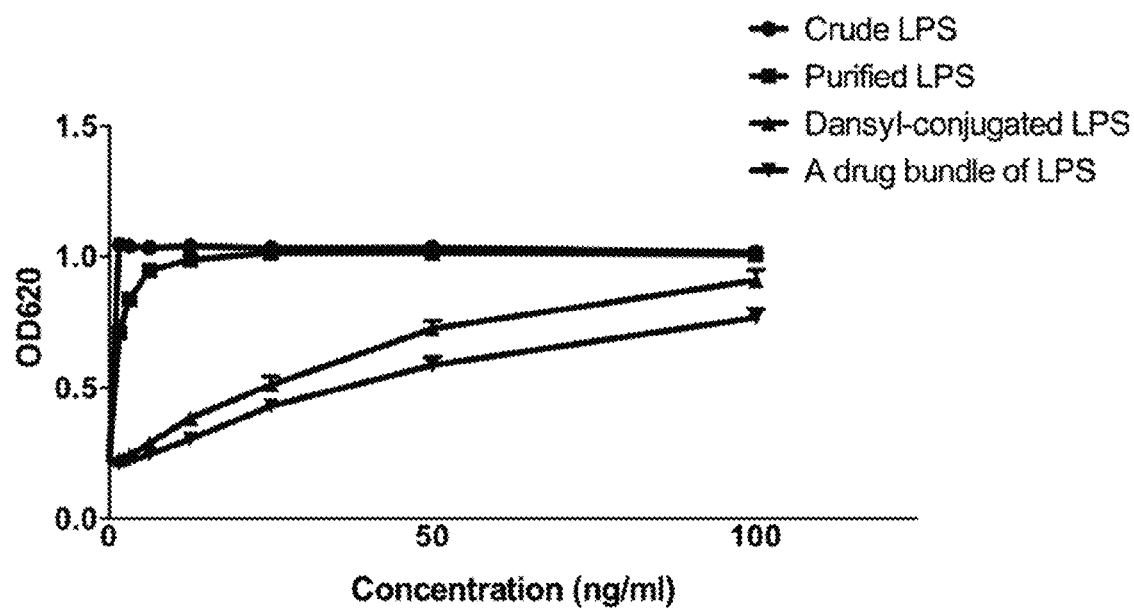
FIG. 24 shows the assay results of the biological activity of LPS, before and after modification with dansyl hydrazine.

FIG. 24 showed the assay results of the biological activity of LPS, before and after modification. The LPS fraction suitable for the modification with dansyl hydrazine was purified, which had a biological activity that was similar to the crude LPS. Dansyl hydrazine-modified LPS and the LPS conjugated to peptide core had comparable partial activities.

Example 37: Assay of Biological Activity Imiquimod Upon the Conjugation to Peptide Core Through Linking Arm To test the biological activity of $PEG_5$-NHS conjugated with imiquimod, TLR 7 stimulation cell-based assay was performed using HEK-Blue™ detection kit (InvivoGen, San Diego, USA) per the manufacturer's instruction. HEK-Blue™ hTLR7 cells express two human genes, TLR7 receptor gene and an secreted embryonic alkaline phosphatase (SEAP) reporter gene. Upon interaction with the TLR7 agonist, TLR7 transduces a signal to trigger the activation of NF-κB and to express secreted alkaline phosphatase, which can be detected by using detection medium (HEK-Blue™ detection, a medium used for the quantification of secreted alkaline phosphatase; InvivoGen) and measured with a spectrophotometer.

Briefly, HEK-hTLR7 cells were cultured at a density of $4\times10^4$ cells in 96-well plates and maintained in complete DMEM with selective antibiotics, normocin. Cells were stimulated with different concentrations (2-fold dilutions from 20 μg/ml) of imiquimod and the $PEG_5$-NHS conjugated with imiquimod for 18 hours. The activation of TLR7 was analyzed by measuring SEAP from the culture medium using a spectrophotometer at 620 nm.

Figure 25:
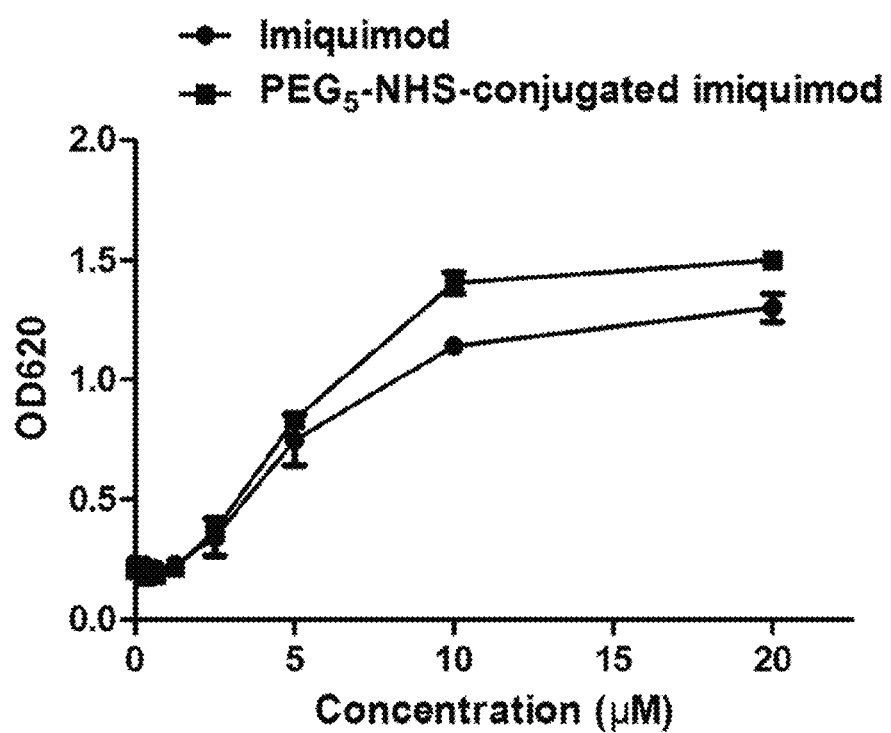
FIG. 25 shows the assay results of the biological activity of imiquimod upon the conjugation with PEG linking arm.

FIG. 25 showed the assay results of the biological activity of imiquimod upon the conjugation with linking arm, indicating that the imiquimod molecule conjugated with a linking arm had similar biological activity as the unmodified imiquimod.

Example 38: Pharmacokinetic Properties of Molecular Construct with Two scFv of Anti-VEGF-A and One 20 kDa PEG in Balb/c Mice Balb/c mice, female, 10-week old, were used for this study. The scFv comprised in the molecular constructs was derived from ranibizumab, as prepared in an earlier example. Briefly, 100 μg of scFv of anti-VEGF-A and a linker unit with two scFvs anti-VEGF-A and one 20 kDa PEG in 100 ml PBS were respectively injected into the mice via a tail vein. Blood samples were collected via orbital sinus bleeding at 2, 4, 24, 48, and 72 hours after the injection. The blood was allowed to clot, and the sera were collected. The concentration of anti-VEGF-A activity was assayed by ELISA using a 96-well plate coated with huVEGF-A recombinant protein in 2 μg/ml concentration, 50 μl per well. 100 μl aliquots of serum diluted in PBS containing 1% BSA and 1% skim milk were added into the wells and incubated at 37° C. for 2 hours. 100 μl HRP-conjugated protein L diluted in PBS at a ratio of 1:2000 was then added and incubated at 37° C. for 1 hour. Next, 50 μl of TMB substrate was added for color development. The reaction was stopped by 50 μl of 1M HCl. Absorbance at 450 nm was measured with a plate reader.

Figure 26:
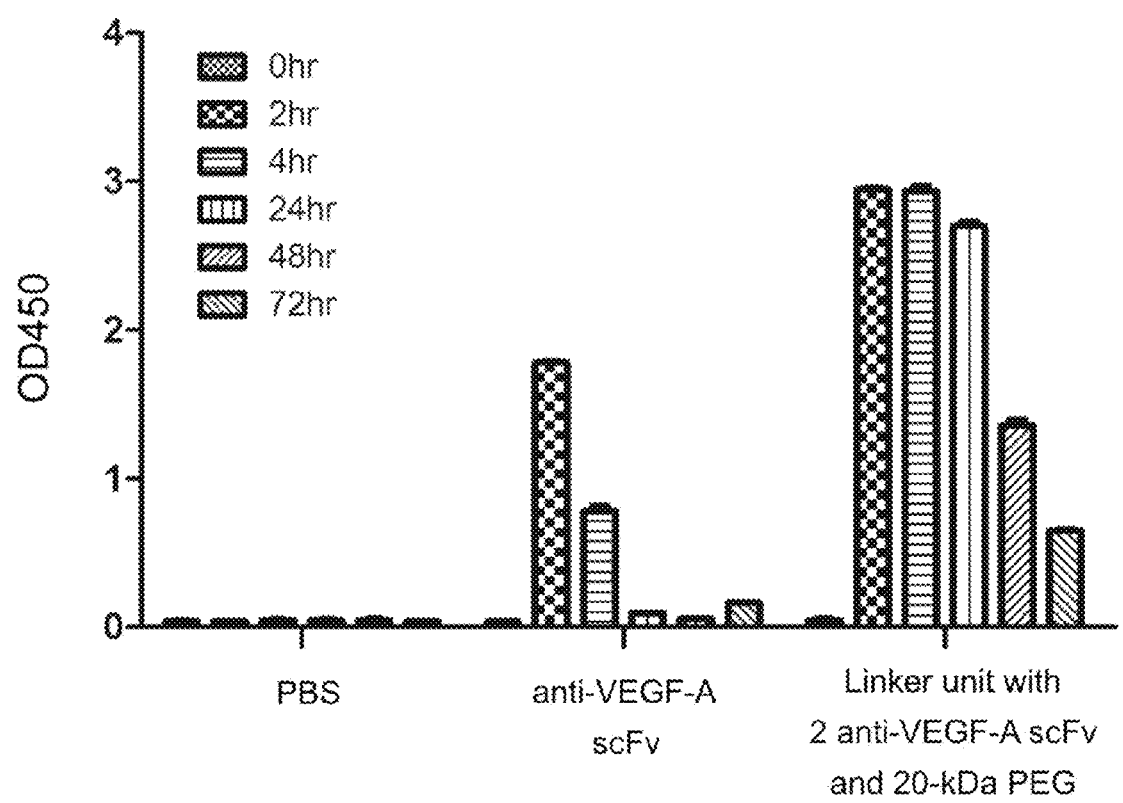
FIG. 26 shows the pharmacokinetic pattern of the molecular construct with 3scFv specific for VEGF-A and a 20 kDa PEG in mice.

The results, as summarized in FIG. 26 showed that the molecular construct with 3scFv specific for VEGF-A and a 20 kDa PEG chain maintained substantial serum concentrations even at 72 hours after the administration.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A linker unit comprising, a center core, a plurality of linking arms, and optionally a coupling arm, wherein,
the center core comprises, (1) a first polypeptide comprising a plurality of lysine (K) residues, wherein each K residue and its next K residue are separated by a filler sequence comprising glycine (G) and serine (S) residues, and the number of K residues ranges from 2 to 15; or (2) a second polypeptide comprising the sequence of $(X_{aa}\text{-}K)_n$, where $X_{aa}$ is a PEGylated amino acid having 2 to 12 repeats of ethylene glycol (EG) unit, and n is an integral from 2 to 15;
the plurality of linking arms are respectively linked to the K residues of the center core,
each of the plurality of linking arms has a maleimide group at its free terminus; and
the amino acid residue at the N- or C-terminus of the center core has an azide or an alkyne group; or the amino acid residue at the N- or C-terminus of the center core is a cysteine residue, and the thiol group of the cysteine residue is linked with the coupling arm having the azide, the alkyne, a tetrazine or a strained alkyne group at the free terminus of the coupling arm.

2. The linker unit of claim 1, wherein the filler sequence has the sequence of GS, GGS, GSG, or SEQ ID NOs: 1-16.

3. The linker unit of claim 1, wherein the first polypeptide comprises 2-15 units of the sequence of $G_{1\text{-}5}SK$.

4. The linker unit of claim 3, wherein the first polypeptide comprises the sequence of $(GSK)_{2\text{-}15}$.

5. The linker unit of claim 1, wherein each of the linking arms is a PEG chain having 2-20 repeats of EG units.

6. The linker unit of claim 1, wherein the coupling arm is a PEG chain having 2-12 repeats of EG units.

7. The linker unit of claim 1, wherein the amino acid residue having the azide group is L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine.

8. The linker unit of claim 1, wherein the amino acid residue having the alkyne group is L-homopropargylglycine (L-HPG), D-homopropargylglycine (D-HPG), or beta-homopropargylglycine (β-HPG).

9. The linker unit of claim 1, wherein the strained alkyne group is trans-cyclooctene (TCO), dibenzocyclooctyne (DBCO), difluorinated cyclooctyne (DIFO), bicyclononyne (BCN), or dibenzocyclooctyne (DICO).

10. The linker unit of claim 1, wherein the tetrazine group is 1,2,3,4-tetrazine, 1,2,3,5-tetrazine or 1,2,4,5-tetrazine, or derivatives thereof.

11. The linker unit of claim 1, further comprising a plurality of first elements that are respectively linked to the plurality of linking arms via thiol-maleimide reaction.

12. The linker unit of claim 11, further comprising a second element that is,
linked to the azide group via copper catalyzed azide-alkyne cycloaddition (CuAAC) reaction or strained-promoted azide-alkyne click chemistry (SPAAC) reaction;
linked to the alkyne group via CuAAC reaction;
linked to the strained alkyne group via inverse electron demand Diels-Alder (iEDDA) reaction or SPAAC reaction; or
linked to the tetrazine group via iEDDA reaction.

13. The linker unit of claim 12, wherein the second element is linked to the azide or alkyne group at the N- or C-terminus of the center core via CuAAC reaction.

14. The linker unit of claim 13, further comprising a third element that is linked to the coupling arm via iEDDA reaction.

15. The linker unit of claim 14, wherein the third element is a long PEG chain having a molecular weight of about 20,000 to 50,000 daltons.

16. The linker unit of claim 12, wherein the second element is linked to the azide group at the N- or C-terminus of the center core via SPAAC reaction.

17. The linker unit of claim 16, further comprising a third element that is linked to the coupling arm via iEDDA reaction.

18. The linker unit of claim 17, wherein the third element is a long PEG chain having a molecular weight of about 20,000 to 50,000 daltons.

19. The linker unit of claim 12, wherein,
the first element is a first single-chain variable fragment (scFv) specific for a cytokine or a receptor of the cytokine; or a soluble receptor of the cytokine; and
the second element is a second scFv specific for a tissue-associated extracellular matrix protein.

20. The linker unit of claim 19, wherein the tissue-associated extracellular matrix protein is selected from the group consisting of α-aggrecan, collagen I, collagen II, collagen III, collagen V, collagen VII, collagen IX, and collagen XI.

21. The linker unit of claim 19, wherein the cytokine is selected from the group consisting of tumor necrosis factor-α (TNF-α), interleukin-17 (IL-17), IL-1, IL-6, shared protein of IL-12 and IL-23, and B cell activating factor (BAFF).

22. The linker unit of claim 19, wherein the receptor of the cytokine is a receptor specific for IL-6 (IL-6R) or a receptor specific for IL-17 (IL-17R).

23. The linker unit of claim 19, wherein the soluble receptor of the cytokine is specific for TNF-α or IL-1.

24. The linker unit of claim 12, wherein,
the first element is a first scFv specific for a first cell surface antigen; and
the second element is a second scFv specific for a second cell surface antigen.

25. The linker unit of claim 24, wherein the first cell surface antigen is selected from the group consisting of, CD5, CD19, CD20, CD22, CD23, CD27, CD30, CD33, CD34, CD37, CD38, CD43, CD72a, CD78, CD79a, CD79b, CD86, CD134, CD137, CD138, and CD319.

26. The linker unit of claim 24, wherein the second cell surface antigen is CD3 or CD16a.

27. The linker unit of claim 12, wherein,
the first element is a peptide hormone, a growth factor, or a first scFv specific for a tumor-associated antigen; and
the second element is a second scFv specific for a cell surface antigen.

28. The linker unit of claim 27, wherein the peptide hormone is secretin, cholecystokinin (CCK), somatostatin, or thyroid-stimulating hormone (TSH).

29. The linker unit of claim 27, wherein the growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF).

30. The linker unit of claim 27, wherein the tumor-associated antigen is selected from the group consisting of human epidermal growth factor receptor (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM).

31. The linker unit of claim 27, wherein the cell surface antigen is CD3 or CD16a.

32. The linker unit of claim 12, wherein,
the first element is a first scFv specific for ligand of receptor activator of nuclear factor κB (RANKL); and
the second element is a second scFv specific for collagen I or osteonectin.

33. The linker unit of claim 12, wherein,
the first element is an scFv specific for VEGF-A; and
the second element is a long PEG chain having a molecular weight of about 20,000 to 50,000 daltons.

* * * * *